United States Patent
Szabady et al.

(10) Patent No.: US 10,507,221 B2
(45) Date of Patent: Dec. 17, 2019

(54) COMPOSITIONS AND METHODS FOR THE TREATMENT OF ALLERGY

(71) Applicant: Vedanta Biosciences, Inc., Cambridge, MA (US)

(72) Inventors: Rose L. Szabady, Cambridge, MA (US); Bernat Olle, Cambridge, MA (US); Bruce Roberts, Sudbury, MA (US)

(73) Assignee: Vedanta Biosciences, Inc., Cambridge, MA (US)

( * ) Notice: Subject to any disclaimer, the term of this patent is extended or adjusted under 35 U.S.C. 154(b) by 0 days.

(21) Appl. No.: 16/229,288

(22) Filed: Dec. 21, 2018

(65) Prior Publication Data

US 2019/0134107 A1 May 9, 2019

Related U.S. Application Data

(63) Continuation of application No. PCT/US2018/060187, filed on Nov. 9, 2018.

(60) Provisional application No. 62/721,786, filed on Aug. 23, 2018, provisional application No. 62/637,355, filed on Mar. 1, 2018, provisional application No. 62/583,777, filed on Nov. 9, 2017.

(51) Int. Cl.

| | | |
|---|---|---|
| *A61K 49/00* | (2006.01) | |
| *A61K 39/00* | (2006.01) | |
| *A61K 39/02* | (2006.01) | |
| *A61K 35/74* | (2015.01) | |
| *A61K 9/48* | (2006.01) | |
| *A61P 37/08* | (2006.01) | |
| *A61K 9/19* | (2006.01) | |
| *A61K 9/00* | (2006.01) | |

(52) U.S. Cl.
CPC ............ *A61K 35/74* (2013.01); *A61K 9/0053* (2013.01); *A61K 9/19* (2013.01); *A61K 9/48* (2013.01); *A61P 37/08* (2018.01)

(58) Field of Classification Search
CPC ..................................................... A61K 39/00
USPC ............. 242/9.1, 9.2, 184.1, 234.1; 435/243
See application file for complete search history.

(56) References Cited

U.S. PATENT DOCUMENTS

| | | |
|---|---|---|
| 2017/0028061 A1 | 2/2017 | Riken et al. |
| 2017/0216378 A1 | 8/2017 | Honda et al. |

FOREIGN PATENT DOCUMENTS

| | | |
|---|---|---|
| WO | WO 2017/079450 A1 | 5/2017 |
| WO | WO 2017/160944 A2 | 9/2017 |

OTHER PUBLICATIONS

PCT/US2018/060187, Mar. 5, 2019, International Search Report and Written Opinion.
PCT/US2018/060187, Jan. 16, 2019, Invitation to Pay Additional Fees.

*Primary Examiner* — Rodney P Swartz
(74) *Attorney, Agent, or Firm* — Wolf, Greenfield & Sacks, P.C.

(57) ABSTRACT

Provided herein are compositions and methods for the treatment of allergy, such as food allergy. Also provided herein are compositions and methods for modulating an immune response associated with allergy and/or inducing immune tolerance or desensitization to an allergy, such as a food allergy.

15 Claims, 37 Drawing Sheets
Specification includes a Sequence Listing.

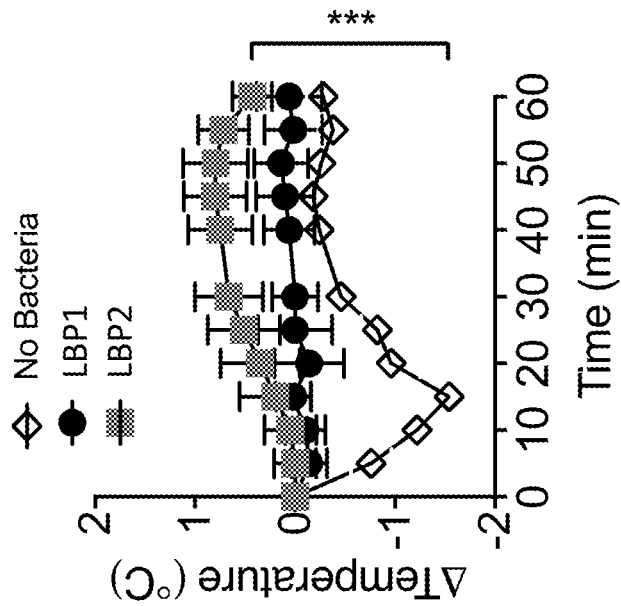
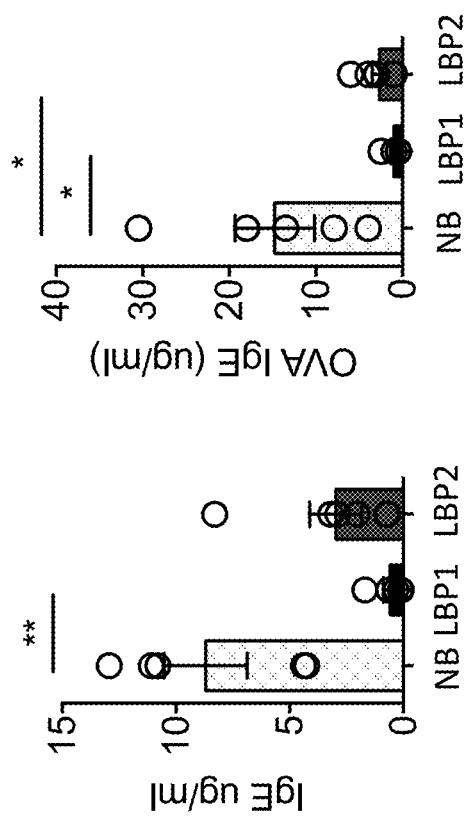
Fig. 8C
Fig. 8B
Fig. 8A

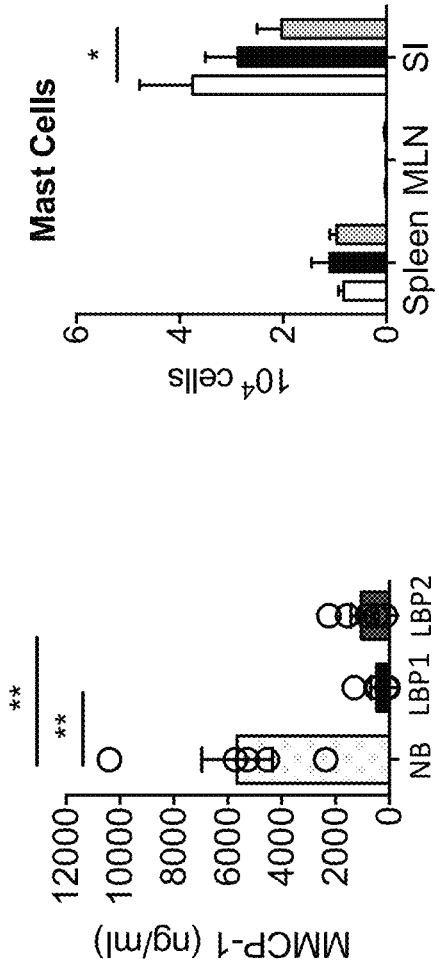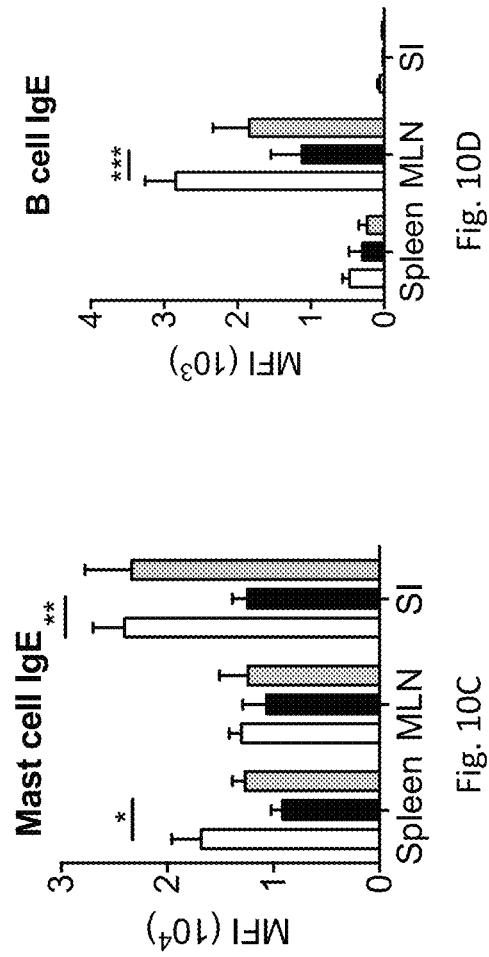
Fig. 10A
Fig. 10B
Fig. 10C
Fig. 10D

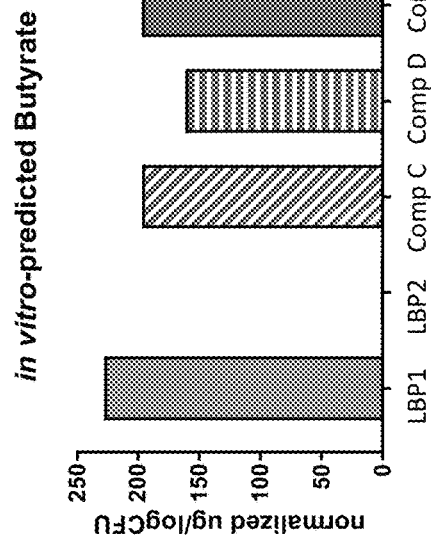
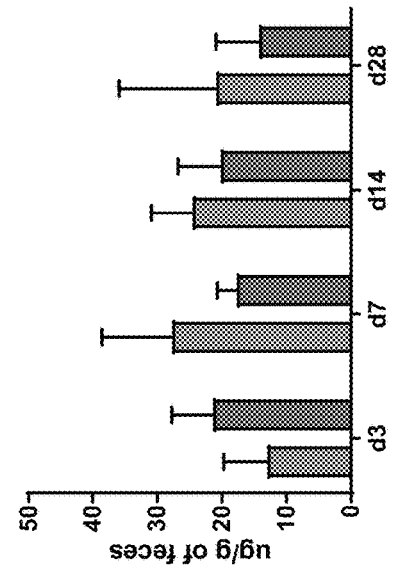
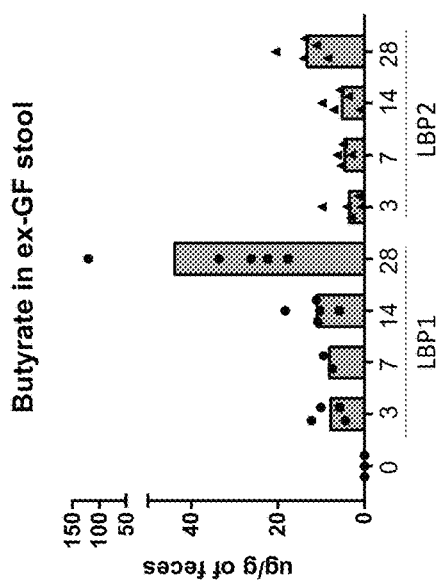
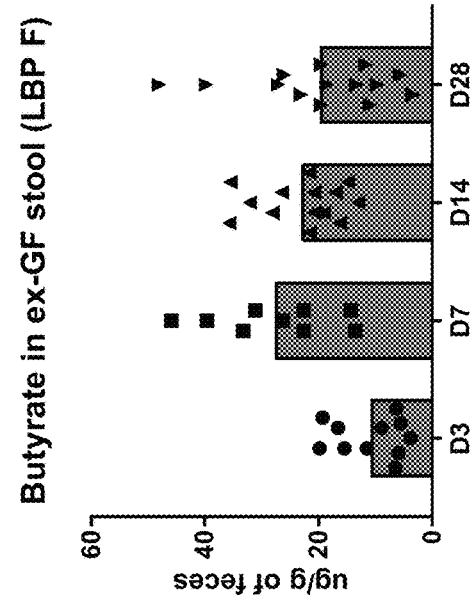

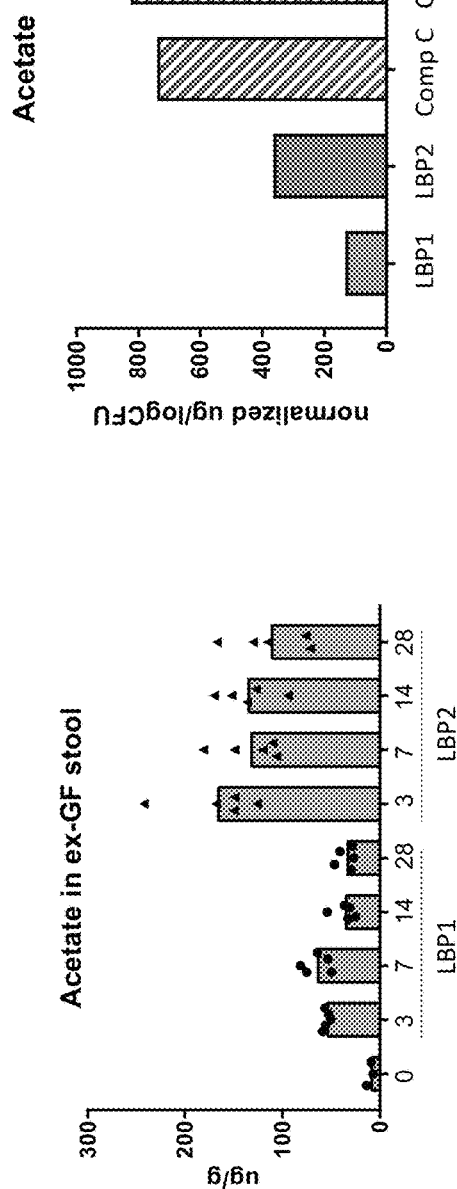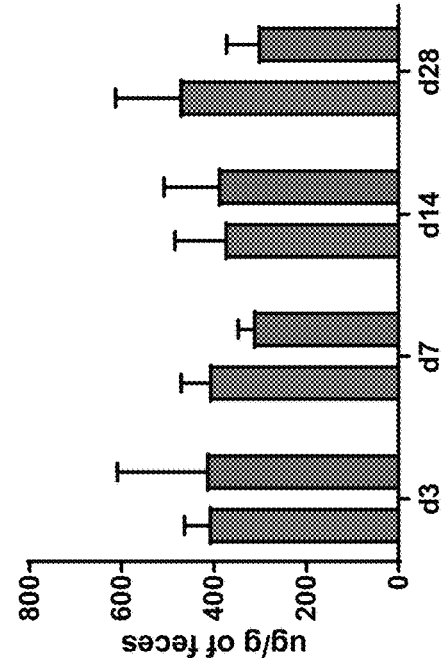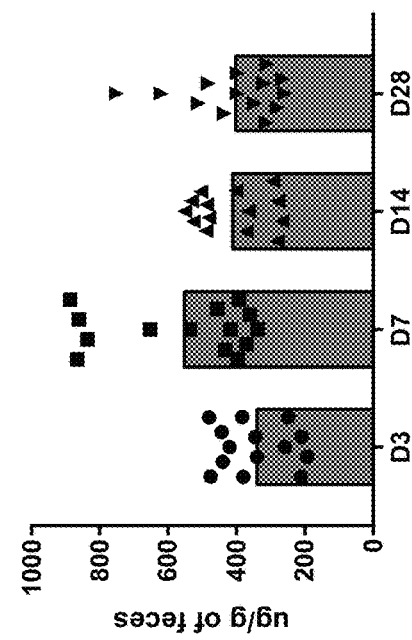

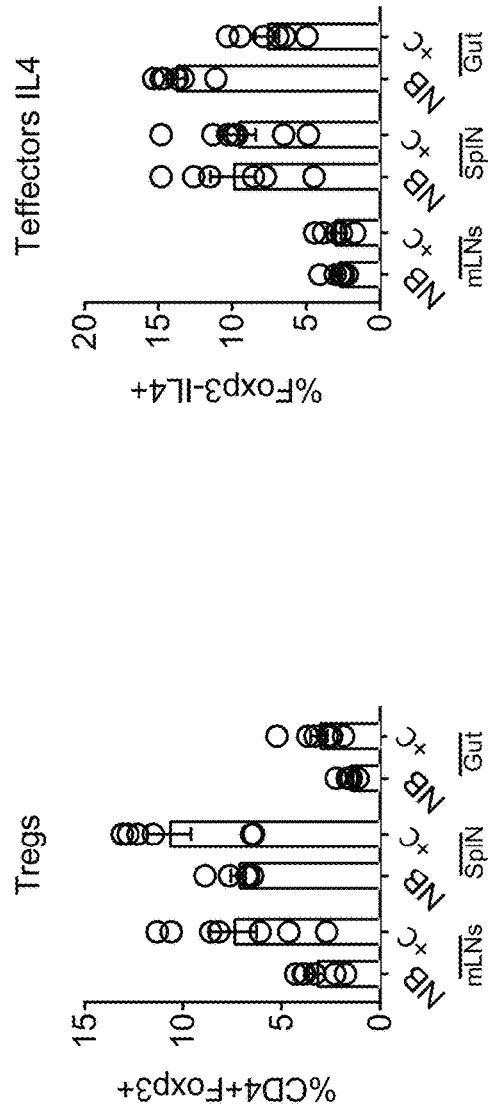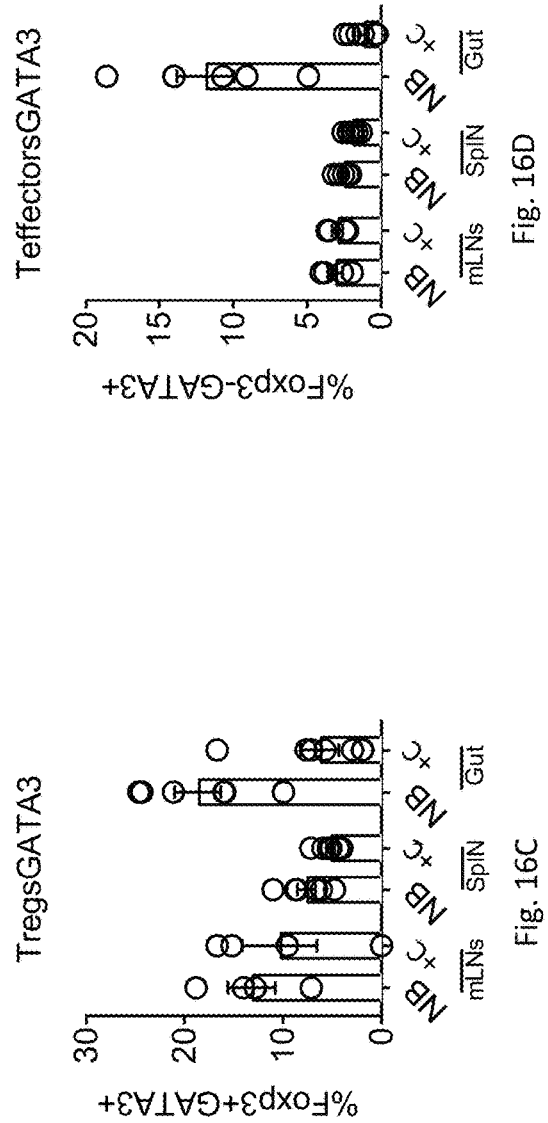

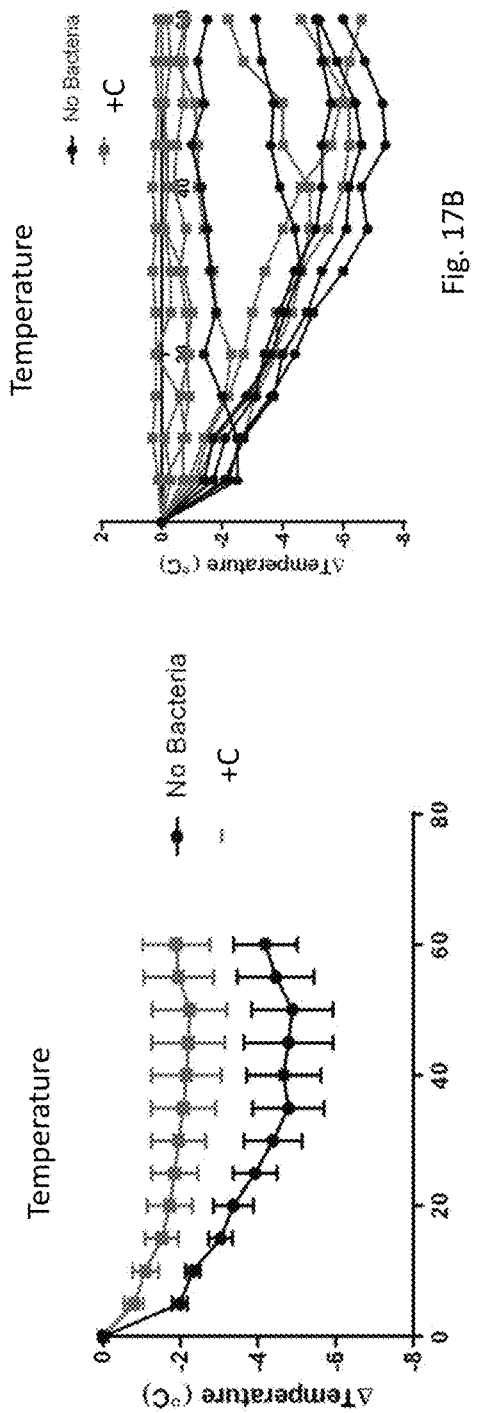
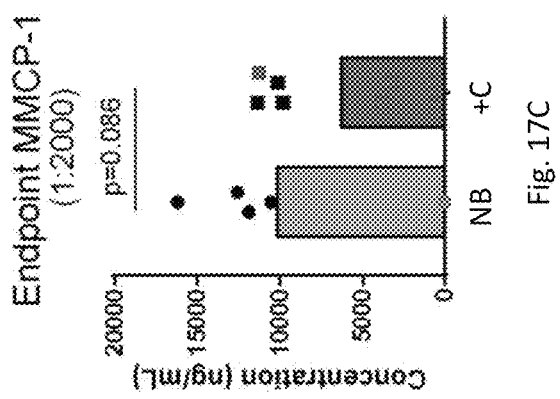
Fig. 17A
Fig. 17B
Fig. 17C

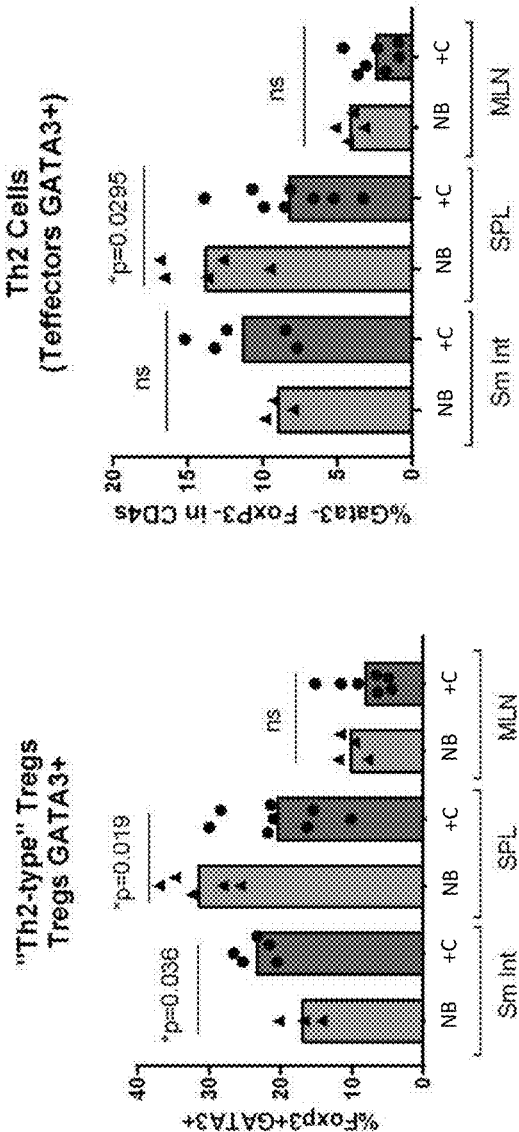
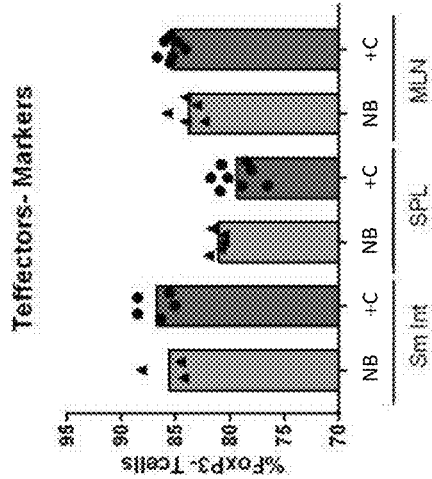
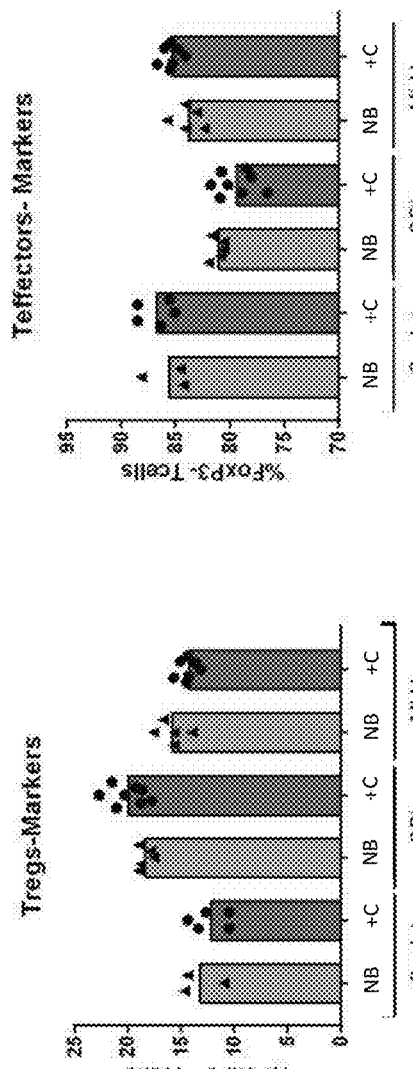
Fig. 18A
Fig. 18B
Fig. 18C
Fig. 18D

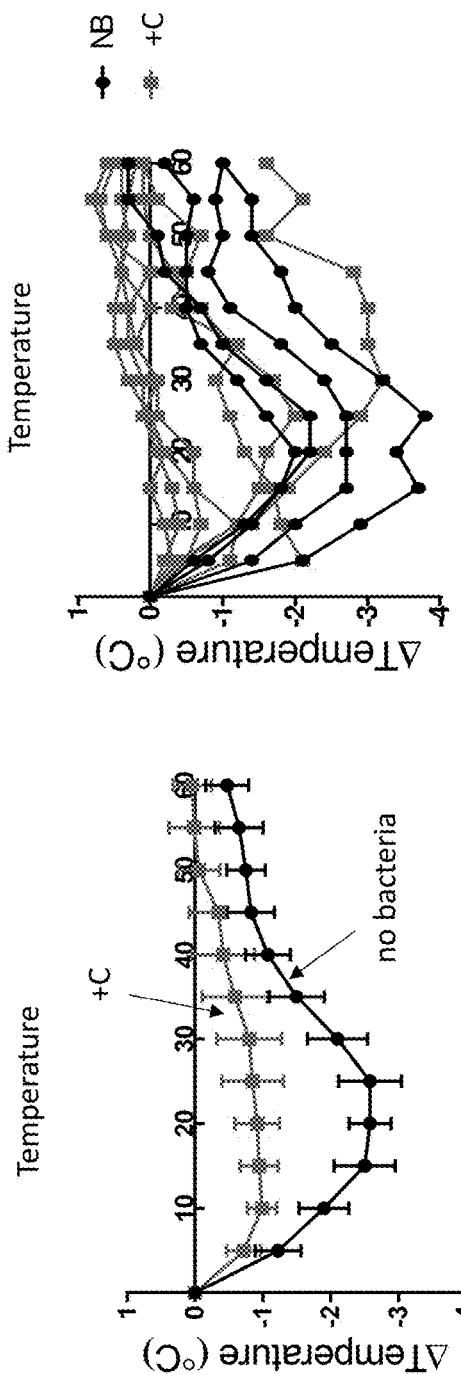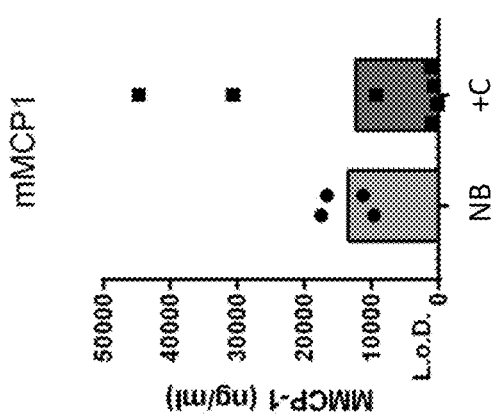
Fig. 20A
Fig. 20B
Fig. 20C

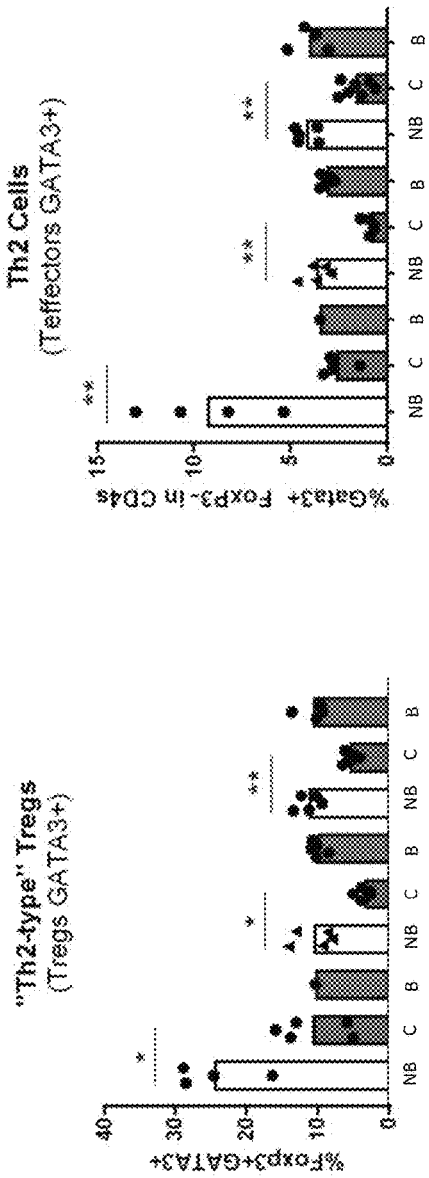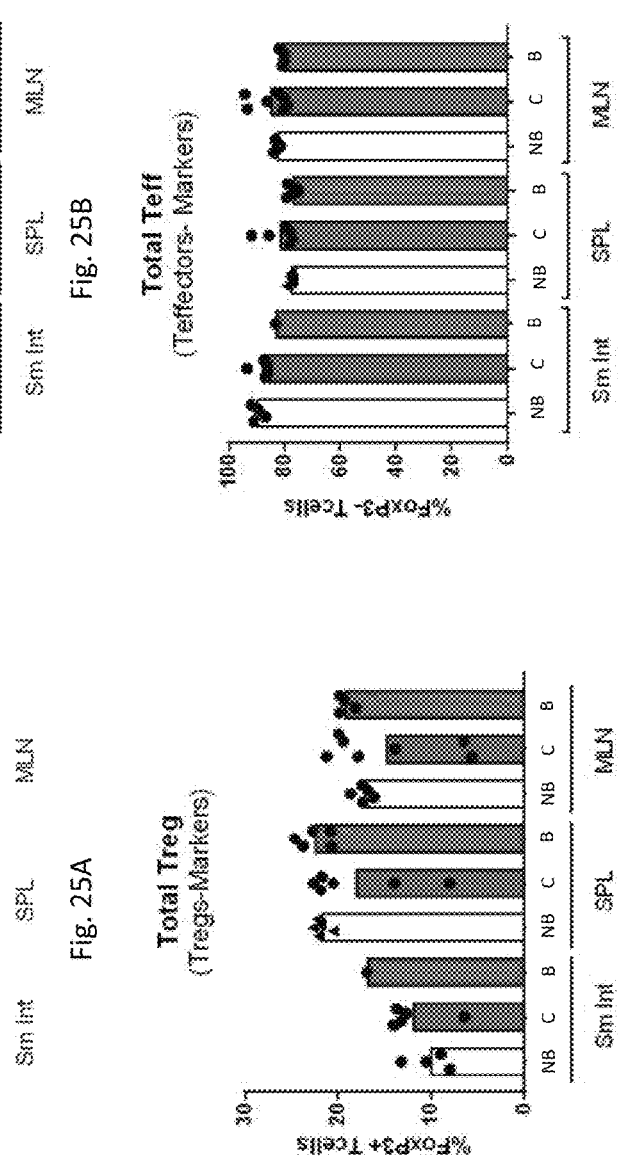
Fig. 25A Fig. 25B Fig. 25C Fig. 25D

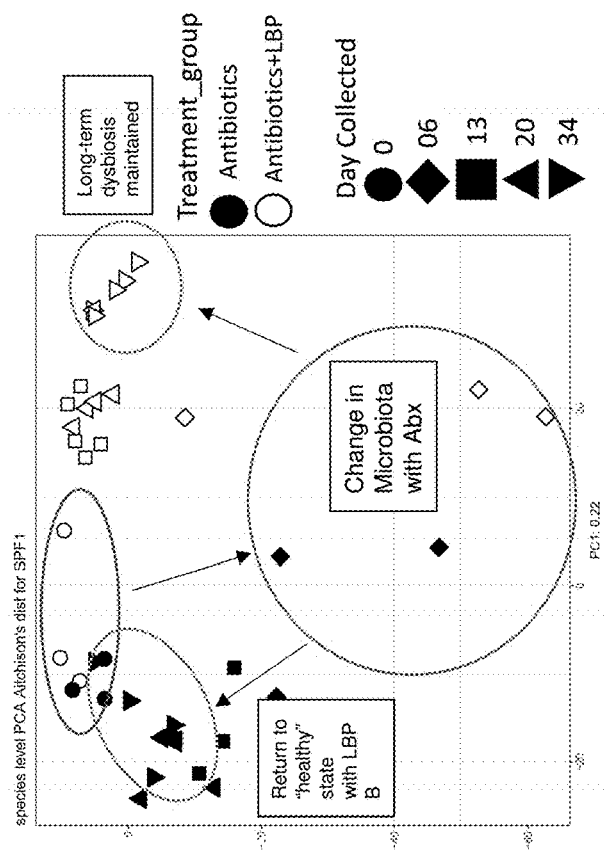
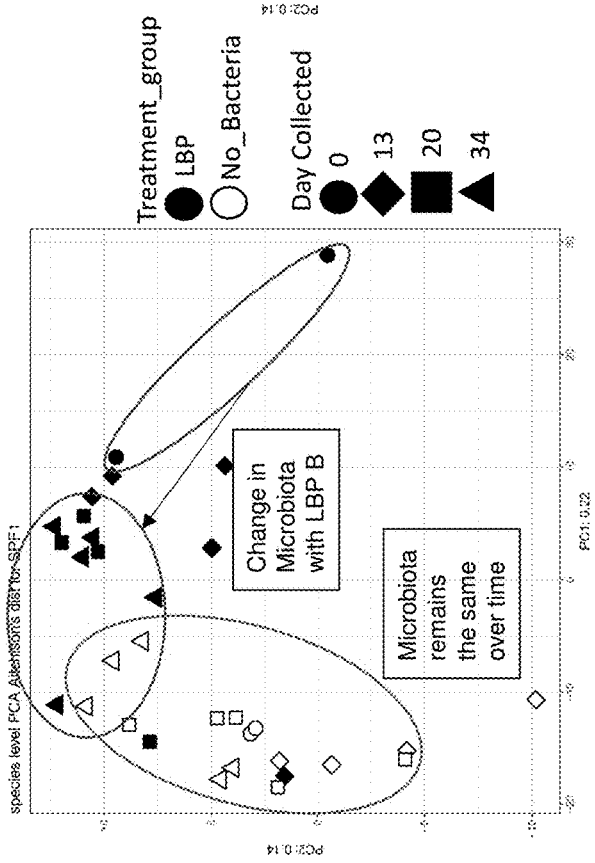
Fig. 31B
Fig. 31A

COMPOSITIONS AND METHODS FOR THE TREATMENT OF ALLERGY

RELATED APPLICATIONS

This application is a continuation of international application number PCT/US2018/060187, filed Nov. 9, 2018, which claims the benefit under 35 U.S.C. § 119(e) of U.S. provisional application No. 62/583,777, filed Nov. 9, 2017; U.S. provisional application No. 62/637,355, filed Mar. 1, 2018; and U.S. provisional application No. 62/721,786, filed Aug. 23, 2018. The entire contents of each of these referenced application are incorporated by reference herein.

FIELD OF INVENTION

Provided herein are compositions and methods for the treatment of allergy, such as food allergy. Also provided herein are compositions and methods for modulating an immune response associated with allergy and/or inducing immune tolerance or desensitization to an allergy, such as a food allergy.

BACKGROUND OF THE INVENTION

According to the World Health Organization statistics on allergy, the incidence of allergy has been on the rise in industrialized countries over the past 50 years, and nearly 40-50% of school-aged children world-wide being sensitive to at least one common allergen. See, e.g., Pawankar R, et al. *The WAO White Book on Allergy* (Update 2013). Although allergy may arise during childhood, it is also possible for allergies to develop or arise throughout one's life.

The severity of an allergic reaction upon exposure to an allergen can range broadly from mild symptoms to sometimes fatal reactions. Accordingly, improved therapeutics to treat allergy and allergic reactions are desired.

SUMMARY OF THE INVENTION

Aspects of the prevent disclosure provide methods of treating allergy comprising administering any of the compositions described herein. Also provided are methods of modulating an immune response associated with allergy comprising administering any of the compositions described herein. Also provided are methods of inducing immune tolerance or desensitization to an comprising administering any of the compositions described herein. Also provided are methods of modulating an immune response associated with allergy comprising administering an antibiotic and administering any of the compositions described herein. Also provided are methods of inducing immune tolerance or desensitization to an comprising administering an antibiotic and administering any of the compositions described herein.

Aspects of the present disclosure provide methods of treating a food allergy comprising administering to a subject in need thereof a therapeutically effective amount of a composition comprising two or more purified bacterial strains of species selected from the group consisting of *Clostridium bolteae, Anaerotruncus colihominis, Sellimonas intestinales, Clostridium symbiosum, Blautia producta, Dorea longicatena*, Erysipelotrichaceae bacterium, and *Subdolinogranulum* spp. Aspects of the present disclosure provide methods of treating a food allergy comprising administering to a subject in need thereof an antibiotic and administering to the subject a therapeutically effective amount of a composition comprising two or more purified bacterial strains of species selected from the group consisting of *Clostridium bolteae, Anaerotruncus colihominis, Sellimonas intestinales, Clostridium symbiosum, Blautia producta, Dorea longicatena*, Erysipelotrichaceae bacterium, and *Subdolinogranulum* spp. In some embodiments, the composition consists of purified bacterial strains *Clostridium bolteae, Anaerotruncus colihominis, Sellimonas intestinales, Clostridium symbiosum, Blautia producta*, Erysipelotrichaceae bacterium, and *Subdolinogranulum* spp. In some embodiments, the composition consists of purified bacterial strains *Clostridium bolteae, Anaerotruncus colihominis, Sellimonas intestinales, Clostridium symbiosum, Blautia producta, Dorea longicatena*, and *Subdolinogranulum* spp.

Aspects of the present disclosure provide methods of treating a food allergy comprising administering to a subject in need thereof a therapeutically effective amount of a composition comprising two or more purified bacterial strains of species selected from the group consisting of *Clostridium indolis, Anaerostipes caccae*, Lachnospiraceae bacterium, and *Clostridium symbiosum*. In some embodiments, the composition consists of purified bacterial strains *Clostridium indolis, Anaerostipes caccae*, Lachnospiraceae bacterium, and *Clostridium symbiosum*.

Aspects of the present disclosure provide methods of treating a food allergy comprising administering to a subject in need thereof a therapeutically effective amount of a composition comprising two or more purified bacterial strains of species selected from the group consisting of *Clostridium hathewayi, Clostridium bolteae, Sellimonas intestinalis*, and *Clostridium* species. In some embodiments, the composition consists of purified bacterial strains *Clostridium hathewayi, Clostridium bolteae, Sellimonas intestinalis*, and *Clostridium* species.

Aspects of the present disclosure provide methods of treating a food allergy, comprising administering to a subject in need thereof a therapeutically effective amount of a composition comprising two or more purified bacterial strains that comprise 16S rDNA sequences having at least 97% sequence identity with nucleic acid sequences selected from SEQ ID NOs: 1-8. Aspects of the present disclosure provide methods of treating a food allergy, comprising administering to a subject in need thereof an antibiotic and administering to the subject a therapeutically effective amount of a composition comprising two or more purified bacterial strains that comprise 16S rDNA sequences having at least 97% sequence identity with nucleic acid sequences selected from SEQ ID NOs: 1-8. In some embodiments, the composition consists of purified bacterial strains that comprise 16S rDNA sequences having at least 97% sequence identity with the nucleic acid sequences set forth as SEQ ID NOs: 1-5, 7, and 8. In some embodiments, the composition consists of purified bacterial strains that comprise 16S rDNA sequences having at least 97% sequence identity with the nucleic acid sequences set forth as SEQ ID NOs: 1-6 and 8.

Aspects of the present disclosure provide methods of treating a food allergy, comprising administering to a subject in need thereof a therapeutically effective amount of a composition comprising two or more purified bacterial strains that comprise 16S rDNA sequences having at least 97% sequence identity with nucleic acid sequences selected from SEQ ID NO: 10, SEQ ID NO: 11; SEQ ID NO: 13; and SEQ ID NO: 4. In some embodiments, the composition consists of purified bacterial strains that comprise 16S rDNA sequences having at least 97% sequence identity with the nucleic acid sequences set forth as SEQ ID NO: 10, SEQ ID NO: 11; SEQ ID NO: 13; and SEQ ID NO: 4.

Aspects of the present disclosure provide methods of treating a food allergy, comprising administering to a subject in need thereof a therapeutically effective amount of a composition comprising two or more purified bacterial strains that comprise 16S rDNA sequences having at least 97% sequence identity with nucleic acid sequences selected from SEQ ID NO: 9, SEQ ID NO: 1; SEQ ID NO: 3; and SEQ ID NO: 12. In some embodiments, the composition consists of purified bacterial strains that comprise 16S rDNA sequences having at least 97% sequence identity with the nucleic acid sequences set forth as SEQ ID NO: 9, SEQ ID NO: 1; SEQ ID NO: 3; and SEQ ID NO: 12.

In some embodiments, the method results in the suppression of the production of IgE antibodies. In some embodiments, the method results in the suppression of a Th2 immune response. In some embodiments, the method results in the suppression of an immune response associated with a food allergy.

In some embodiments, the bacterial strains are lyophilized. In some embodiments, one or more of the bacterial strains are in spore form. In some embodiments, each of the bacterial strains are in spore form. In some embodiments, one or more of the bacterial strains are in vegetative form. In some embodiments, each of the bacterial strains are in vegetative form.

In some embodiments, the administration is oral administration. In some embodiments, the composition is formulated for oral delivery. In some embodiments, the composition is formulated for rectal delivery. In some embodiments, the composition is formulated for delivery to the intestine. In some embodiments, the composition is formulated for delivery to the colon.

In some embodiments, the food allergy is selected from the group consisting of a nut allergy, a fish allergy, a wheat allergy, a milk allergy, a peanut allergy, a tree nut allergy, a shellfish allergy, a soy allergy, a seed allergy, a sesame seed allergy, and an egg allergy. In some embodiments, the subject is a human.

In some embodiments, the composition further comprises one or more adjuvants. In some embodiments, the adjuvant is associated with allergy treatment or immune tolerance.

Aspects of the present disclosure provide methods of modulating an immune response associated with a food allergy, comprising administering to a subject in need thereof a therapeutically effective amount of a composition comprising two or more purified bacterial strains of species selected from the group consisting of *Clostridium bolteae, Anaerotruncus colihominis, Sellimonas intestinales, Clostridium symbiosum, Blautia producta, Dorea longicatena*, Erysipelotrichaceae bacterium, and *Subdolinogranulum* spp. In some embodiments, the composition consists of purified bacterial strains *Clostridium bolteae, Anaerotruncus colihominis, Sellimonas intestinales, Clostridium symbiosum, Blautia producta*, Erysipelotrichaceae bacterium, and *Subdolinogranulum* spp. In some embodiments, the composition consists of purified bacterial strains *Clostridium bolteae, Anaerotruncus colihominis, Sellimonas intestinales, Clostridium symbiosum, Blautia producta, Dorea longicatena*, and *Subdolinogranulum* spp.

Aspects of the present disclosure provide methods of modulating an immune response associated with a food allergy, comprising administering to a subject in need thereof a therapeutically effective amount of a composition comprising two or more purified bacterial strains that comprise 16S rDNA sequences having at least 97% sequence identity with nucleic acid sequences selected from SEQ ID NO: 1-8. In some embodiments, the composition consists of purified bacterial strains that comprise 16S rDNA sequences having at least 97% sequence identity with the nucleic acid sequences set forth as SEQ ID NOs: 1-5, 7, and 8. In some embodiments, the composition consists of purified bacterial strains that comprise 16S rDNA sequences having at least 97% sequence identity with the nucleic acid sequences set forth as SEQ ID NOs: 1-6 and 8.

Aspects of the present disclosure provide methods of modulating an immune response associated with a food allergy, comprising administering to a subject in need thereof a therapeutically effective amount of a composition comprising two or more purified bacterial strains that comprise 16S rDNA sequences having at least 97% sequence identity with nucleic acid sequences selected from SEQ ID NO: 10, SEQ ID NO: 11; SEQ ID NO: 13; and SEQ ID NO: 4. In some embodiments, the composition consists of purified bacterial strains that comprise 16S rDNA sequences having at least 97% sequence identity with the nucleic acid sequences set forth as SEQ ID NO: 10, SEQ ID NO: 11; SEQ ID NO: 13; and SEQ ID NO: 4.

Aspects of the present disclosure provide methods of modulating an immune response associated with a food allergy, comprising administering to a subject in need thereof a therapeutically effective amount of a composition comprising two or more purified bacterial strains that comprise 16S rDNA sequences having at least 97% sequence identity with nucleic acid sequences selected from SEQ ID NO: 9, SEQ ID NO: 1; SEQ ID NO: 3; and SEQ ID NO: 12. In some embodiments, the composition consists of purified bacterial strains that comprise 16S rDNA sequences having at least 97% sequence identity with the nucleic acid sequences set forth as SEQ ID NO: 9, SEQ ID NO: 1; SEQ ID NO: 3; and SEQ ID NO: 12.

In some embodiments, the method results in the induction of the proliferation and/or accumulation of regulatory T cells. In some embodiments, the method results in the suppression of the production of IgE antibodies. In some embodiments, the method results in the suppression a Th2 immune response.

In some embodiments, the bacterial strains are lyophilized. In some embodiments, the bacterial strains are spray-dried. In some embodiments, one or more of the bacterial strains are in spore form. In some embodiments, each of the bacterial strains are in spore form. In some embodiments, one or more of the bacterial strains are in vegetative form. In some embodiments, each of the bacterial strains are in vegetative form.

In some embodiments, the administration is oral administration. In some embodiments, the composition is formulated for oral delivery. In some embodiments, the composition is formulated for rectal delivery. In some embodiments, the composition is formulated for delivery to the intestine. In some embodiments, the composition is formulated for delivery to the colon.

In some embodiments, the food allergy is selected from the group consisting of a nut allergy, a fish allergy, a wheat allergy, a milk allergy, a peanut allergy, a tree nut allergy, a shellfish allergy, a soy allergy, a seed allergy, a sesame seed allergy, and an egg allergy. In some embodiments, the subject is a human.

In some embodiments, the composition further comprises one or more adjuvants. In some embodiments, the adjuvant is associated with allergy treatment or immune tolerance.

Aspects of the present disclosure provide methods of inducing immune tolerance or desensitization to a food allergy, comprising administering to a subject in need thereof a therapeutically effective amount of a composition comprising two or more purified bacterial strains of species selected from the group consisting of *Clostridium bolteae, Anaerotruncus colihominis, Sellimonas intestinales, Clostridium symbiosum, Blautia producta, Dorea longicatena*, Erysipelotrichaceae bacterium, and *Subdolinogranulum* spp. In some embodiments, the composition consists of purified bacterial strains *Clostridium bolteae, Anaerotruncus colihominis, Sellimonas intestinales, Clostridium symbiosum, Blautia producta*, Erysipelotrichaceae bacterium, and *Subdolinogranulum* spp. In some embodiments, the composition consists of purified bacterial strains *Clostridium bolteae, Anaerotruncus colihominis*, Ruminococcus torques, *Clostridium symbiosum, Blautia producta, Dorea longicatena*, and *Subdolinogranulum* spp.

Aspects of the present disclosure provide methods of inducing immune tolerance or desensitization to a food allergy, comprising administering to a subject in need thereof a therapeutically effective amount of a composition comprising two or more purified bacterial strains of species selected from the group consisting of *Clostridium indolis, Anaerostipes caccae*, Lachnospiraceae bacterium, and *Clostridium symbiosum*. In some embodiments, the composition consists of purified bacterial strains *Clostridium indolis, Anaerostipes caccae*, Lachnospiraceae bacterium, and *Clostridium symbiosum*.

Aspects of the present disclosure provide methods of inducing immune tolerance or desensitization to a food allergy, comprising administering to a subject in need thereof a therapeutically effective amount of a composition comprising two or more purified bacterial strains of species selected from the group consisting of *Clostridium hathewayi, Clostridium bolteae, Sellimonas intestinalis*, and *Clostridium* species. In some embodiments, the composition consists of purified bacterial strains *Clostridium hathewayi, Clostridium bolteae, Sellimonas intestinalis* and *Clostridium* species.

Aspects of the present disclosure provide methods of inducing immune tolerance or desensitization to a food allergy, comprising administering to a subject in need thereof a therapeutically effective amount of a composition comprising two or more purified bacterial strains that comprise 16S rDNA sequences having at least 97% sequence identity with nucleic acid sequences selected from SEQ ID NO: 1-8. In some embodiments, the composition consists of purified bacterial strains that comprise 16S rDNA sequences having at least 97% sequence identity with the nucleic acid sequences set forth as SEQ ID NOs: 1-5, 7, and 8. In some embodiments, the composition consists of purified bacterial strains that comprise 16S rDNA sequences having at least 97% sequence identity with the nucleic acid sequences set forth as SEQ ID NOs: 1-6 and 8.

Aspects of the present disclosure provide methods of inducing immune tolerance or desensitization to a food allergy, comprising administering to a subject in need thereof a therapeutically effective amount of a composition comprising two or more purified bacterial strains that comprise 16S rDNA sequences having at least 97% sequence identity with nucleic acid sequences selected from SEQ ID NO: 10, SEQ ID NO: 11; SEQ ID NO: 13; and SEQ ID NO: 4. In some embodiments, the composition consists of purified bacterial strains that comprise 16S rDNA sequences having at least 97% sequence identity with the nucleic acid sequences set forth as SEQ ID NO: 10, SEQ ID NO: 11; SEQ ID NO: 13; and SEQ ID NO: 4.

Aspects of the present disclosure provide methods of inducing immune tolerance or desensitization to a food allergy, comprising administering to a subject in need thereof a therapeutically effective amount of a composition comprising two or more purified bacterial strains that comprise 16S rDNA sequences having at least 97% sequence identity with nucleic acid sequences selected from SEQ ID NO: 9, SEQ ID NO: 1; SEQ ID NO: 3; and SEQ ID NO: 12. In some embodiments, the composition consists of purified bacterial strains that comprise 16S rDNA sequences having at least 97% sequence identity with the nucleic acid sequences set forth as SEQ ID NO: 9, SEQ ID NO: 1; SEQ ID NO: 3; and SEQ ID NO: 12.

In some embodiments, the method results in the induction of the proliferation and/or accumulation of regulatory T cells. In some embodiments, the method results in the suppression of the production of IgE antibodies. In some embodiments, the method results in the suppression of a Th2 immune response.

In some embodiments, the bacterial strains are lyophilized. In some embodiments, the bacterial strains are spray-dried. In some embodiments, one or more of the bacterial strains are in spore form. In some embodiments, each of the bacterial strains are in spore form. In some embodiments, one or more of the bacterial strains are in vegetative form. In some embodiments, each of the bacterial strains are in vegetative form.

In some embodiments, the administration is oral administration. In some embodiments, the composition is formulated for oral delivery. In some embodiments, the composition is formulated for rectal delivery. In some embodiments, the composition is formulated for delivery to the intestine. In some embodiments, the composition is formulated for delivery to the colon.

In some embodiments, the food allergy is selected from the group consisting of a nut allergy, a fish allergy, a wheat allergy, a milk allergy, a peanut allergy, a tree nut allergy, a shellfish allergy, a soy allergy, a seed allergy, a sesame seed allergy, and an egg allergy. In some embodiments, the subject is a human.

In some embodiments, the composition further comprises one or more adjuvants. In some embodiments, the adjuvant is associated with allergy treatment or immune tolerance.

Aspects of the present disclosure also provide compositions comprising three or more purified bacterial strains of species selected from the group consisting of *Clostridium bolteae, Anaerotruncus colihominis, Sellimonas intestinales, Clostridium symbiosum, Blautia producta*, Erysipelotrichaceae bacterium, and *Subdolinogranulum* spp., and wherein the composition does not comprise *Dorea longicatena*. Aspects of the present disclosure also provide compositions comprising three or more purified bacterial strains selected from the group consisting of *Clostridium bolteae, Anaerotruncus colihominis, Sellimonas intestinales, Clostridium symbiosum, Blautia producta, Dorea longicatena*, and *Subdolinogranulum* spp., and wherein the composition does not comprise Erysipelotrichaceae bacterium.

Aspects of the present disclosure also provide compositions comprising three or more purified bacterial strains that comprise 16S rDNA sequences having at least 97% sequence identity with nucleic acid sequences selected from SEQ ID NO: 1-5, 7, and 8, wherein the composition does not comprise a bacterial strain comprising a 16S rDNA sequence having at least 97% sequence identity with the nucleic acid sequence provided by SEQ ID NO: 6. Aspects of the present disclosure also provide compositions comprising three or more purified bacterial strains that comprise 16S rDNA sequences having at least 97% sequence identity with nucleic acid sequences selected from SEQ ID NO: 1-6 and 8, wherein the composition does not comprise a bacterial strain comprising a 16S rDNA sequence having at least 97% sequence identity with the nucleic acid sequence provided by SEQ ID NO: 7.

In some embodiments, the composition induces the proliferation and/or accumulation of regulatory T cells. In some embodiments, the composition suppresses IgE antibody production. In some embodiments, the composition suppresses one or more Th2 immune response.

In some embodiments, the composition further comprises one or more adjuvants. In some embodiments, the adjuvant is associated with allergy treatment or immune tolerance.

Aspects of the present disclosure also provide pharmaceutical compositions comprising any of the compositions described herein and a pharmaceutically acceptable excipient. In some embodiments, the pharmaceutical composition is formulated for oral delivery. In some embodiments, the pharmaceutical composition is formulated for rectal delivery. In some embodiments, the pharmaceutical composition is formulated for delivery to the intestine. In some embodiments, the pharmaceutical composition is formulated for delivery to the colon.

Aspects of the present disclosure also provide food products comprising any of the compositions described herein and a nutrient.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways.

BRIEF DESCRIPTION OF THE DRAWINGS

The accompanying drawings are not intended to be drawn to scale. The figures are illustrative only and are not required for enablement of the disclosure. For purposes of clarity, not every component may be labeled in every drawing. In the drawings:

FIG. 8A shows the level of IgE antibodies in serum samples obtained from mice inoculated with LBP1 or LBP2, as compared to control mice (no bacteria, "NB"). FIG. 8B shows the level of OVA-specific IgE antibodies in serum samples obtained from mice inoculated with LBP1 or LBP2, as compared to control mice (no bacteria, "NB"). FIG. 8C shows the change in body temperature of mice inoculated with LBP 1 or LBP 2, or control mice (no bacteria).

FIG. 10A shows the level of mMCP-1 (MMCP-1) in serum samples from mice inoculated with LBP1 or LBP2, as compared to control mice (no bacteria, "NB"). FIG. 10B shows the level of Mast cells in the spleen, mesenteric lymph nodes (MLN), and small intestine (SI) of mice inoculated with LBP1 or LBP2, as compared to control mice (no bacteria, "NB"). FIG. 10C shows the level of IgE+ Mast cells (Mast cell IgE) in the spleen, mesenteric lymph nodes (MLN), and small intestine (SI) of mice inoculated with LBP1 or LBP2, as compared to control mice (no bacteria, "NB"). FIG. 10D shows the level of IgE+ B cells (B cell IgE) in the spleen, mesenteric lymph nodes (MLN), and small intestine (SI) of mice inoculated with LBP1 or LBP2, as compared to control mice (no bacteria, "NB"). For each of FIGS. 10B-10D, white bars are control mice (no bacteria), black bars are mice inoculated with LBP1, and gray bars are mice inoculated with LBP2. *, , and * represent statistical significance.

FIG. 11A shows the amount of butyrate produced in vivo germ-free mice inoculated with LBP1 or LBP2 at the indicated time points (days post inoculation), as measured in ex vivo stool samples. FIG. 11B shows the amount of butyrate produced in vitro by LBP 1, LBP2, Composition ("Comp") C, Composition D, or Composition B. FIG. 11C shows the amount of butyrate produced in vivo in germ-free mice inoculated with Composition B at the indicated time points (D=days post inoculation), as measured in ex vivo stool samples. FIG. 11D shows the amount of butyrate produced in vivo in germ-free mice inoculated with bacterial compositions at the indicated time points (D=days post inoculation), as measured in ex vivo stool samples. For each time point, the left column shows results from mice inoculated with Composition B, and the right column shows results from mice inoculated with Composition C.

FIG. 12A shows the amount of acetate produced in vivo in germ-free mice inoculated with LBP1 or LBP2 at the indicated time points (days post inoculation), as measured in ex vivo stool samples. FIG. 12B shows the amount of acetate produced in vitro by LBP 1, LBP2, Composition C, Composition D, or Composition B. FIG. 12C shows the amount of acetate produced in vivo in germ-free mice inoculated with Composition B at the indicated time points (D=days post inoculation), as measured in ex vivo stool samples. FIG. 12D shows the amount of acetate produced in vivo in germ-free mice inoculated with bacterial compositions at the indicated time points (D=days post inoculation), as measured in ex vivo stool samples. For each time point, the left column shows results from mice inoculated with Composition B, and the right column shows results from mice inoculated with Composition C.

FIG. 16A shows the percentage of Foxp3+ CD4+ regulatory T cells in the mesenteric lymph nodes (MLNs), spleen (Sp1N) and gut (small intestine) of mice inoculated with Composition C, as compared to control mice (no bacteria, "NB"). FIG. 16B shows the percentage of Foxp3+ IL4+ cells in the mesenteric lymph nodes (MLNs), spleen (Sp1N) and gut (small intestine) of mice inoculated with Composition C, as compared to control mice (no bacteria, "NB"). FIG. 16C shows the percentage of Foxp3+ GATA3+ cells in the mesenteric lymph nodes (MLNs), spleen (Sp1N) and gut (small intestine) of mice inoculated with Composition C, as compared to control mice (no bacteria, "NB"). FIG. 16D shows the percentage of Foxp3− IL4+ cells (% Foxp3−GATA3+) in the mesenteric lymph nodes (MLNs), spleen (Sp1N) and gut (small intestine) of mice inoculated with Composition C, as compared to control mice (no bacteria, "NB").

FIG. 17A shows the average change in body temperature (+/−SEM) of mice inoculated with Composition C (+C) or control mice (no bacteria). FIG. 17B shows the change in body temperature for individual mice inoculated with Composition C (+C) or control mice (no bacteria). FIG. 17C shows the level of mMCP-1 (MMCP-1) in serum samples from mice inoculated with Composition C (+C), as compared to control mice (no bacteria, "NB"). SEM=standard error of the mean. The results in FIGS. 17A and 17B were obtained using the experimental food allergy model shown in FIG. 7.

FIG. 18A shows the percentage of Foxp3+ GATA3+ "Th2-type" regulatory T cells in the mesenteric lymph nodes (MLN), spleen (SPL) and small intestine (Sm Int) of mice inoculated with Composition C (+C), as compared to control mice (no bacteria, "NB"). FIG. 18B shows the percentage of Foxp3−GATA3− Th2 effector T cells (% Gata3−FoxP3− in CD4s) in the mesenteric lymph nodes (MLN), spleen (SPL) and small intestine (Sm Int) of mice inoculated with Composition C (+C), as compared to control mice (no bacteria, "NB"). FIG. 18C shows the percentage of Foxp3+ regulatory T cells (% FoxP3+ Tcells) in the mesenteric lymph nodes (MLN), spleen (SPL) and small intestine (Sm Int) of mice inoculated with Composition C (+C), as compared to control mice (no bacteria, "NB"). FIG. 18D shows the percentage of Foxp3− effector T cells (% FoxP3− Tcells) in the mesenteric lymph nodes (MLN), spleen (SPL) and small intestine (Sm Int) of mice inoculated with Composition C (+C), as compared to control mice (no bacteria, "NB").

FIG. 20A shows the average change (+/−SEM) in body temperature of mice inoculated with Composition C (+C) or control mice (no bacteria). FIG. 20B shows the changes in body temperature for individual mice inoculated with Composition C (+C) or control mice (no bacteria). FIG. 20C shows the level of mMCP-1 (MMCP-1) in serum samples from mice inoculated with Composition C (+C), as compared to control mice (no bacteria, "NB"). SEM=standard error of the mean.

FIG. 25A shows the percentage of Foxp3+ GATA3+ "Th2-type" regulatory T cells in the mesenteric lymph nodes (MLN), spleen (SPL) and small intestine (Sm Int) of mice inoculated with Composition C (C) or Composition B (B), as compared to control mice (no bacteria, "NB"). FIG. 25B shows the percentage of Foxp3− GATA3− Th2 effector T cells (% Gata3+ FoxP3− in CD4s) in the mesenteric lymph nodes (MLN), spleen (SPL) and small intestine (Sm Int) of mice inoculated with Composition C (C) or Composition B (B), as compared to control mice (no bacteria, "NB"). FIG. 25C shows the percentage of Foxp3+ regulatory T cells (% FoxP3+ Tcells) in the mesenteric lymph nodes (MLN), spleen (SPL) and small intestine (Sm Int) of mice inoculated with Composition C (C) or Composition B (B), as compared to control mice (no bacteria, "NB"). FIG. 25D shows the percentage of Foxp3− effector T cells (% FoxP3− Tcells) in the mesenteric lymph nodes (MLN), spleen (SPL) and small intestine (Sm Int) of mice inoculated with Composition C (+C) or Composition B (+B) as compared to control mice (no bacteria, "NB"). The results shown in FIGS. 25A-25D are for the same experiment as in FIGS. 23A-24C.

FIG. 31A shows a plot of the microbial communities by Principal Component Analysis (PCA) of species showing fecal microbiome profiles and changes to the microbiome of mice that did not receive antibiotics and were inoculated with Composition B (LBP) or no bacteria. The microbial communities are shown for mice on Day 0 (prior to inoculation with Composition B dosing) and at Days 13, 20, and 34 during the course of weekly inoculation with Composition B. FIG. 31B a plot of the microbial communities by Principal Component Analysis (PCA) of species showing fecal microbiome profiles and changes to the microbiome of mice that received antibiotics and were inoculated with Composition B (Antibiotics+LBP) or no bacteria ("Antibiotics"). The microbial communities are shown for mice on Day 0 (prior to inoculation with Composition B), Day 6 (after antibiotic treatment and prior to inoculation with Composition B, and at Days 13, 20, and 34 during the course of weekly inoculation with Composition B. The results from FIGS. 31A and 31B show the fecal microbiome profiles of mice from FIGS. 30A and 30B.

DETAILED DESCRIPTION OF THE INVENTION

Figures 1, 2:
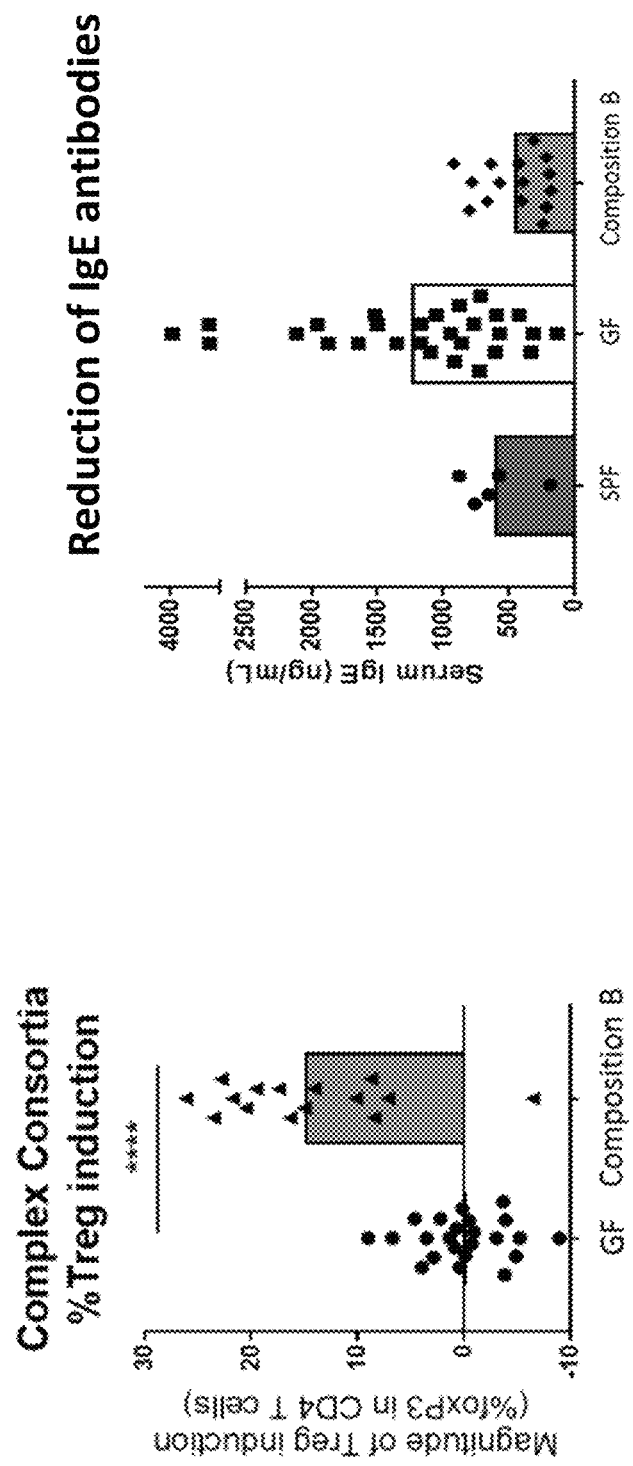
FIG. 1 shows the percentage of Foxp3+ CD4+ regulatory T cells (% foxP3 in CD4 T cells) induced in the intestine of germ-free mice inoculated with Composition B, as compared to control mice ("GF"). The data presented is cumulated from several independent experiments. To normalize between experiments, the average percentage of Foxp3-positive cells in the germ-free control mice was subtracted from each of the other mice in each experiment.
FIG. 2 shows the level of IgE antibodies in serum samples obtained from germ-free mice inoculated with Composition B, as compared to control mice germ-free mice ("GF") and specific-pathogen free mice ("SPF").

Current treatment regimens aim to reduce allergy or allergic reactions are focused on treating the symptoms of the allergic immune response, for example with anti-histamines, corticosteroids, or epinephrine. These methods fail to address the underlying undesired allergic immune responses stimulated upon contact or exposure to an allergen. An additional approach is desensitization therapy, also referred to as allergen immunotherapy, which requires identification of the specific allergen that induces the allergic reaction and then repeated administration of the allergen in effort to modulate the undesired immune response, effectively "desensitizing" the immune response to the allergen. However, it is not always possible to identify the specific allergen associated with the allergy and the numerous, repeated administrations may result in low patient compliance. Allergen immunotherapy may also not be possible for individuals with allergy associated with severe allergic reactions.

In the context of a food allergy, individuals are frequently recommended to eliminate foods containing or likely to contain the allergen that stimulates the allergic reaction. Without control of food preparation or accurate food labeling, the risk of an allergic reaction and exposure to the allergen, even at very low quantities, remain high despite dietary avoidance. Furthermore, the exclusion of particular foods or groups of foods may lead to nutritional deficiencies and significantly affect one's quality of life. Alternatively, methods of reducing the allergenicity of particular food, for example using processing methods, by reducing the amount of allergens in the foods are being explored. See, e.g., Verhoeckx et al. *Food and Chem. Toxicology* (2015) 80: 223-240; Bischoff et al. *Gastroenterology* (2005) 128(4): 1089-1113.

Provided herein are compositions and methods for treating allergy, such as food allergies, involving administering compositions of selected bacterial strains that modulate immune responses associated with allergy. Provided herein are compositions and methods that modulate immune responses associated with an allergy, such as a food allergy, to treat allergy in a subject. Also provided herein are compositions and methods for inducing immune tolerance or desensitization of an allergy, such as a food allergy.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Aspects of the present disclosure relate to compositions and methods for treating allergy, such as a food allergy, in a subject. Also provided are compositions and methods for modulating immune responses associated with allergy and/ or inducing immune tolerance or desensitization to an allergy. Allergy is characterized by an undesired immune response upon contact or exposure to a (non-self) substance that is typically considered harmless, referred to as an allergen. In the general population, contact or exposure to allergens does not elicit a substantial immune response and individuals are considered to be tolerant or not sensitive to the allergens. Accordingly, allergy may be referred to a hypersensitivity reaction to an allergen.

Allergic responses are driven by Th2 immune responses and may involve the undesired production and/or activity of allergen-specific antibodies, such as IgE antibodies, and allergen-specific lymphocytes, such as T cells and B cells. The development of an allergic response can be divided into three phases: sensitization phase, effector phase, and chronic phase. During the sensitization phase, allergens are taken-up, processed, and presented by antigen-presenting cells, leading to the production of allergen-specific IgE antibodies. The allergen-specific IgE antibodies can bind to high affinity IgE receptors (e.g., FcεR1) present on mast cells and basal cells. During the effector phase, interaction between the cell-bound allergen-specific IgE antibodies with the allergen results in degranulation of the cells releasing histamine, leukotrienes, and other mediators from the mast cells and basophils, which is then followed by infiltration of other cells to the tissue, such as basophils, eosinophils, and lymphocytes. The chronic phase results from repeated allergic reactions and inflammation. Bischoff et al. *Gastroenterology* (2005) 128(4): 1089-1113.

The symptoms and severity of an allergy may depend on factors such as type of immune response(s) involved, the duration and magnitude of the immune response(s), amount of allergen, and the site of contact/exposure to the allergen. Examples of allergy symptoms include, without limitation, skin rash, skin redness, hives, skin bumps/patches/welts, itchy/watery eyes, headache, sneezing, wheezing, shortness of breath, chest tightness, cough, runny nose, sore throat, swelling, nausea, vomiting, diarrhea, and anaphylaxis.

A subject may contact or be exposed to an allergen that induces an allergic reaction by any route known in the art, for example, through ingestion, inhalation, injection, or direct contact. The symptoms associated with the allergic reaction may be localized to the site of contact or exposure to the allergen, for example a region of the skin, respiratory tract, or gastrointestinal tract, a distal site, or may become systemic, such as in the case of anaphylaxis.

Immune responses stimulated in response to contact or exposure to an allergen may be referred to as allergic reactions. In general, an allergic reaction may occur immediately after contact or exposure to an allergen or within about a half-hour or longer after contact or exposure.

Examples of allergies that can be treated according to the compositions and methods provided herein, include without limitation, allergic asthma, allergic colitis, animal allergies, atopic allergies, hay fever, skin allergy, hives, atopic dermatitis, anaphylaxis, allergic rhinitis, drug or medicinal allergy, eczema (atopic dermatitis), food allergy, fungal allergy, insect allergy (including insect bite/venom allergies), mold allergies, plant allergies, and pollenosis. In some embodiments, the allergy is a food allergy.

Aspects of the present disclosure relate to treating food allergy and/or modulating an immune response associated with a food allergy in a subject. Also provided herein are methods of inducing immune tolerance or desensitization to a food allergy. As used herein, the term "food allergy" refers to an undesired allergic immune response to a food, or specifically, to an allergen present in the food. In some embodiments, an allergic reaction associated with a food allergy is induced following contact, for example through ingestion, of a food or foods containing the same or similar allergens. As will be evident to one of skill in the art, the symptoms associated with the food allergy may manifest in the gastrointestinal tract of the subject, for example, following ingestion with food containing the allergen; however, the allergic reaction may affect other sites, such as the respiratory tract or skin.

Food allergies are generally considered to be IgE-mediated immune reactions, however non-IgE-mediated food allergies as well as mixed IgE-mediated/non-IgE-mediated food allergies. See, e.g., Fiocchi et al. "Food Allergy" World Allergy Organization: March 2017. IgE-mediated food allergies tend to occur immediately or within about 2 hours following contact with the allergen and include hives (acute uticaria), angioedema, swelling, anaphylaxis, food-associated exercise-induced anaphylaxis, oral allergy syndrome, and/or immediate gastrointestinal hypersensitivity involving vomiting and pain. Non-IgE-mediated immune responses involved in food allergy, also referred to as cell-mediated responses, are delayed hypersensitivity reactions and may involve food protein-induced enterocolitis syndrome, food protein-induced allergic proctocolitis, allergic contact dermatitis, and Heiner syndrome. Mixed or combined IgE-mediated/non-IgE-mediated immune responses involved in food allergy are associated with both IgE and T cell mediated effects and may include atopic dermatitis, eosinophilic esophagitis, and/or eosinophilic gastroenteritis.

In contrast to food allergies, food intolerance is not generally considered to be mediated by the immune system and onset occurs between about 30 mins after exposure to within 48 hours after exposure.

In some embodiments, the compositions and methods described herein are used to treat an IgE-mediated food allergy. In some embodiments, the compositions and methods described herein are used to modulate an immune response associated with an IgE-mediated food allergy. In some embodiments, the compositions and methods described herein are used to induce immune tolerance or desensitization to an IgE-mediated food allergy. The compositions and methods described herein may also be used in the context of non-IgE mediated food allergies and/or mixed or combined IgE-mediated/non-IgE-mediated food allergies.

Examples of food allergies include, without limitation, peanut allergy, tree nut allergy, egg allergy, corn allergy, fruit allergy, milk allergy, garlic allergy, soy allergy, wheat allergy, seafood allergy, fish allergy (e.g., shellfish allergy), and seed allergy (e.g., sesame seed allergy).

Non-limiting examples of foods containing allergens to which a food allergy may occur include abalone (perlemoen), acerola, Alaska pollock, almond, aniseed, apple, apricot, avocado, banana, barley, bell pepper, Brazil nut, buckwheat, cabbage, carp, carrot, cashew, caster bean, celery, celeriac, cherry, chestnut, chickpea (garbanzo, bengal gram), cococa, coconut, cod, cotton seed, courgett (zucchini), crab, date, egg, fig, fish, flax seed (linseed), frog, garden plum, garlic, grape, hazelnut, kiwi fruit (Chinese gooseberry), lentil, lettuce, lobster, lupin (lupine), lychee, mackerel, maize (corn), mango, melon, milk, mustard, oat oyster, peach, peanut (ground nuts, monkey nuts), pear, pecan, persimmon, pine nut, pineapple, pomegranate, poppy seed, potato, pumpkin, rice, rye, salmon, sesame, sesame seed, shrimp (black tiger shrimp, brown shrimp, greasyback shrimp, Indian prawn, Neptune rose shrimp, white shrimp), snail, soybean (soya), squid, strawberry, sunflower seed, tomato, tuna, turnip, walnut, and wheat (bread-making wheat, pasta wheat, kamut, spelt).

Also within the scope of the present disclosure are compositions and methods that may be used to treat a disease or disorder associated with an immune response that is associated with Th2 immune response(s).

In some embodiments, the compositions and methods described here are used to treat a disease or disorder associated with enhanced levels of IgE antibodies. Examples of diseases or disorders that may be associated with enhanced levels of IgE antibodies include, without limitation hyper IgE (Job's) syndrome, IgE myeloma, lymphoproliferative disorders, Sézary's syndrome, Kimura's disease, parasitosis, HIV infection, vasculitis, systemic lupus erythematosus, and juvenile systemic lupus erythematosus.

In one aspect, the disclosure provides compositions and methods of treatment for a disease or disorder, such as allergy (e.g., food allergy), in a subject. As used herein, "subject," "individual," and "patient" are used interchangeably, and refer to a vertebrate, preferably a mammal such as a human. Mammals include, but are not limited to, human primates, non-human primates or murine, bovine, equine, canine or feline species. In some embodiments, the subject is a human. In some embodiments, the human subject is a neonatal subject, a pediatric subject, an adolescent subject, an adult subject, or a geriatric subject. In some embodiments, the subject has or is at risk of having an allergy, such as a food allergy. In some embodiments, the subject has had one or allergic reactions following contact or exposure to a particular food or group of foods containing an allergen. In some embodiments, the subject has had a medical history associated with allergy, such as a food allergy. In some embodiments, the subject has a family history of allergy or of an allergy to a specific allergen. For example, a family history may influence the likelihood for that subject to have or develop an allergy, such as a food allergy. Additionally, a subject having a food allergy to a specific food (e.g., specific allergen in a food) may also predispose that subject to have or develop a food allergy to a different food (e.g., a different specific allergen in a food).

In some embodiments, the subject has a risk factor associated with developing an allergy. Examples of risk factors associated with the development of a food allergy include, without limitation, an immature mucosal immune system, early introduction of solid food, hereditary increase in mucosal permeability, IgA deficiency or delayed IgA production, inadequate challenge of the intestinal immune system with commensal flora, genetically determined bias toward Th2 immune responses, polymorphisms of Th2 cytokine or IgE receptor genes, impaired enteric nervous system, immune alterations (e.g., low levels of TGF-β), and gastrointestinal infections (Bischoff et al. *Gastroenterology* (2005) 128 (4) 1089-1113).

Any of the compositions described herein may be administered to a subject in a therapeutically effective amount or a dose of a therapeutically effective amount to treat or prevent a disease or disorder (e.g., food allergy). The terms "treat" or "treatment" refer to reducing or alleviating one or more of the symptoms associated with a disease (e.g., an allergy such as food allergy). The terms "prevent" or "prevention" encompass prophylactic administration and may reduce the incidence or likelihood of the occurrence of the disease or disorder (e.g., food allergy). In some embodiments, the composition reduces the incidence or likelihood of the occurrence of an allergic reaction, such as an allergic reaction associated with a food or food allergen. For instance, in some embodiments, administration of the compositions provided herein result in an altered microbiome in the subject that provides an effect in a subject that reduces the incidence or likelihood of an allergic reaction. For instance, in some embodiments, administration of the compositions provided herein result in a healthy microbiome in the subject that provides an effect in a subject that reduces the incidence or likelihood of an allergic reaction. In some embodiments, administration of the composition provided herein result in a reduction or alleviation of one or more symptom associated with allergy, such as a symptom associated with an allergic reaction.

In some embodiments, the compositions and methods described herein are used to induce immune tolerance to an allergen associated with an allergy (e.g., a food allergy) or desensitize an immune response to an allergen associated with an allergy (e.g., a food allergy). As used herein, the terms "tolerance" and "immune tolerance" in the context of allergy refer to a reduced responsiveness or non-responsiveness of the immune response to one or more stimuli, such as an allergen associated with allergy. In particular, tolerance or immune tolerance refer to reduced responsiveness or non-responsiveness of the immune response to one or more stimuli over a sustained or long term period of time. In contrast, the term "desensitize" in the context of allergy refers a reversible state of reduced responsiveness or non-responsiveness of the immune response to one or more stimuli, for example during the course of a desensitization regimen.

In some embodiments, the compositions and methods described herein are used to modulate an immune response associated with an allergy (e.g., a food allergy). As will be evident to one of skill in the art, the compositions and methods described herein may enhance one or more immune response(s) associated with an allergy and reduce or suppress one or more other immune response(s) associated with the allergy.

In some embodiments, the compositions and methods described herein induce the proliferation and/or accumulation of regulatory T cells, also referred to as "Tregs." Regulatory T cells can generally be characterized by the expression of FoxP3, CD25, and CD4. In some embodiments, administration of the compositions described herein results in an increase in the proliferation and/or accumulation of regulatory T cells (e.g., total Tregs or allergen-specific Tregs) in the subject. In some embodiments, administration of the compositions described herein results in an increase in the proliferation and/or accumulation of regulatory T cells (e.g., total Tregs or allergen-specific Tregs) at a particular site (e.g., the gastrointestinal tract) in the subject. In some embodiments, administration of the compositions described herein results in an increase the proliferation and/or accumulation of regulatory T cells (e.g., total Tregs or allergen-specific Tregs) by at least 1.1-fold, 1.2-fold, 1.3-fold, 1.4-fold, 1.5-fold, 2-fold, 3-fold, 4-fold, 5-fold, 6-fold, 7-fold, 8-fold, 9-fold, 10-fold, 20-fold, 30-fold, 40-fold, 50-fold, 100-fold, 1000-fold, $10^4$-fold, $10^5$-fold or more, as compared to the quantity of regulatory T cells in the subject (or particular site in the subject) prior to administration of the compositions. In some embodiments, administration of the compositions described herein results in an increase the proliferation and/or accumulation of regulatory T cells (e.g., total Tregs or allergen-specific Tregs) by at least 1.5-fold, 2-fold, 3-fold, 4-fold, 5-fold, 6-fold, 7-fold, 8-fold, 9-fold, 10-fold, 20-fold, 30-fold, 40-fold, 50-fold, 100-fold, 1000-fold, $10^4$-fold, $10^5$-fold or more, as compared to the quantity of regulatory T cells in another subject (e.g., a reference subject) who did not receive the compositions.

In some embodiments, administration of the compositions described herein results in an increase the proliferation and/or accumulation of regulatory T cells (e.g., total Tregs or allergen-specific Tregs) by at least 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%, 95%, 100%, 125%, 150% or more, as compared to the quantity of regulatory T cells in the subject (or particular site in the subject) prior to administration of the compositions. In some embodiments, administration of the compositions described herein results in an increase the proliferation and/or accumulation of regulatory T cells (e.g., total Tregs or allergen-specific Tregs) by at least 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%, 95%, 100%, 125%, 150% or more, as compared to the quantity of regulatory T cells in another subject (e.g., a reference subject) who did not receive the compositions.

The induction of Treg cells and corresponding allergy treatment are intricately related. In some embodiments, in the treatment of one or more allergies, it is desired to have a Treg induction that is a range associated with treatment efficacy for the one more allergies. In some embodiments, for a particular allergy treatment regimen it is desired to have a Treg response that is significantly strong to induce the desired allergy treatment effect, but not so strong as to result in undesired immunological events. In some embodiments, administration of the compositions described herein results in an increase the proliferation and/or accumulation of regulatory T cells (e.g., total Tregs or allergen-specific Tregs) by between 1% and 20%, 2% and 19%, 3% and 17%, 4% and 16%, 4% and 15%, 5% and 15%, 6% and 14%, 7% and 13%, 8% and 12%, 5% and 10%, 5% and 15%, 10% and 15%, or 8% and 15% as compared to the quantity of regulatory T cells in the subject (or particular site in the subject) prior to administration of the compositions. In some embodiments, administration of the compositions described herein results in an increase the proliferation and/or accumulation of regulatory T cells (e.g., total Tregs or allergen-specific Tregs) by between 1% and 20%, 2% and 19%, 3% and 17%, 4% and 16%, 4% and 15%, 5% and 15%, 6% and 14%, 7% and 13%, 8% and 12%, 5% and 10%, 5% and 15%, 10% and 15%, or 8% and 15% as compared to the quantity of regulatory T cells in another subject (e.g., a reference subject) who did not receive the compositions.

In some embodiments, administration of the compositions described herein results in an increase in activity of regulatory T cells (e.g., total Tregs or allergen-specific Tregs) at a particular site (e.g., the gastrointestinal tract) in the subject. In some embodiments, administration of the compositions described herein results in an increase in activity of regulatory T cells (e.g., total Tregs or allergen-specific Tregs) by at least 1.1-fold, 1.2-fold, 1.3-fold, 1.4-fold, 1.5-fold, 2-fold, 3-fold, 4-fold, 5-fold, 6-fold, 7-fold, 8-fold, 9-fold, 10-fold, 20-fold, 30-fold, 40-fold, 50-fold, 100-fold, 1000-fold, $10^4$-fold, $10^5$-fold or more, as compared to the activity of regulatory T cells in the subject (or particular site in the subject) prior to administration of the compositions. In some embodiments, administration of the compositions described herein results in an increase in activity of regulatory T cells (e.g., total Tregs or allergen-specific Tregs) by at least 1.5-fold, 2-fold, 3-fold, 4-fold, 5-fold, 6-fold, 7-fold, 8-fold, 9-fold, 10-fold, 20-fold, 30-fold, 40-fold, 50-fold, 100-fold, 1000-fold, $10^4$-fold, $10^5$-fold or more, as compared to the activity of regulatory T cells in another subject (e.g., a reference subject) who did not receive the compositions.

In some embodiments, administration of the compositions described herein results in an increase in the activity of regulatory T cells (e.g., total Tregs or allergen-specific Tregs) by at least 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%, 95%, 100%, 125%, 150% or more, as compared to the activity of regulatory T cells in the subject (or particular site in the subject) prior to administration of the compositions. In some embodiments, administration of the compositions described herein results in an increase in the activity of regulatory T cells (e.g., total Tregs or allergen-specific Tregs) by at least 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%, 95%, 100%, 125%, 150% or more, as compared to the activity of regulatory T cells in another subject (e.g., a reference subject) who did not receive the compositions.

The abundance of regulatory T cells (e.g., total Tregs or allergen-specific Tregs) can be assessed by any method known in the art, for example by detecting a cellular marker indicative of regulatory T cells (e.g., FoxP3), assessing a direct or indirect activity of regulatory T cells, and/or by measuring the production of one or more cytokines produced by regulatory T cells (e.g., IL-10).

In some embodiments, the compositions and methods described herein suppress the production of IgE antibodies. In some embodiments, the compositions and methods suppress the production of total IgE antibodies in the subject. In some embodiments, the compositions and methods suppress the production of IgE antibodies that are specific to an allergen (e.g., allergen-specific IgE antibodies) associated with an allergy, e.g., a food allergen associated with a food allergy. In some embodiments, administration of the compositions described herein results in levels of IgE antibodies (e.g., total IgE antibodies or allergen-specific IgE antibodies) that are reduced by at least 1.5-fold, 2-fold, 3-fold, 4-fold, 5-fold, 6-fold, 7-fold, 8-fold, 9-fold, 10-fold, 20-fold, 30-fold, 40-fold, 50-fold, 100-fold, 1000-fold, $10^4$-fold, $10^5$-fold or more, as compared to the level of IgE antibodies (e.g., total IgE antibodies or allergen-specific IgE antibodies) in the subject (or a sample thereof) prior to administration of the compositions. In some embodiments, administration of the compositions described herein results in levels of IgE antibodies (e.g., total IgE antibodies or allergen-specific IgE antibodies) that are reduced by at least 1.5-fold, 2-fold, 3-fold, 4-fold, 5-fold, 6-fold, 7-fold, 8-fold, 9-fold, 10-fold, 20-fold, 30-fold, 40-fold, 50-fold, 100-fold, 1000-fold, $10^4$-fold, $10^5$-fold or more, as compared to the level of IgE antibodies in another subject (e.g., a reference subject) who did not receive the compositions.

In some embodiments, administration of the compositions described herein results in levels of IgE antibodies (e.g., total IgE antibodies or allergen-specific IgE antibodies) that are reduced by at least 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%, 95%, or 100% as compared to the level of IgE antibodies (e.g., total IgE antibodies or allergen-specific IgE antibodies) in the subject (or a sample thereof) prior to administration of the compositions. In some embodiments, administration of the compositions described herein results in levels of IgE antibodies (e.g., total IgE antibodies or allergen-specific IgE antibodies) that are reduced by at least 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%, 95%, or 100% as compared to the level of IgE antibodies in another subject (e.g., a reference subject) who did not receive the compositions.

In some embodiments, administration of the compositions described herein results in levels of IgE antibodies (e.g., total IgE antibodies or allergen-specific IgE antibodies) that are reduced by between 30% and 50%, 30% and 45%, 35% and 45%, 30% and 40%, 35% and 40%, 40% and 50%, 40% and 45%, 45% and 50% as compared to the level of IgE antibodies (e.g., total IgE antibodies or allergen-specific IgE antibodies) in the subject (or a sample thereof) prior to administration of the compositions. In some embodiments, administration of the compositions described herein results in levels of IgE antibodies (e.g., total IgE antibodies or allergen-specific IgE antibodies) that are reduced by between 30% and 50%, 30% and 45%, 35% and 45%, 30% and 40%, 35% and 40%, 40% and 50%, 40% and 45%, 45% and 50% as compared to the level of IgE antibodies in another subject (e.g., a reference subject) who did not receive the compositions.

The presence and/or quantity of IgE antibodies in a subject, including the presence and/or quantity of allergen-specific IgE antibodies, can be assessed by methods known in the art. For example, a sample, such as a blood or plasma sample, may be obtained from a subject and subjected to analysis, for example by immunoassays (e.g., radio allergosorbent test (RAST), fluorescent allergosorbant test (FAST), enzyme-linked immunosorbent assays (ELISA)) and protein arrays (see e.g., Fall et al. *Methods Mol Biol* (2009) 509: 107-122). The presence of allergen-specific IgE antibodies may, additionally or alternatively, be assessed using a skin test (e.g., skin prick test).

In some embodiments, the compositions and methods described herein suppress one or more Th2 immune responses. In some embodiments, the compositions and methods described herein suppress the development or differentiation of Th2 cells (also referred to as type 2 helper T cells). In some embodiments, the compositions and methods described herein suppress the activity of Th2 cells. As will be evident by one of ordinary skill in the art, Th2 cells are a subject of CD4+ cells that produce IL-4, IL-5, IL-6, IL-10, and/or IL-13 and may be involved in promoting IgE antibody responses and/or eosinophil activity. The differentiation of CD4+ cells to Th2 cells is promoted by the presence of IL-4 and/or IL-12 and activation of the transcription factors STATE and GATA3 (see, e.g., Wan *Trends Immunol.* (2014) 35(6): 233-242; Zhu et al. *J. Immunol.* (2001) 166: 7276-7281). In some embodiments, the amount of IgE antibodies may be assessed as a marker of Th2 immune responses in a subject.

In some embodiments, administration of the compositions described herein results in levels of Th2 immune responses that are reduced by at least 1.5-fold, 2-fold, 3-fold, 4-fold, 5-fold, 6-fold, 7-fold, 8-fold, 9-fold, 10-fold, 20-fold, 30-fold, 40-fold, 50-fold, 100-fold, 1000-fold, $10^4$-fold, $10^5$-fold or more, as compared to Th2 immune response in the subject (or a sample thereof) prior to administration of the compositions. In some embodiments, administration of the compositions described herein results in Th2 immune responses that are reduced by at least 1.5-fold, 2-fold, 3-fold, 4-fold, 5-fold, 6-fold, 7-fold, 8-fold, 9-fold, 10-fold, 20-fold, 30-fold, 40-fold, 50-fold, 100-fold, 1000-fold, $10^4$-fold, $10^5$-fold or more, as compared to Th2 immune responses in another subject (e.g., a reference subject) who did not receive the compositions.

In some embodiments, administration of the compositions described herein results in levels of Th2 immune responses that are reduced by at least 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%, 95%, or 100%, as compared to Th2 immune response in the subject (or a sample thereof) prior to administration of the compositions. In some embodiments, administration of the compositions described herein results in Th2 immune responses that are reduced by at least 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%, 95%, or 100%, as compared to Th2 immune responses in another subject (e.g., a reference subject) who did not receive the compositions.

The presence or level of a Th2 immune response may be assessed using any method known in the art. The presence or level of a Th2 immune response may be assessed, for example, by detecting and/or quantifying the number of Th2 cells in a sample obtained from the subject, such as by detecting a cellular marker indicative of the Th2 cells; assessing transcription profile associated with Th2 cells; assessing a direct or indirect activity of Th2 cells; and/or by measuring the production of one or more cytokines produced by Th2 cells (e.g., IL-4, IL-5, IL-6, IL-10, IL-13).

In some embodiments, administration of the compositions provided herein results in a healthy microbiome that modulates an immune response associated with allergy (e.g., a food allergy) in a subject. In some embodiments, administration of the compositions provided herein results in a healthy microbiome that modulates an immune response associated with allergy (e.g., a food allergy) in a subject. In some embodiments, administration of the compositions provided herein results in a healthy microbiome that induces the accumulation and/or proliferation of regulatory T cells in a subject. In some embodiments, administration of the compositions provided herein results in a healthy microbiome that suppresses production of IgE antibodies in a subject. In some embodiments, administration of the compositions provided herein results in a healthy microbiome that suppresses Th2 immune responses in a subject.

In some embodiments, the therapeutically effective amount of any of the compositions described herein is an amount sufficient to treat the allergy. In some embodiments, the therapeutically effective amount of any of the compositions described herein is an amount sufficient to reduce one or more symptom associated with the allergy. In some embodiments, the therapeutically effective amount of any of the compositions described herein is an amount sufficient to modulate one or more immune responses associated with allergy, such as a food allergy. For example, in some embodiments, the therapeutically effective amount of any of the compositions described herein is an amount sufficient to induce the proliferation and/or accumulation of regulatory T cells (Tregs) in the subject. In some embodiments, the therapeutically effective amount of the composition induces the proliferation and/or accumulation of Tregs at a particular site (e.g., the gastrointestinal tract) of the subject. In some embodiments, the therapeutically effective amount of any of the compositions described herein is an amount sufficient to suppress the production of IgE antibodies (e.g., total IgE antibodies or allergen-specific IgE antibodies). In some embodiments, the therapeutically effective amount of any of the compositions described herein is an amount sufficient to suppress one or more Th2 immune responses. In some embodiments, the therapeutically effective amount of any of the compositions described herein is an amount sufficient to allow a subject to survive a challenge with the allergen (e.g., in case of an anaphylactic allergic response in the inadvertent exposure to a peanut allergen).

As used herein, the term "therapeutically effective amount" may be used interchangeably with the term "effective amount." A therapeutically effective amount or an effective amount of a composition, such as a pharmaceutical composition, as described herein, is any amount that results in a desired response or outcome in a subject, such as those described herein, including but not limited to delay the manifestation, arrest the progression, relieve or alleviate at least one symptom of the disease that is treated using the methods described herein (e.g., allergy).

It should be appreciated that the term effective amount, in reference to a composition comprising bacterial strains, may be expressed as the number of bacteria or CFUs to be administered. It should further be appreciated that the bacteria can multiply once administered. Thus, administration of even a relatively small amount of bacteria may have therapeutic effects.

Any of the methods described herein may be for the treatment of allergy in a subject. As used herein, methods of treating allergy involve relieving or alleviating at least one symptom associated with the allergy, or slowing or preventing the onset of an allergic reaction upon contact or exposure to an allergen.

Also within the scope of the present disclosure are methods involving determining whether a subject has or is at risk of having an allergy or having an allergic reaction in response to an allergen. In some embodiments, if the subject is determined to have an allergy or be at risk for having an allergic reaction in response to an allergen, the subject is administered any of the compositions containing the bacterial strains described herein. Methods of determining whether a subject has or is at risk of an allergy or having an allergic reaction in response to an allergen are known in the art and include, for example, detecting the presence or a level of IgE antibodies (e.g., total IgE antibodies, allergen-specific IgE antibodies), detecting the presence or a level of one or more Th2 immune response, or performing an allergy skin test. In some embodiments, the methods involve assessing whether the subject has or is at risk of having a food allergy. In some embodiments, if the subject is determined to have a food allergy or be at risk for having an allergic reaction in response to a food allergen, the subject is administered any of the compositions containing the bacterial strains described herein.

Aspects of the disclosure relate to the administration of composition comprising bacterial strains. In some embodiments, the disclosure provides bacterial strains with 16S rDNA sequences that have sequence identity to a nucleic acid sequence of any one of the sequences of the bacterial strains or species described herein. The terms "identical," or percent "identity," in the context of two or more nucleic acids or amino acid sequences, refer to two or more sequences or subsequences that are the same. Two sequences are "substantially identical" if two sequences have a specified percentage of amino acid residues or nucleotides that are the same (e.g., at least 80%, 85%, 90%, 95%, 96%, 97%, 98%, 99%, 99.5%, 99.6%, 99.7%, 99.8% or 99.9% sequence identity) over a specified region of a nucleic acid or amino acid sequence or over the entire sequence, when compared and aligned for maximum correspondence over a comparison window, or designated region as measured using one of the following sequence comparison algorithms or by manual alignment and visual inspection. Optionally, the identity exists over a region that is at least about 50 nucleotides in length, or more preferably over a region that is 100 to 500 or 1000 or more nucleotides in length. In some embodiments, the identity exists over the length the 16S rRNA or 16S rDNA sequence.

In some embodiments, the bacterial strain has at least 60%, at least 70%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or up to 100% sequence identity relative to any of the strains or bacterial species described herein over a specified region or over the entire sequence. It would be appreciated by one of skill in the art that the term "sequence identity" or "percent sequence identity," in the context of two or more nucleic acid sequences or amino acid sequences, refers to a measure of similarity between two or more sequences or portion(s) thereof.

In some embodiments, the composition includes two or more (e.g., 3, 4, 5, 6, 7, 8, 9, 10, 11, 12, 13, 14, 15, 16, 17, 18, 19, or 20) bacterial strains, wherein the two or more bacterial strains contain 16S rDNA sequences having at least 97% sequence identity with nucleic acid sequences selected from SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO: 9, SEQ ID NO: 10, SEQ ID NO: 11, SEQ ID NO: 12, and SEQ ID NO: 13.

In some embodiments, the composition includes two or more (e.g., 3, 4, 5, 6, 7, 8, 9, 10, 11, 12, 13, 14, 15, 16, 17, 18, 19, or 20) bacterial strains, wherein the two or more bacterial strains contain 16S rDNA sequences having at least 97% sequence identity with nucleic acid sequences selected from SEQ ID NO:1, SEQ ID NO:2, SEQ ID NO:3, SEQ ID NO:4, SEQ ID NO:5, SEQ ID NO:6, SEQ ID NO:7, and SEQ ID NO:8. In some embodiments, the composition includes three or more (e.g., 3, 4, 5, 6, 7, 8, 9, 10, 11, 12, 13, 14, 15, 16, 17, 18, 19, or 20) bacterial strains, wherein the two or more bacterial strains contain 16S rDNA sequences having at least 97% sequence identity with nucleic acid sequences selected from SEQ ID NO:1, SEQ ID NO:2, SEQ ID NO:3, SEQ ID NO:4, SEQ ID NO:5, SEQ ID NO:7, and SEQ ID NO:8; and the composition does not contain a bacterial strain having a 16S rDNA sequence with at least 97% sequence identity with the nucleic acid sequence provided by SEQ ID NO: 6. In some embodiments, the composition includes two or more (e.g., 3, 4, 5, 6, 7, 8, 9, 10, 11, 12, 13, 14, 15, 16, 17, 18, 19, or 20) bacterial strains, wherein the two or more bacterial strains contain 16S rDNA sequences having at least 97% sequence identity with nucleic acid sequences selected from SEQ ID NO:1, SEQ ID NO:2, SEQ ID NO:3, SEQ ID NO:4, SEQ ID NO:5, SEQ ID NO:6, and SEQ ID NO:8; and the composition does not contain a bacterial strain having a 16S rDNA sequence with at least 97% sequence identity with the nucleic acid sequence provided by SEQ ID NO: 7.

In some embodiments, the composition includes seven bacterial strains, wherein the bacterial strains include 16S rDNA sequences having at least 97% sequence identity with nucleic acid sequences selected from SEQ ID NO:1, SEQ ID NO:2, SEQ ID NO:3, SEQ ID NO:4, SEQ ID NO:5, SEQ ID NO:7, and SEQ ID NO:8. In some embodiments, the composition includes seven bacterial strains, wherein the bacterial strains include 16S rDNA sequences having at least 97% sequence identity with nucleic acid sequences selected from SEQ ID NO:1, SEQ ID NO:2, SEQ ID NO:3, SEQ ID NO:4, SEQ ID NO:5, SEQ ID NO:6, or SEQ ID NO:8.

In some embodiments, the composition includes bacterial strains having 16S rDNA sequences with at least 97% sequence identity with nucleic acid sequences selected from SEQ ID NO:1, SEQ ID NO:2, SEQ ID NO:3, SEQ ID NO:4, SEQ ID NO:5, SEQ ID NO:7, and SEQ ID NO:8; and one or more additional bacterial strain. In some embodiments, the composition includes seven bacterial strains, wherein the bacterial strains include 16S rDNA sequences having at least 97% sequence identity with nucleic acid sequences selected from SEQ ID NO:1, SEQ ID NO:2, SEQ ID NO:3, SEQ ID NO:4, SEQ ID NO:5, SEQ ID NO:6, or SEQ ID NO:8; and one or more bacterial strain.

In some embodiments, the composition consists of seven bacterial strains having 16S rDNA sequences having at least 97% sequence identity with nucleic acid sequences of SEQ ID NO:1, SEQ ID NO:2, SEQ ID NO:3, SEQ ID NO:4, SEQ ID NO:5, SEQ ID NO:7, and SEQ ID NO:8. In some embodiments, the composition consists of seven bacterial strains having 16S rDNA sequences having at least 97% sequence identity with nucleic acid sequences of SEQ ID NO:1, SEQ ID NO:2, SEQ ID NO:3, SEQ ID NO:4, SEQ ID NO:5, SEQ ID NO:6, or SEQ ID NO:8.

In some embodiments, the composition includes two or more (e.g., 3 or 4) bacterial strains, wherein the two or more bacterial strains contain 16S rDNA sequences having at least 97% sequence identity with nucleic acid sequences selected from SEQ ID NO: 10, SEQ ID NO: 11; SEQ ID NO: 13; and SEQ ID NO: 4. In some embodiments, the composition consists of four bacterial strains, wherein the four bacterial strains contain 16S rDNA sequences having at least 97% sequence identity with nucleic acid sequences set forth as SEQ ID NO: 10, SEQ ID NO: 11; SEQ ID NO: 13; and SEQ ID NO: 4.

In some embodiments, the composition includes two or more (e.g., 3 or 4) bacterial strains, wherein the two or more bacterial strains contain 16S rDNA sequences having at least 97% sequence identity with nucleic acid sequences selected from SEQ ID NO: 9, SEQ ID NO: 1; SEQ ID NO: 3; and SEQ ID NO: 12. In some embodiments, the composition consists of four bacterial strains, wherein the four bacterial strains contain 16S rDNA sequences having at least 97% sequence identity with nucleic acid sequences set forth as SEQ ID NO: 9, SEQ ID NO: 1; SEQ ID NO: 3; and SEQ ID NO: 12.

Additionally, or alternatively, two or more sequences may be assessed for the alignment between the sequences. The terms "alignment" or percent "alignment" in the context of two or more nucleic acids or amino acid sequences, refer to two or more sequences or subsequences that are the same. Two sequences are "substantially aligned" if two sequences have a specified percentage of amino acid residues or nucleotides that are the same (e.g., at least 80%, 85%, 90%, 95%, 96%, 97%, 98%, 99%, 99.5%, 99.6%, 99.7%, 99.8% or 99.9% identical) over a specified region or over the entire sequence, when compared and aligned for maximum correspondence over a comparison window, or designated region as measured using one of the following sequence comparison algorithms or by manual alignment and visual inspection. Optionally, the alignment exists over a region that is at least about 50 nucleotides in length, or more preferably over a region that is 100 to 500 or 1000 or more nucleotides in length. In some embodiments, the identity exists over the length the 16S rRNA or 16S rDNA sequence.

For sequence comparison, typically one sequence acts as a reference sequence, to which test sequences are compared. Methods of alignment of sequences for comparison are well known in the art. See, e.g., by the local homology algorithm of Smith and Waterman (1970) *Adv. Appl. Math.* 2:482c, by the homology alignment algorithm of Needleman and Wunsch, *J. Mol. Biol.* 48:443, 1970, by the search for similarity method of Pearson and Lipman. *Proc. Natl. Acad. Sci. USA* 85:2444, 1988, by computerized implementations of these algorithms (GAP, BESTFIT, FASTA, and TFASTA in the Wisconsin Genetics Software Package, Genetics Computer Group. Madison. Wis.), or by manual alignment and visual inspection (see. e.g., Brent et al., *Current Protocols in Molecular Biology*, John Wiley & Sons, Inc. (Ringbou ed., 2003)). Two examples of algorithms that are suitable for determining percent sequence identity and sequence similarity are the BLAST and BLAST 2.0 algorithms, which are described in Altschul et al., *Nuc. Acids Res.* 25:3389-3402, 1977; and Altschul et al., *J. Mol. Biol.* 215:403-410, 1990, respectively.

It should be appreciated that the terms "bacteria" and "bacterial strains" as used herein are interchangeable. The compositions described herein containing multiple purified bacterial strains may also be referred to as "live bacterial products."

In some embodiments, the compositions described herein contain bacteria belonging to the class Clostridia. In some embodiments, the compositions described herein contain bacteria belonging to the family Clostridiaceae. In some embodiments, the compositions described herein contain bacteria belonging to the genus *Clostridium*. In some embodiments, the compositions described herein contain bacterial strains belonging to *Clostridium* cluster IV, XIVa, and/or XVII. In some embodiments, the compositions contain bacterial strains belonging to *Clostridium* cluster IV, XIVa, and XVII. In some embodiments, the compositions described herein contain bacterial strains belonging to *Clostridium* cluster IV or XIVa. In some embodiments, the compositions described herein do not contain a bacterial strain belonging to *Clostridium* cluster XVII. In some embodiments, the compositions described herein do not contain a bacterial strain belonging to *Clostridium* cluster XVI. In some embodiments, the compositions described herein do not contain a bacterial strain belonging to *Clostridium* cluster XVIII. In some embodiments, the compositions described herein do not contain a bacterial strain belonging to *Clostridium* cluster XVI or XVIII.

In some embodiments, the compositions described herein contain two or more of the following bacterial strains: *Clostridium bolteae, Anaerotruncus colihominis, Sellimonas intestinales, Clostridium symbiosum, Blautia producta, Dorea longicatena*, Erysipelotrichaceae bacterium, *Subdolinogranulum* spp, *Clostridium hathewayi, Clostridium indolis, Anaerostipes caccae*, Lachnospiraceae bacterium, and *Clostridium* species.

In some embodiments, the compositions described herein contain two or more of the following bacterial strains: *Clostridium bolteae, Anaerotruncus colihominis, Sellimonas intestinales, Clostridium symbiosum, Blautia producta, Dorea longicatena*, Erysipelotrichaceae bacterium, and *Subdolinogranulum* spp. In some embodiments, the composition includes two or more (e.g., 3, 4, 5, 6, 7, or 8) of the following bacterial strains: *Clostridium bolteae, Anaerotruncus colihominis, Sellimonas intestinales, Clostridium symbiosum, Blautia producta, Dorea longicat-*

*ena*, Erysipelotrichaceae bacterium, and *Subdolinogranulum* spp. In some embodiments, the composition includes two or more (e.g., 3, 4, 5, 6, 7, or 8) of the following bacterial strains: *Clostridium bolteae, Anaerotruncus colihominis, Sellimonas intestinales, Clostridium symbiosum, Blautia producta, Dorea longicatena*, Erysipelotrichaceae bacterium, and *Subdolinogranulum* spp.; and one or more additional bacterial strain.

In some embodiments, the compositions described herein contain two or more of the following bacterial strains: *Clostridium bolteae, Anaerotruncus colihominis, Sellimonas intestinales, Clostridium symbiosum, Blautia producta*, Erysipelotrichaceae bacterium, and *Subdolinogranulum* spp.; and the composition does not contain *Dorea longicatena*. In some embodiments, the compositions described herein contain two or more of the following bacterial strains: *Clostridium bolteae, Anaerotruncus colihominis, Sellimonas intestinales, Clostridium symbiosum, Blautia producta, Dorea longicatena*, and *Subdolinogranulum* spp.; and the composition does not contain Erysipelotrichaceae bacterium.

In some embodiments, the compositions contain 7 bacterial strains. In some embodiments, the compositions consist of the following bacterial strains: *Clostridium bolteae, Anaerotruncus colihominis, Sellimonas intestinales, Clostridium symbiosum, Blautia producta*, Erysipelotrichaceae bacterium, and *Subdolinogranulum* spp. In some embodiments, the compositions consist of the following bacterial strains: *Clostridium bolteae, Anaerotruncus colihominis, Sellimonas intestinales, Clostridium symbiosum, Blautia producta, Dorea longicatena*, and *Subdolinogranulum* spp.

In some embodiments, the compositions described herein contain two or more (e.g., 3 or 4) of the following bacterial strains: *Clostridium indolis, Anaerostipes caccae*, Lachnospiraceae bacterium, and *Clostridium symbiosum*. In some embodiments, the compositions described herein consist of the following bacterial strains: *Clostridium indolis, Anaerostipes caccae*, Lachnospiraceae bacterium, and *Clostridium symbiosum*.

In some embodiments, the compositions described herein contain two or more (e.g., 3 or 4) of the following bacterial strains: *Clostridium hathewayi, Clostridium bolteae, Sellimonas intestinalis*, and *Clostridium* species. In some embodiments, the compositions described herein consist of the following bacterial strains: *Clostridium hathewayi, Clostridium bolteae, Sellimonas intestinalis*, and *Clostridium* species.

In one aspect, the 16S rDNA sequences of purified bacterial strains were compared to 16S rDNA sequences of known bacterial species/strains in a bacterial genome database to identify the closest known related bacterial species to the bacterial strains disclosed herein. It should be appreciated that multiple bacterial strains of the compositions disclosed herein may have the same closest related bacterial species.

In one aspect, as shown herein (e.g., in the Examples) the compositions and methods provided herein include the following bacteria *Clostridium bolteae, Anaerotruncus colihominis, Sellimonas intestinales, Clostridium symbiosum, Blautia producta, Dorea longicatena*, Erysipelotrichaceae bacterium and *Subdolinogranulum* spp. The exemplary bacterial strains of the compositions disclosed herein can also be identified by their 16S rRNA sequences (SEQ ID NOs: 1-8). Identifying bacteria by their sequences furthermore allows for the identification of additional bacterial strains that are identical or highly similar to the exemplified bacteria. For instance, the 16S rRNA sequences of bacterial strains were used to identify the closest relative (based on percent identity) through whole genome sequencing and by comparing these sequences with 16S databases (Table 1). In addition, based on whole genome sequencing and comparing of the whole genome to whole genome databases, the bacterial strains having 16S rRNA sequences provided by SEQ ID NOs: 1-8 are most closely related to the following bacterial species: *Clostridium bolteae* 90A9, *Anaerotruncus colihominis* DSM 17241, *Dracourtella massiliensis* GD1, *Clostridium symbiosum* WAL-14163, *Clostridium bacterium* UC5.1-1D4, *Dorea longicatena* CAG:42, Erysipelotrichaceae bacterium 21_3, and *Clostridium orbiscindens* 1_3_50AFAA (see, e.g., Table 1). Thus, in one aspect, it should be appreciated that each row of Table 1, the bacterial strains are highly similar and/or are identical. In some embodiments, in context of the instant disclosure the names of bacterial strains within a row of Table 1 can be used interchangeably.

Thus, for example, in some embodiments, the disclosure provides methods and compositions including the following bacteria: *Clostridium bolteae, Anaerotruncus colihominis, Sellimonas intestinalis, Clostridium symbiosum, Blautia producta, Dorea longicatena*, Erysipelotrichaceae bacterium, and *Subdolinogranulum* spp. In some embodiments, the disclosure provides methods and compositions including the following bacteria: *Clostridium bolteae, Anaerotruncus colihominis, Sellimonas intestinalis, Clostridium symbiosum, Blautia producta*, Erysipelotrichaceae bacterium and *Subdolinogranulum* spp. In some embodiments, the disclosure provides methods and compositions including the following bacteria: *Clostridium bolteae, Anaerotruncus colihominis, Sellimonas intestinalis, Clostridium symbiosum, Blautia producta, Dorea longicatena*, and *Subdolinogranulum* spp.

Thus, for example, in some embodiments, the disclosure provides methods and compositions including the following bacteria: *Clostridium bolteae, Anaerotruncus colihominis, Eubacterium fissicatena, Clostridium symbiosum, Blautia producta, Dorea longicatena*, Erysipelotrichaceae bacterium and *Subdolinogranulum* spp. In some embodiments, the disclosure provides methods and compositions including the following bacteria: *Clostridium bolteae, Anaerotruncus colihominis, Eubacterium fissicatena, Clostridium symbiosum, Blautia producta*, Erysipelotrichaceae bacterium, and *Subdolinogranulum* spp. In some embodiments, the disclosure provides methods and compositions including the following bacteria: *Clostridium bolteae, Anaerotruncus colihominis, Eubacterium fissicatena, Clostridium symbiosum, Blautia producta, Dorea longicatena*, and *Subdolinogranulum* spp.

Thus, for example, in some embodiments, the disclosure provides methods and compositions including the following bacteria: *Clostridium bolteae, Anaerotruncus colihominis, Drancourtella massiliensis, Clostridium symbiosum, Blautia producta, Dorea longicatena*, Erysipelotrichaceae bacterium and *Subdolinogranulum* spp. In some embodiments, the disclosure provides methods and compositions including the following bacteria: *Clostridium bolteae, Anaerotruncus colihominis, Drancourtella massiliensis Clostridium symbiosum, Blautia producta*, Erysipelotrichaceae bacterium and *Subdolinogranulum* spp. In some embodiments, the disclosure provides methods and compositions including the following bacteria: *Clostridium bolteae, Anaerotruncus colihominis, Drancourtella massiliensis Clostridium symbiosum, Blautia producta, Dorea longicatena*, and *Subdolinogranulum* spp.

Thus, for example, in some embodiments, the disclosure provides methods and compositions including the following bacteria: *Clostridium bolteae, Anaerotruncus colihominis,* Ruminococcus torques, *Clostridium symbiosum, Blautia producta, Dorea longicatena,* Erysipelotrichaceae bacterium and *Subdolinogranulum* spp. In some embodiments, the disclosure provides methods and compositions including the following bacteria: *Clostridium bolteae, Anaerotruncus colihominis,* Ruminococcus torques, *Clostridium symbiosum, Blautia producta,* Erysipelotrichaceae bacterium and *Subdolinogranulum* spp. In some embodiments, the disclosure provides methods and compositions including the following bacteria: *Clostridium bolteae, Anaerotruncus colihominis,* Ruminococcus torques, *Clostridium symbiosum, Blautia producta, Dorea longicatena,* and *Subdolinogranulum* spp.

Thus, for example, in some embodiments, the disclosure provides methods and compositions including the following bacteria: *Clostridium bolteae, Anaerotruncus colihominis,* Ruminococcus torques, *Clostridium symbiosum, Blautia producta, Dorea longicatena,* Erysipelotrichaceae bacterium, and *Clostridium orbiscindens* In some embodiments, the disclosure provides methods and compositions including the following bacteria: *Clostridium bolteae, Anaerotruncus colihominis,* Ruminococcus torques, *Clostridium symbiosum, Blautia producta,* Erysipelotrichaceae bacterium, and *Clostridium orbiscindens.* In some embodiments, the disclosure provides methods and compositions including the following bacteria: *Clostridium bolteae, Anaerotruncus colihominis,* Ruminococcus torques, *Clostridium symbiosum, Blautia producta, Dorea longicatena,* and *Clostridium orbiscindens.*

Homologies based on whole genome analysis are presented in Table 1.

TABLE 1

Bacterial strains in Composition B

| Strain number | SEQ ID NO: | Closest species based on Sanger sequencing of 16S region | Closest species based on Consensus SEQ ID # of 16S region as compared with 16S database | Closest species based on WGS compared versus WG databases | Additional closely related sequences | *Clostridium* cluster |
|---|---|---|---|---|---|---|
| 1 | 1 | *Clostridium bolteae* | *Clostridium bolteae* | *Clostridium bolteae* 90A9 | | XIVa |
| 2 | 2 | *Anaerotruncus colihominis* | *Anaerotruncus colihominis* | *Anaerotruncus colihominis* DSM 17241 | | IV |
| 3 | 3 | *Eubacterium fissicatena* | *Dracourtella massiliensis* | *Dracourtella massiliensis* GD1 | *Ruminococcus torques; Sellimonas intestinalis* | XIVa |
| 4 | 4 | *Clostridium symbiosum* | *Clostridium symbiosum* | *Clostridium symbiosum* WAL-14163 | | XIVa |
| 5 | 5 | *Blautia producta* | *Blautia producta* | *Clostridium* bacterium UC5.1-1D4 | *Blautia* product ATCC 27340 | XIVa |
| 6 | 6 | *Dorea longicatena* | *Dorea longicatena* | *Dorea longicatena* CAG: 42 | | XIVa |
| 7 | 7 | *Clostridium innocuum* | *Clostridium innocuum* | Erysipelotrichaceae bacterium 21_3 | | XVII |
| 8 | 8 | *Flavinofractor plautii* | *Flavinofractor plautii* | *Clostridium orbiscindens* 1_3_50AFAA | *Subdolinogranulum* | IV |

Thus, for example, in some embodiments, the disclosure provides methods and compositions including the following bacteria: *Clostridium bolteae, Anaerotruncus colihominis,* Ruminococcus torques, *Clostridium symbiosum, Blautia producta, Dorea longicatena, Clostridium innocuum,* and *Subdolinogranulum* spp. In some embodiments, the disclosure provides methods and compositions including the following bacteria: *Clostridium bolteae, Anaerotruncus colihominis,* Ruminococcus torques, *Clostridium symbiosum, Blautia producta, Clostridium innocuum,* and *Subdolinogranulum* spp.

Thus, for example, in some embodiments, the disclosure provides methods and compositions including the following bacteria: *Clostridium bolteae, Anaerotruncus colihominis,* Ruminococcus torques, *Clostridium symbiosum, Blautia producta, Dorea longicatena,* Erysipelotrichaceae bacterium, and *Flavinofractor plautii.* In some embodiments, the disclosure provides methods and compositions including the following bacteria: *Clostridium bolteae, Anaerotruncus colihominis,* Ruminococcus torques, *Clostridium symbiosum, Blautia producta,* Erysipelotrichaceae bacterium, and *Flavinofractor plautii.* In some embodiments, the disclosure provides methods and compositions including the following bacteria: *Clostridium bolteae, Anaerotruncus colihominis,* Ruminococcus torques, *Clostridium symbiosum, Blautia producta, Dorea longicatena,* and *Flavinofractor plautii.*

Thus, for example, in some embodiments, the disclosure provides methods and compositions including the following In some embodiments, one or more of the bacterial strains are human-derived bacteria, meaning the one or more bacterial strains were obtained from or identified from a human or a sample therefrom (e.g., a human donor). In some embodiments, the one or more bacterial strains are human commensal bacteria, i.e., bacterial strains commonly found in a healthy human microbiome. In some embodiments of the compositions provided herein, all of the bacterial strains are human-derived bacteria. In some embodiments of the compositions provided herein, all of the bacterial strains are human commensal bacteria. In some embodiments of the compositions provided herein, the bacterial strains are derived from more than one human donor.

The bacterial strains used in the compositions provided herein generally are isolated from the microbiome of healthy individuals. In some embodiments, the compositions include strains originating from a single individual. In some embodiments, the compositions include strains originating from multiple individuals. In some embodiments, the compositions are obtained from multiple individuals, isolated, and grown up individually. The bacterial compositions that are grown up individually may subsequently be combined to provide the compositions of the disclosure. It should be appreciated that the origin of the bacterial strains of the compositions provided herein is not limited to the human microbiome from a healthy individual. In some embodiments, the bacterial strains originate from a human with a microbiome in dysbiosis. In some embodiments, the bacterial strains originate from non-human animals or the environment (e.g., soil or surface water). In some embodiments, the combinations of bacterial strains provided herein originate from multiple sources (e.g., human and non-human animals).

In some embodiments, the composition includes one or more anaerobic bacteria. In some embodiments, the composition includes only anaerobic bacteria. In some embodiments, the composition includes one or more facultative anaerobic bacteria. In some embodiments, the composition includes only facultative anaerobic bacteria. In some embodiments, the composition includes one or more obligate anaerobic bacteria. In some embodiments, the composition includes only obligate anaerobic bacteria.

In some embodiments, at least one (e.g., 1, 2, 3, 4, 5, or more) of the bacterial strains in the composition is a spore former. In some embodiments, at least one (e.g., 1, 2, 3, 4, 5, or more) of the bacterial strains in the composition is in spore form. In some embodiments, at least one (e.g., 1, 2, 3, 4, 5, or more) of the bacterial strains in the composition is a non-spore former. In some embodiments, at least one (e.g., 1, 2, 3, 4, 5, or more) of the bacterial strains in the composition is in vegetative form. As discussed above, spore forming bacteria can also be in vegetative form. In some embodiments, at least one (e.g., 1, 2, 3, 4, 5, or more) of the bacterial strains in the composition is in spore form and at least one (e.g., 1, 2, 3, 4, 5, or more) of the bacterial strains in the composition is in vegetative form. In some embodiments, at least one bacterial strain that is considered able to form spores (i.e., a spore-former) but is present in the composition in vegetative form. In some embodiments, at least one bacterial strain that is considered able to form spores is present in the composition both in spore form and in vegetative form.

It is envisioned that the bacterial strains of the live bacterial products provided herein are alive and will be alive when they reach the target area (e.g., the intestines). Bacterial spores are considered to be alive in this regard. In some embodiments, bacteria that are administered as spores may germinate in the target area (e.g., the intestines). It should further be appreciated that not all of the bacteria are alive and the compositions can include a percentage (e.g., by weight) that is not alive. In addition, in some embodiments, the compositions include bacterial strains that are not alive when administered or at the time when the composition reaches the target area (e.g., the intestines). It is envisioned that non-living bacteria may still be useful by providing some nutrients and metabolites for the other bacterial strains in the composition.

In any of the live bacterial products provided herein, in some embodiments, the bacterial strains are purified. In any of the live bacterial products provided herein, in some embodiments, the bacterial strains are isolated. Any of the bacterial strains described herein may be isolated and/or purified, for example, from a source such as a culture or a microbiota sample (e.g., fecal matter). The bacterial strains used in the compositions provided herein generally are isolated from the microbiome of healthy individuals. However, bacterial strains can also be isolated from individuals that are considered not to be healthy. In some embodiments, the compositions include strains originating from multiple individuals. As used herein, the term "isolated" in the bacteria refers to bacteria that have been separated from one or more undesired component, such as another bacterium or bacterial strain, one or more component of a growth medium, and/or one or more component of a sample, such as a fecal sample. In some embodiments, the bacteria are substantially isolated from a source such that other components of the source are not detected (e.g., below the level of detection). As also used herein, the term "purified" refers to a bacterial strain or composition comprising such that has been separated from one or more components, such as contaminants. In some embodiments, the bacterial strain is substantially free of contaminants. In some embodiments, one or more bacterial strains of a composition may be independently purified from one or more other bacteria produced and/or present in a culture or a sample containing the bacterial strain. In some embodiments, a bacterial strain is isolated or purified from a sample and then cultured under the appropriate conditions for bacterial replication, e.g., under anaerobic culture conditions. The bacteria that is grown under appropriate conditions for bacterial replication can subsequently be isolated/purified from the culture in which it is grown.

Also within the scope of the present disclosure are compositions, e.g., compositions for administering to a subject, such as pharmaceutical compositions. In some embodiments, the composition comprises any of the bacterial strains described herein.

In one aspect, the disclosure provides pharmaceutical compositions comprising any of the bacterial strains described herein. In some embodiments, the pharmaceutical composition comprises a pharmaceutical acceptable excipient. In some embodiments, the pharmaceutical composition is formulated for oral administration. In some embodiments, the pharmaceutical composition is formulated for rectal administration. In some embodiments, the pharmaceutical composition is formulated for delivery to the intestine. In some embodiments, the pharmaceutical composition is formulated for delivery to the colon.

In some embodiments, the composition or pharmaceutical composition contain bacterial strains. In some embodiments, the pharmaceutical compositions contain bacterial strains that are in powder form. In some embodiments, the pharmaceutical compositions contain bacterial strains that are lyophilized. In some embodiments, the pharmaceutical compositions contain bacterial strains that are spray-dried. In some embodiments, the pharmaceutical compositions contain bacterial strains that are lyophilized and bacterial strains that are spray-dried. In some embodiments, the pharmaceutical composition is in the form of a capsule. In some embodiments, the pharmaceutical composition further comprises a pH sensitive composition comprising one or more enteric polymers.

In some embodiments, one or more of the bacterial strains of the compositions, including pharmaceutical compositions and food products, has been spray-dried. In some embodiments, a subset of the bacterial strains is spray-dried. The process of spray-drying refers to production of dry powder from a liquid comprising bacterial compositions. (See, e.g., Ledet et al., Spray-Drying of Pharmaceuticals in "Lyophilized Biologics and Vaccines" pages 273-297, Springer, 2015). In general, the process involves rapidly drying the bacterial compositions with a hot gas. A bacterial strain may be combined with a pharmaceutical excipient prior to combining it with the other bacterial strains or multiple spray-dried bacterial strains may be combined while in spray-dried form and the mixture of bacterial strains, once combined may be subsequently be combined with a pharmaceutical excipient.

Any of the compositions described herein, including the pharmaceutical compositions and food products comprising bacterial strains, the bacterial strains in any form, for example in an aqueous form, such as a solution or a suspension, embedded in a semi-solid form, in a powdered form, or freeze-dried form. In some embodiments, the composition or the bacterial strains are lyophilized. In some embodiments, a subset of the bacterial strains is lyophilized. Methods of lyophilizing compositions, specifically compositions comprising bacteria, are well known in the art. See, e.g., U.S. Pat. Nos. 3,261,761; 4,205,132; PCT Publications WO 2014/029578 and WO 2012/098358, herein incorporated by reference in their entirety. The bacteria may be lyophilized as a combination and/or the bacteria may be lyophilized separately and combined prior to administration. A bacterial strain may be combined with a pharmaceutical excipient prior to combining it with the other bacterial strains or multiple lyophilized bacteria may be combined while in lyophilized form and the mixture of bacteria, once combined may be subsequently be combined with a pharmaceutical excipient. In some embodiments, the bacterial strain is a lyophilized cake. In some embodiments, the compositions comprising the one or more bacterial strains are a lyophilized cake.

The bacterial strains can be manufactured using fermentation techniques well known in the art. In some embodiments, the bacteria are propagated or manufactured using anaerobic fermenters, which can support the rapid growth of anaerobic bacterial species. The anaerobic fermenters may be, for example, stirred tank reactors or disposable wave bioreactors. Culture media such as BL media and EG media, or similar versions of these media devoid of animal components, can be used to support the growth of the bacterial species. The bacterial product can be purified and concentrated from the fermentation broth by traditional techniques, such as centrifugation and filtration, and can optionally be dried and lyophilized by techniques well known in the art.

In some embodiments, the live bacterial product may be formulated for administration as a pharmaceutical composition. The term "pharmaceutical composition" as used herein means a product that results from the mixing or combining of at least one active ingredient, such as any of the bacterial strains described herein, and one or more inactive ingredients, which may include one or more pharmaceutically acceptable excipient.

An "acceptable" excipient refers to an excipient that must be compatible with the active ingredient and not deleterious to the subject to which it is administered. In some embodiments, the pharmaceutically acceptable excipient is selected based on the intended route of administration of the composition, for example a composition for oral or nasal administration may comprise a different pharmaceutically acceptable excipient than a composition for rectal administration. Examples of excipients include sterile water, physiological saline, solvent, a base material, an emulsifier, a suspending agent, a surfactant, a stabilizer, a flavoring agent, an aromatic, an excipient, a vehicle, a preservative, a binder, a diluent, a tonicity adjusting agent, a soothing agent, a bulking agent, a disintegrating agent, a buffer agent, a coating agent, a lubricant, a colorant, a sweetener, a thickening agent, and a solubilizer.

Pharmaceutical compositions of the invention can be prepared in accordance with methods well known and routinely practiced in the art (see e.g., Remington: The Science and Practice of Pharmacy, Mack Publishing Co. 20th ed. 2000). The pharmaceutical compositions described herein may further comprise any carriers or stabilizers in the form of a lyophilized formulation or an aqueous solution. Acceptable excipients, carriers, or stabilizers may include, for example, buffers, antioxidants, preservatives, polymers, chelating reagents, and/or surfactants. Pharmaceutical compositions are preferably manufactured under GMP conditions. The pharmaceutical compositions can be used orally, nasally or parenterally, for instance, in the form of capsules, tablets, pills, sachets, liquids, powders, granules, fine granules, film-coated preparations, pellets, troches, sublingual preparations, chewables, buccal preparations, pastes, syrups, suspensions, elixirs, emulsions, liniments, ointments, plasters, cataplasms, transdermal absorption systems, lotions, inhalations, aerosols, injections, suppositories, and the like. In some embodiments, the pharmaceutical compositions can be used by injection, such as by intravenous, intramuscular, subcutaneous, or intradermal administration.

In some embodiments, the compositions comprising bacterial strains are formulated for delivery to the intestines (e.g., the small intestine and/or the colon). In some embodiments, the composition comprising bacterial strains may be formulated with an enteric coating that increases the survival of the bacteria through the harsh environment in the stomach. The enteric coating is one which resists the action of gastric juices in the stomach so that the bacteria of the composition therein will pass through the stomach and into the intestines. The enteric coating may readily dissolve when in contact with intestinal fluids, so that the bacteria enclosed in the coating will be released in the intestinal tract. Enteric coatings may consist of polymers and copolymers well known in the art, such as commercially available EUDRAGIT (Evonik Industries). (See e.g., Zhang, AAPS Pharm Sci Tech, 2016, 17 (1), 56-67).

The compositions comprising bacterial strains may also be formulated for rectal delivery to the intestine (e.g., the colon). Thus, in some embodiments, compositions comprising bacterial strains may be formulated for delivery by suppository, colonoscopy, endoscopy, sigmoidoscopy or enema. A pharmaceutical preparation or formulation and particularly a pharmaceutical preparation for oral administration, may include an additional component that enables efficient delivery of the compositions of the disclosure to the intestine (e.g., the colon). A variety of pharmaceutical preparations that allow for the delivery of the compositions to the intestine (e.g., the colon) can be used. Examples thereof include pH sensitive compositions, more specifically, buffered sachet formulations or enteric polymers that release their contents when the pH becomes alkaline after the enteric polymers pass through the stomach. When a pH sensitive composition is used for formulating the pharmaceutical preparation, the pH sensitive composition is preferably a polymer whose pH threshold of the decomposition of the composition is between about 6.8 and about 7.5. Such a numeric value range is a range in which the pH shifts toward the alkaline side at a distal portion of the stomach, and hence is a suitable range for use in the delivery to the colon. It should further be appreciated that each part of the intestine (e.g., the duodenum, jejunum, ileum, cecum, colon and rectum), has different biochemical and chemical environment. For instance, parts of the intestines have different pHs, allowing for targeted delivery by compositions that have a specific pH sensitivity. Thus, the compositions provided herein may be formulated for delivery to the intestine or specific parts of the intestine (e.g., the duodenum, jejunum, ileum, cecum, colon and rectum) by providing formulations with the appropriate pH sensitivity. (See e.g., Villena et al., *Int J Pharm* 2015, 487 (1-2): 314-9).

Also within the scope of the present disclosure are pharmaceutical compositions for administration by additional or alternative routes. In some embodiments, the pharmaceutical compositions are formulated for sublingual administration. In some embodiments, the pharmaceutical compositions are formulated for administration by injection.

In some embodiments, a pharmaceutical composition may include an additional component that enables efficient delivery of the compositions of the disclosure to a desired site, such as the gastrointestinal tract (e.g., the colon).

In some embodiments, the pharmaceutical composition includes an adjuvant associated with providing a benefit in the treatment of allergy. In some embodiments, the pharmaceutical composition includes one or more components of an oral immunotherapeutic, an epicutaneous immunotherapeutic, or a sublingual immunotherapeutic.

Another embodiment of a pharmaceutical preparation useful for delivery of the compositions to the intestine (e.g., the colon) is one that ensures the delivery to the colon by delaying the release of the contents (e.g., the bacterial strains) by approximately 3 to 5 hours, which corresponds to the small intestinal transit time. In one embodiment of a pharmaceutical preparation for delayed release, a hydrogel is used as a shell. The hydrogel is hydrated and swells upon contact with gastrointestinal fluid, with the result that the contents are effectively released (released predominantly in the colon). Delayed release dosage units include drug-containing compositions having a material which coats or selectively coats a drug or active ingredient to be administered. Examples of such a selective coating material include in vivo degradable polymers, gradually hydrolyzable polymers, gradually water-soluble polymers, and/or enzyme degradable polymers. A wide variety of coating materials for efficiently delaying the release is available and includes, for example, cellulose-based polymers such as hydroxypropyl cellulose, acrylic acid polymers and copolymers such as methacrylic acid polymers and copolymers, and vinyl polymers and copolymers such as polyvinylpyrrolidone.

Additional examples of pharmaceutical compositions that allow for the delivery to the intestine (e.g., the colon) include bioadhesive compositions which specifically adhere to the colonic mucosal membrane (for example, a polymer described in the specification of U.S. Pat. No. 6,368,586) and compositions into which a protease inhibitor is incorporated for protecting particularly a biopharmaceutical preparation in the gastrointestinal tracts from decomposition due to an activity of a protease.

Another example of a system enabling the delivery to the intestine (e.g., the colon) is a system of delivering a composition to the colon by pressure change in such a way that the contents are released by utilizing pressure change caused by generation of gas in bacterial fermentation at a distal portion of the stomach. Such a system is not particularly limited, and a more specific example thereof is a capsule which has contents dispersed in a suppository base and which is coated with a hydrophobic polymer (for example, ethyl cellulose).

A further example of a system enabling the delivery of a composition to the intestine (e.g., the colon), is a composition that includes a coating that can be removed by an enzyme present in the gut (e.g., the colon), such as, for example, a carbohydrate hydrolase or a carbohydrate reductase. Such a system is not particularly limited, and more specific examples thereof include systems which use food components such as non-starch polysaccharides, amylose, xanthan gum, and azopolymers.

The compositions provided herein can also be delivered to specific target areas, such as the intestine, by delivery through an orifice (e.g., a nasal tube) or through surgery. In addition, the compositions provided herein that are formulated for delivery to a specific area (e.g., the cecum or the colon), may be administered by a tube (e.g., directly into the small intestine). Combining mechanical delivery methods such as tubes with chemical delivery methods such as pH specific coatings, allow for the delivery of the compositions provided herein to a desired target area (e.g., the cecum or the colon).

The compositions comprising bacterial are formulated into pharmaceutically acceptable dosage forms by conventional methods known to those of skill in the art. Dosage regimens are adjusted to provide the optimum desired response (e.g., the prophylactic or therapeutic effect). In some embodiments, the dosage form of the composition is a tablet, pill, capsule, powder, granules, solution, or suppository. In some embodiments, the pharmaceutical composition is formulated for oral administration. In some embodiments, the pharmaceutical composition comprises bacterial strains and is formulated such that the bacteria, or a portion thereof, remain viable after passage through the stomach of the subject. In some embodiments, the pharmaceutical composition is formulated for rectal administration, e.g., as a suppository. In some embodiments, the pharmaceutical composition is formulated for delivery to the intestine or a specific area of the intestine (e.g., the colon) by providing an appropriate coating (e.g., a pH specific coating, a coating that can be degraded by target area specific enzymes, or a coating that can bind to receptors that are present in a target area).

Dosages of the active ingredients in the pharmaceutical compositions of the present invention can be varied so as to obtain an amount of the active ingredient which is effective to achieve the desired pharmaceutical response for a particular subject, composition, and mode of administration, without being toxic or having an adverse effect on the subject. The selected dosage level depends upon a variety of factors including the activity of the particular compositions of the present invention employed, the route of administration, the time of administration, the duration of the treatment, other drugs, compounds and/or materials used in combination with the particular compositions employed, the age, sex, weight, condition, general health and prior medical history of the subject being treated, and like factors.

A physician, veterinarian or other trained practitioner, can start doses of the pharmaceutical composition at levels lower than that required to achieve the desired therapeutic effect and gradually increase the dosage until the desired effect (e.g., treatment of allergy, modulation of one or more immune responses associated with allergy) is achieved. In general, effective doses of the compositions of the present invention, for the prophylactic treatment of groups of people as described herein vary depending upon many different factors, including routes of administration, physiological state of the subject, whether the subject is human or an animal, other medications administered, and the therapeutic effect desired. Dosages need to be titrated to optimize safety and efficacy.

In some embodiments, the dosing regimen entails oral administration of a dose of any of the compositions described herein. In some embodiments, the dosing regimen entails oral administration of multiple doses of any of the compositions described herein. In some embodiments, any of the compositions described herein are administered the subject once, twice, 3 times, 4 times, 5 times, 6 times, 7 times, 8 times, 9 times, or at least 10 times, or more. In some embodiments, any of the compositions described herein are administered the subject in multiple doses at a regular interval, such as every 2 weeks, every month, every 2 months, every 3 months, every 4 months, every 5 months, every 6 months, or more. In some embodiments, one dose of any of the compositions described herein is administered and a second dose of the composition is administered the following day (e.g., consecutive day). In some embodiments, one dose of any of the compositions described herein is administered and each of the additional doses of the composition are administered on consecutive days (e.g., first dose on day 1, second dose of day 2, third dose on day 3, etc.).

In one aspect, the disclosure provides methods comprising administration of multiple daily doses of the pharmaceutical compositions. In some embodiments, the pharmaceutical compositions are administered on a daily basis for 2 days, 3 days, 4, days, 5, days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 1 month, 2 months, 3 months, 4 months, 5 months, 6 months, 7 months, 8 months, 9 months, 10 months, 11 months, 12 months or more.

In some embodiments, the disclosure provides methods comprising administration of one or more doses of the pharmaceutical compositions to a subject, determining if the subject is responding to the administration of the one or more doses of the pharmaceutical compositions, e.g., by measuring the level of Treg cells, IgE cells or doing a skin test, wherein if the response is not associated with the desired effect (e.g., insufficient levels of Treg cell, or a strong response to a skin test), additional doses of the pharmaceutical compositions are administered.

In any of the methods described herein, one or more antibiotics may be administered to the subject prior to administration of any of the bacterial compositions described herein. In some embodiments, the one or more antibiotics are administered to remove from the gastrointestinal tract of the subject bacterial strains that are associated with food allergy (See e.g., Ho et al., Role of the Microbiome in Food Allergy. *Curr Allergy Asthma Rep.* 2018 Apr. 5; 18(4):27.) In some embodiments, the one or more antibiotics are administered to remove from the gastrointestinal tract of the subject bacterial strains that are associated with an undesired immune response that may enhance an allergic response. In such embodiments, the antibiotic will be administered according to a regimen that does not dampen the impact of the beneficial bacterial compositions provided herein (e.g., by letting the antibiotic clear the body prior to administration of the one or more beneficial bacterial compositions provided herein). In some embodiments, one or more antibiotics may be administered to the subject prior to any of the bacterial compositions provided herein. In some embodiments, the disclosure provides methods comprising administration of an antibiotic (e.g., vancomycin) followed by a single dose of the pharmaceutical compositions. In some embodiments, the disclosure provides methods comprising administration of an antibiotic (e.g., vancomycin) followed by multiple doses of the pharmaceutical compositions.

In some embodiments, administration of an antibiotic (e.g., vancomycin) followed by the administration of a single or multiples doses of the pharmaceutical compositions results in an increase in the abundance of bacterial strains of the pharmaceutical composition as compared to methods of administration that do not include the antibiotic. In some embodiments, administration of an antibiotic (e.g., vancomycin) followed by the administration of a single or multiples doses of the pharmaceutical compositions results in an increase in the duration of the colonization of bacterial strains of the pharmaceutical composition as compared to methods of administration that do not include the antibiotic. In some embodiments, the methods described herein do not involve administering an antibiotic prior to the pharmaceutical compositions described herein.

In some embodiments, the antibiotic is vancomycin, fidaxomycin or ridinilazole. In some embodiments, the antibiotic is not vancomycin. Non-limiting examples of antibiotics that may be used in any of the methods provided herein include cephalosporin antibiotics cephalexin, cefuroxime, cefadroxil, cefazolin, cephalothin, cefaclor, cefamandole, cefoxitin, cefprozil, ceftobiprole, clindamycin, ceftriaxone, cefotaxime, cefazolin, cefoperazone, cefuroxime, cefmetazole, fluoroquinolone, ciprofloxacin, Levaquin, floxin, tequin, avelox, norflox, tetracycline, minocycline, oxytetracycline, doxycycline, amoxicillin, ampicillin, penicillin V, dicloxacillin, benzylpenicillin, carbenicillin, vancomycin, and methicillin), ertapenem, doripenem, imipenem/cilastatin, meropenem, clavulanate, tazobactam, piperacillin, ceftriaxone, cefotaxime, cefazolin, fluoroquinolone, imipenem, meropenem, metronidazole, fidaxomyxin or ridinilazole.

In some embodiments, any of the methods described herein may further comprise administering vancomycin to the subject prior to administration of the pharmaceutical compositions described herein. In some embodiments, the method does not comprise administering vancomycin to the subject prior to administration of the pharmaceutical compositions described herein. Vancomycin administration has been found to alter the composition of human gut microbiota. See, e.g., Reijnders et al. *Cell Metabolism* (2016) 24(1): 63-72. Without wishing to be bound by any particular theory, it is thought that administration of vancomycin may aid engraftment of the bacterial strain(s) of the pharmaceutical compositions described herein, for example by removing other microbes present in the gastrointestinal tract.

In some embodiments, the antibiotic (e.g., vancomycin) is administered to the subject once, as a single dose. In some embodiments, the antibiotic (e.g., vancomycin) is administered to the subject in multiple doses. In some embodiments, the antibiotic (e.g., vancomycin) is administered to the subject in at least 2, 3, 4, 5, 6, 7, 8, 9, 10, 11, 12, 13, 14, 15 or more doses. The multiple doses of the antibiotic (e.g., vancomycin) may be administered to the subject at regular intervals prior to administering any of the pharmaceutical compositions described herein. In some embodiments, each of the multiple doses of the antibiotic (e.g., vancomycin) are administered on consecutive days (e.g., first dose on day 1, second dose of day 2, third dose on day 3, etc.). In some embodiments, the antibiotic (e.g., vancomycin) is administered to the subject for 2, 3, 4, 5, 6, 7, 8, 9, 10, 11, 12, 13, 14, 15, or more consecutive days. In some embodiments, the antibiotic (e.g., vancomycin) is administered to the subject each day for three consecutive days. In some embodiments, the antibiotic (e.g., vancomycin) administered to the subject each day for five consecutive days. In some embodiments, the antibiotic (e.g., vancomycin) administered to the subject for one day. In any of the embodiments described herein, a subject may be administered one or more doses of a first antibiotic followed by one or more doses of a second antibiotic.

In some embodiments, a single dose, or the first dose in a treatment regimen of multiple doses, is administered, the same day as the administration of the final dose of the antibiotic (e.g., vancomycin). In some embodiments, a single dose, or the first dose in a treatment regimen of multiple doses, is administered, the day after administration of the final dose of the antibiotic (e.g., vancomycin). In some embodiments, a single dose, or the first dose in a treatment regimen of multiple doses, is administered, two days after administration of the final dose of the antibiotic (e.g., vancomycin). In some embodiments, the methods provided herein allow for a wash out day between the final dose of the antibiotic (e.g., vancomycin) and the first dose of the pharmaceutical composition. In some embodiments, a single dose, or the first dose in a treatment regimen of multiple doses, is administered, three days, four days, five days, six days, ten days or more, after administration of the final dose of the antibiotic (e.g., vancomycin). In some embodiments, the methods provided herein allow for multiple wash out days between the final dose of the antibiotic (e.g., vancomycin) and the first dose of the pharmaceutical composition.

Each dose of the antibiotic (e.g., vancomycin) may be the same amount of the antibiotic or may be a different amount of the antibiotic. In some embodiments, the antibiotic (e.g., vancomycin) is administered in an amount sufficient to allow for colonization of one or more of the bacterial strains of the pharmaceutical compositions described herein. In some embodiments, the subject is administered between about 50 mg and 1 g, 100 mg and 750 mg, 100 mg and 500 mg, 200 mg and 750 mg, 200 mg and 500 mg, 300 mg and 750 mg, 300 mg and 500 mg, 100 mg and 400 mg, 100 mg and 300 mg, 100 mg and 200 mg, 200 mg and 400 mg, 200 mg and 300 mg, or 450 mg to 550 mg of the antibiotic per day. As will be appreciated by one of skill in the art, the total amount of vancomycin administered to the subject per day may be administered in a single dose or between multiple doses, which in sum results in the total amount of the antibiotic per day.

In some example, the subject is administered about 500 mg vancomycin per day prior to administration of any of the pharmaceutical compositions described herein. In some embodiments, 500 mg of vancomycin per day is administered in a single dose (e.g., 500 mg). In some embodiments, 500 mg of vancomycin per day is administered in multiple doses (e.g., 2, 3, 4, 5 or more), which in sum results in 500 mg vancomycin per day. In some embodiments, 500 mg vancomycin is administered in 4 doses of 125 mg vancomycin per day. In some embodiments, 500 mg of vancomycin is administered to the subject for one day. In some embodiments, 500 mg of vancomycin is administered to the subject per day for two days. In some embodiments, 500 mg vancomycin is administered to the subject per day for three days. In some embodiments, 500 mg vancomycin is administered to the subject per day for four days. In some embodiments, 500 mg vancomycin is administered to the subject per day for five days. In some embodiments, the subject is administered about 250 mg vancomycin per day prior to administration of any of the pharmaceutical compositions described herein. In some embodiments, 250 mg vancomycin per day is administered in a single dose (e.g., 250 mg). In some embodiments, 250 mg vancomycin per day is administered in multiple doses (e.g., 2, 3, 4, 5 or more), which in sum results in 250 mg vancomycin per day. In some embodiments, 250 mg vancomycin is administered in 2 doses of 125 mg vancomycin per day. In some embodiments, 250 mg vancomycin is administered to the subject for one day. In some embodiments, 250 mg vancomycin is administered to the subject per day for two days. In some embodiments, 250 mg vancomycin is administered to the subject per day for three days. In some embodiments, 250 mg vancomycin is administered to the subject per day for four days. In some embodiments, 250 mg vancomycin is administered to the subject per day for five days.

In some embodiments, the subject is administered about 125 mg vancomycin per day prior to administration of any of the pharmaceutical compositions described herein. In some embodiments, the 125 mg vancomycin per day is administered in a single dose (e.g., 125 mg). In some embodiments, the 125 mg vancomycin per day is administered in multiple doses (e.g., 2, 3, 4, 5 or more), which in sum results in 125 mg vancomycin per day. In some embodiments, 125 mg vancomycin is administered to the subject for one day. In some embodiments, 125 mg vancomycin is administered to the subject per day for two days. In some embodiments, 125 mg vancomycin is administered to the subject per day for three days. In some embodiments, 125 mg vancomycin is administered to the subject per day for four days. In some embodiments, 125 mg vancomycin is administered to the subject per day for five days.

In some embodiments, the disclosure provides methods comprising administering one or more antibiotics to the subject and subsequently administering any of the bacterial compositions to the subject once, twice, 3 times, 4 times, 5 times, 6 times, 7 times, 8 times, 9 times, or at least 10 times, or more. In some embodiments, the disclosure provides methods comprising administering one or more antibiotics to the subject and subsequently administering any of the bacterial compositions described herein to the subject in multiple doses at a regular interval, such as every 2 weeks, every month, every 2 months, every 3 months, every 4 months, every 5 months, every 6 months, or more. In some embodiments, one dose of any of the compositions described herein is administered and a second dose of the composition is administered the following day (e.g., consecutive day). In some embodiments, one dose of any of the compositions described herein is administered and each of the additional doses of the composition are administered on consecutive days (e.g., first dose on day 1, second dose of day 2, third dose on day 3, etc.).

In one aspect, the disclosure provides methods comprising administering one or more antibiotics to the subject and subsequently administering any of the bacterial compositions as multiple daily doses of the pharmaceutical compositions. In some embodiments, the pharmaceutical compositions are administered on a daily basis for 2 days, 3 days, 4, days, 5, days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 1 month, 2 months, 3 months, 4 months, 5 months, 6 months, 7 months, 8 months, 9 months, 10 months, 11 months, 12 months or more.

Without wishing to be bound by any particular mechanism, in some embodiments, administration of the pharmaceutical compositions described herein may treat or reduce the incidence of or severity of allergy by inducing an immune response in the subject (e.g., regulatory T cells, suppression of IgE antibodies). In some embodiments, administration of the pharmaceutical compositions described herein may treat or reduce the incidence of or severity of allergy by modifying the microbiome of the subject. In some embodiments, administration of the pharmaceutical compositions described herein may treat or reduce the incidence of or severity of allergy by increasing the presence or abundance of bacterial strains of the pharmaceutical compositions in the microbiome of the subject. In some embodiments, administration of the pharmaceutical compositions described herein may treat or reduce the incidence of or severity of allergy by increasing the presence or abundance of bacterial strains not present in the pharmaceutical compositions in the microbiome of the subject. As shown herein, administration of bacterial compositions of the disclosure was associated with global shifts in the microbiomes of the subjects. It should further be appreciated that administration of the pharmaceutical compositions described herein may result in a combination of any of the results described. Thus, for instance, food allergy in a subject is treated because the microbiome of the subject upon treatment includes strains of the administered bacterial compositions and bacterial strains associated with a healthy microbiome or a microbiome found in subjects that do not have food allergy.

In general, administration of multiple doses of the pharmaceutical compositions described herein may provide enhanced colonization (engraftment) of one or more bacterial strains of the pharmaceutical compositions as compared to administration of a single dose of the pharmaceutical composition. In some embodiments, administration of multiple doses of the pharmaceutical compositions described herein induces or enhances one or more beneficial immune response in the treatment of allergy as compared to administration of a single dose of the pharmaceutical composition. In some embodiments, administration of multiple doses of the pharmaceutical compositions described herein provides increased abundance of one or more bacterial strains of the pharmaceutical compositions as compared to administration of a single dose of the pharmaceutical composition. In some embodiments, administration of multiple doses of the pharmaceutical compositions described herein modifies (e.g., increases or decreases) the abundance of one or more bacterial strains that are not present in the pharmaceutical compositions as compared to administration of a single dose of the pharmaceutical composition.

In any of the embodiments described herein, the pharmaceutical compositions may be administered to a subject prior to, subsequently to, or concurrently with an allergen immunotherapy regimen. Examples of allergen immunotherapy regimen include oral immunotherapy ("OTT"), sublingual immunotherapy ("SLIT," e.g., "allergy drops/tablets"), subcutaneous allergen administration (e.g., allergy shot), and epicutaneous immunotherapy (e.g., an allergen patch). In general, allergen immunotherapy regimens involve administering an allergen (e.g., a food allergen) to subject in gradually increasing dosages to desensitize the subject to the allergen. Such immunotherapies may also be referred to as "tolarogenic" or "tolerogenic" vaccines.

In some embodiments, the pharmaceutical composition described herein are used in combination with an oral immunotherapy comprising administering a tolerogenic antigen that induce a tolerogenic immune response. Any of the allergens described herein, e.g., food allergens, may be administered to the subject in an allergen immunotherapy regimen. In some embodiments, the allergen immunotherapy comprises an allergen specific to a food allergy. In some embodiments, the food allergen is a peanut allergen, other nut allergen, milk allergen, or an egg allergen. Examples of oral or sublingual immunotherapies include, without limitation, Hello, Peanut!® (Assured Bites, Inc.); AR101 (peanut allergen, Aimmune Therapeutics); AR201 (egg allergen, Aimmune Therapeutics); AR301 (walnut allergen, Aimmune Therapeutics); SAR439794 (Sanofi). In some embodiments, the pharmaceutical compositions are not administered to a subject prior to, subsequently to, or concurrently with an allergen immunotherapy regimen.

In some embodiments, in the methods provided herein the subject is challenged with an allergen immunotherapy regimen to assess the susceptibility of a subject to food allergy during or after the administration of any one of the compositions provided herein according to any one of the methods provided herein.

In some embodiments, any of the pharmaceutical compositions described herein may be administered to the subject concomitantly with an oral immunotherapy or sublingual immunotherapy. Concomitant administration may encompass administration of the pharmaceutical composition and the oral immunotherapy or sublingual within a specified period of time, preferably within 1 month, more preferably within 1 week, still more preferably within 1 day, and even more preferably within 1 hour. In embodiments, the materials/agents may be repeatedly administered concomitantly; that is concomitant administration on more than one occasion.

In embodiments, any of the pharmaceutical compositions described herein may be administered to the subject sequentially (e.g. before or after) or simultaneously with an oral immunotherapy or sublingual immunotherapy.

In some embodiments, a bowel preparation is performed prior to administration of any of the compositions described herein.

In some embodiments, a stool sample is collected after administration of any of the compositions described herein to asses if the bacterial strains of the compositions are engrafted in the microbiome of the subject. In some embodiments, a stool sample is collected after administration of any of the compositions described herein to analyze the composition of the microbiome of the subject. In some embodiments, a stool sample is collected after administration of any of the compositions described herein to analyze the composition of the microbiome of the subject and to asses if the bacterial strains of the compositions are engrafted in the microbiome of the subject.

The compositions, including the pharmaceutical compositions disclosed herein, include compositions that contain selected bacterial strains. The amount of bacteria, including the amount of bacteria of each of the bacterial strains, in the compositions, including pharmaceutical compositions, may be expressed in weight, number of bacteria and/or CFUs (colony forming units). In some embodiments, the compositions, including pharmaceutical compositions, comprise about 10, about $10^2$, about $10^3$, about $10^4$, about $10^5$, about $10^6$, about $10^7$, about $10^8$, about $10^9$, about $10^{10}$, about $10^{11}$, about $10^{12}$, about $10^{13}$ or more of each of the bacterial strains per dosage amount. In some embodiments, the compositions, including pharmaceutical compositions, comprise about 10, about $10^2$, about $10^3$, about $10^4$, about $10^5$, about $10^6$, about $10^7$, about $10^8$, about $10^9$, about $10^{10}$, about $10^{11}$, about $10^{12}$, about $10^{13}$ or more total bacteria per dosage amount. It should further be appreciated that bacteria of each of the bacterial strains may be present in different amounts. Thus, for instance, as a non-limiting example, composition may include $10^3$ of bacteria A, $10^4$ of bacteria B and $10^6$ of bacteria C. In some embodiments, compositions, including pharmaceutical composition, comprise about 10, about $10^2$, about $10^3$, about $10^4$, about $10^5$, about $10^6$, about $10^7$, about $10^8$, about $10^9$, about $10^{10}$, about $10^{11}$, about $10^{12}$, about $10^{13}$ or more CFUs of each of the bacterial strains per dosage amount. In some embodiments, compositions, including pharmaceutical compositions, comprise about $10^1$, about $10^2$, about $10^3$, about $10^4$, about $10^5$, about $10^6$, about $10^7$, about $10^8$, about $10^9$, about $10^{10}$, about $10^{11}$, about $10^{12}$, about $10^{13}$ or more CFUs in total for all of the bacterial strains combined per dosage amount. As discussed above, bacteria of each of the bacterial strains may be present in different amounts. In some embodiments, the compositions, including pharmaceutical compositions, contain about $10^{-7}$, about $10^{-6}$, about $10^{-5}$, about $10^{-4}$, about $10^{-3}$, about $10^{-2}$, about $10^{-1}$ or more grams of bacteria of each of the bacterial strains in the composition per dosage amount. In some embodiments, the compositions, including pharmaceutical compositions, contain about $10^{-7}$, about $10^{-6}$, about $10^{-5}$, about $10^{-4}$, about $10^{-3}$, about $10^{-2}$, about $10^{-1}$ or more grams of bacteria in total for all of the bacterial strains combined per dosage amount. In some embodiments, the dosage amount is one administration device (e.g., one table, pill or capsule). In some embodiment, the dosage amount is the amount that is administered in a particular period (e.g., one day or one week).

In some embodiments, the compositions, including pharmaceutical compositions, contain between 10 and $10^{13}$, between $10^2$ and $10^{13}$, between $10^3$ and $10^{13}$, between $10^4$ and $10^{13}$, between $10^5$ and $10^{13}$, between $10^6$ and $10^{13}$, between $10^7$ and $10^{13}$, between $10^8$ and $10^{13}$, between $10^9$ and $10^{13}$, between $10^{10}$ and $10^{13}$, between $10^{11}$ and $10^{13}$, between $10^{12}$ and $10^{13}$, between 10 and $10^{12}$, between $10^2$ and $10^{12}$, between $10^3$ and $10^{12}$, between $10^4$ and $10^{12}$, between $10^5$ and $10^{12}$, between $10^6$ and $10^{12}$, between $10^7$ and $10^{12}$, between $10^8$ and $10^{12}$, between $10^9$ and $10^{12}$, between $10^{10}$ and $10^{12}$, between $10^{11}$ and $10^{12}$, between 10 and $10^{11}$, between $10^2$ and $10^{11}$ between $10^3$ and $10^{13}$, between $10^4$ and $10^{13}$ between $10^5$ and $10^{13}$ between $10^6$ and $10^{13}$ between $10^7$ and $10^{11}$ between $10^8$ and $10^{11}$ between $10^9$ and $10^{11}$ between $10^{10}$ and $10^{11}$, between 10 and $10^{10}$, between $10^2$ and $10^{10}$, between $10^3$ and $10^{10}$, between $10^4$ and $10^{10}$ between $10^5$ and $10^{10}$ between $10^6$ and $10^{10}$ between $10^7$ and $10^{10}$ between $10^8$ and $10^{10}$, between $10^9$ and $10^{10}$, between 10 and $10^9$, between $10^2$ and $10^9$, between $10^3$ and $10^9$ between $10^4$ and $10^9$ between $10^5$ and $10^9$ between $10^6$ and $10^9$ between $10^7$ and $10^9$, between $10^8$ and $10^9$, between 10 and $10^8$, between $10^2$ and $10^8$, between $10^3$ and $10^8$, between $10^4$ and $10^8$, between $10^5$ and $10^8$, between $10^6$ and $10^8$, between $10^7$ and $10^8$, between 10 and $10^7$, between $10^2$ and $10^7$, between $10^3$ and $10^7$, between $10^4$ and $10^7$, between $10^5$ and $10^7$, between $10^6$ and $10^7$, between 10 and $10^6$, between $10^2$ and $10^6$, between $10^3$ and $10^6$, between $10^4$ and $10^6$, between $10^5$ and $10^6$, between 10 and $10^5$, between $10^2$ and $10^5$, between $10^3$ and $10^5$, between $10^4$ and $10^5$, between 10 and $10^4$, between $10^2$ and $10^4$, between $10^3$ and $10^4$, between 10 and $10^3$, between $10^2$ and $10^3$, or between 10 and $10^2$ of each of the bacterial strains per dosage amount. In some embodiments, the compositions, including pharmaceutical compositions, contain between 10 and $10^{13}$, between $10^2$ and $10^{13}$, between $10^3$ and $10^{13}$, between $10^4$ and $10^{13}$, between $10^5$ and $10^{13}$, between $10^6$ and $10^{13}$, between $10^7$ and $10^{13}$, between $10^8$ and $10^{13}$, between $10^9$ and $10^{13}$, between $10^{10}$ and $10^{13}$, between $10^{11}$ and $10^{13}$, between $10^{12}$ and $10^{13}$, between 10 and $10^{12}$, between $10^2$ and $10^{12}$, between $10^3$ and $10^{12}$, between $10^4$ and $10^{12}$ between $10^5$ and $10^{12}$ between $10^6$ and $10^{12}$ between $10^7$ and $10^{12}$ between $10^8$ and $10^{12}$, between $10^9$ and $10^{12}$, between $10^{10}$ and $10^{12}$, between $10^{11}$ and $10^{12}$, between 10 and $10^{11}$, between $10^2$ and $10^{11}$, between $10^3$ and $10^{13}$, between $10^4$ and $10^{13}$, between $10^5$ and $10^{13}$, between $10^6$ and $10^{13}$, between $10^7$ and $10^{11}$, between $10^8$ and $10^{11}$, between $10^9$ and $10^{11}$, between $10^{10}$ and $10^{11}$, between 10 and $10^{10}$, between $10^2$ and $10^{10}$, between $10^3$ and $10^{10}$, between $10^4$ and $10^{10}$, between $10^5$ and $10^{10}$, between $10^6$ and $10^{10}$, between $10^7$ and $10^{10}$, between $10^8$ and $10^{10}$, between $10^9$ and $10^{10}$, between 10 and $10^9$, between $10^2$ and $10^9$, between $10^3$ and $10^9$, between $10^4$ and $10^9$, between $10^5$ and $10^9$, between $10^6$ and $10^9$, between $10^7$ and $10^9$, between $10^8$ and $10^9$, between 10 and $10^8$, between $10^2$ and $10^8$, between $10^3$ and $10^8$, between $10^4$ and $10^8$, between $10^5$ and $10^8$, between $10^6$ and $10^8$, between $10^7$ and $10^8$, between 10 and $10^7$, between $10^2$ and $10^7$, between $10^3$ and $10^7$, between $10^4$ and $10^7$, between $10^5$ and $10^7$, between $10^6$ and $10^7$, between 10 and $10^6$, between $10^2$ and $10^6$, between $10^3$ and $10^6$, between $10^4$ and $10^6$, between $10^5$ and $10^6$, between 10 and $10^5$, between $10^2$ and $10^5$, between $10^3$ and $10^5$, between $10^4$ and $10^5$, between 10 and $10^4$, between $10^2$ and $10^4$, between $10^3$ and $10^4$, between 10 and $10^3$, between $10^2$ and $10^3$, or between 10 and $10^2$ CFUs of each of the bacterial strains per dosage amount. In some embodiments, the compositions, including pharmaceutical compositions contain between 10 and $10^{13}$, between $10^2$ and $10^{13}$, between $10^3$ and $10^{13}$, between $10^4$ and $10^{13}$, between $10^5$ and $10^{13}$, between $10^6$ and $10^{13}$, between $10^7$ and $10^{13}$, between $10^8$ and $10^{13}$, between $10^9$ and $10^{13}$, between $10^{10}$ and $10^{13}$, between $10^{11}$ and $10^{13}$, between $10^{12}$ and $10^{13}$, between 10 and $10^{12}$, between $10^2$ and $10^{12}$, between $10^3$ and $10^{12}$, between $10^4$ and $10^{12}$, between $10^5$ and $10^{12}$, between $10^6$ and $10^{12}$, between $10^7$ and $10^{12}$, between $10^8$ and $10^{12}$, between $10^9$ and $10^{12}$, between $10^{10}$ and $10^{12}$, between $10^{11}$ and $10^{12}$, between 10 and $10^{11}$, between $10^2$ and $10^{11}$, between $10^3$ and $10^{13}$, between $10^4$ and $10^{13}$, between $10^5$ and $10^{13}$, between $10^6$ and $10^{13}$, between $10^7$ and $10^{11}$, between $10^8$ and $10^{11}$, between $10^9$ and $10^{11}$, between $10^{10}$ and $10^{11}$, between 10 and $10^{10}$, between $10^2$ and $10^{10}$, between $10^3$ and $10^{10}$, between $10^4$ and $10^{10}$, between $10^5$ and $10^{10}$, between $10^6$ and $10^{10}$, between $10^7$ and $10^{10}$, between $10^8$ and $10^{10}$, between $10^9$ and $10^{10}$, between 10 and $10^9$, between $10^2$ and $10^9$ between $10^3$ and $10^9$ between $10^4$ and $10^9$ between $10^5$ and $10^9$ between $10^6$ and $10^9$, between $10^7$ and $10^9$, between $10^8$ and $10^9$, between 10 and $10^8$, between $10^2$ and $10^8$, between $10^3$ and $10^8$, between $10^4$ and $10^8$, between $10^5$ and $10^8$, between $10^6$ and $10^8$, between $10^7$ and $10^8$, between 10 and $10^7$, between $10^2$ and $10^7$, between $10^3$ and $10^7$, between $10^4$ and $10^7$, between $10^5$ and $10^7$, between $10^6$ and $10^7$, between 10 and $10^6$, between $10^2$ and $10^6$, between $10^3$ and $10^6$, between $10^4$ and $10^6$, between $10^5$ and $10^6$, between 10 and $10^5$, between $10^2$ and $10^5$, between $10^3$ and $10^5$, between $10^4$ and $10^5$, between 10 and $10^4$, between $10^2$ and $10^4$, between $10^3$ and $10^4$, between 10 and $10^3$, between $10^2$ and $10^3$, or between 10 and $10^2$ total CFUs per dosage amount.

In some embodiments, the compositions, including pharmaceutical compositions, contain between $10^{-7}$ and $10^{-1}$, between $10^{-6}$ and $10^{-1}$, between $10^{-5}$ and $10^{-1}$, between $10^{-4}$ and $10^{-1}$, between $10^{-3}$ and $10^{-1}$, between $10^{-2}$ and $10^{-1}$, between $10^{-7}$ and $10^{-2}$, between $10^{-6}$ and $10^{-2}$, between $10^{-5}$ and $10^{-2}$, between $10^{-4}$ and $10^{-2}$, between $10^{-3}$ and $10^{-2}$, between $10^{-7}$ and $10^{-3}$, between $10^{-6}$ and $10^{-3}$, between $10^{-5}$ and $10^{-3}$, between $10^{-4}$ and $10^{-3}$, between $10^{-7}$ and $10^{-4}$, between $10^{-6}$ and $10^{-4}$, between $10^{-5}$ and $10^{-4}$, between $10^{-7}$ and $10^{-5}$, between $10^{-6}$ and $10^{-5}$, or between $10^{-7}$ and $10^{-6}$ grams of bacteria of each of the bacterial strains in the composition per dosage amount. In some embodiments, the compositions, including pharmaceutical compositions, disclosed herein contain between $10^{-7}$ and $10^{-1}$, between $10^{-6}$ and $10^{-1}$, between $10^{-5}$ and $10^{-1}$, between $10^{-4}$ and $10^{-1}$, between $10^{-3}$ and $10^{-1}$, between $10^{-2}$ and $10^{-1}$, between $10^{-7}$ and $10^{-2}$, between $10^{-6}$ and $10^{-2}$, between $10^{-5}$ and $10^{-2}$, between $10^{-4}$ and $10^{-2}$, between $10^{-3}$ and $10^{-2}$, between $10^{-7}$ and $10^{-3}$, between $10^{-6}$ and $10^{-3}$, between $10^{-5}$ and $10^{-3}$, between $10^{-4}$ and $10^{-3}$, between $10^{-7}$ and $10^{-4}$, between $10^{-6}$ and $10^{-4}$, between $10^{-5}$ and $10^{-4}$, between $10^{-7}$ and $10^{-5}$, between $10^{-6}$ and $10^{-5}$, or between $10^{-7}$ and $10^{-6}$ grams of all of the bacteria combined (total) per dosage amount.

Aspects of the present disclosure also provide food products comprising any of the compositions provided herein and a nutrient. Also with the scope of the present disclosure are food products comprising any of the bacterial strains described herein and a nutrient. Food products are, in general, intended for the consumption of a human or an animal. Any of the compositions described herein may be formulated as a food product. In some embodiments, the bacterial strains are formulated as a food product in spore form. In some embodiments, the bacterial strains are formulated as a food product in vegetative form. In some embodiments, the food product comprises both vegetative bacteria and bacteria in spore form. The compositions disclosed herein can be used in a food or beverage, such as a health food or beverage, a food or beverage for infants, a food or beverage for pregnant women, athletes, senior citizens or other specified group, a functional food, a beverage, a food or beverage for specified health use, a dietary supplement, a food or beverage for patients, or an animal feed.

Non-limiting examples of the foods and beverages include various beverages such as juices, refreshing beverages, tea beverages, drink preparations, jelly beverages, and functional beverages; alcoholic beverages such as beers; carbohydrate-containing foods such as rice food products, noodles, breads, and pastas; paste products such as fish hams, sausages, paste products of seafood; retort pouch products such as curries, food dressed with a thick starchy sauces, soups; dairy products such as milk, dairy beverages, ice creams, cheeses, and yogurts; fermented products such as fermented soybean pastes, yogurts, fermented beverages, and pickles; bean products; various confectionery products such as Western confectionery products including biscuits, cookies, and the like, Japanese confectionery products including steamed bean-jam buns, soft adzuki-bean jellies, and the like, candies, chewing gums, gummies, cold desserts including jellies, cream caramels, and frozen desserts; instant foods such as instant soups and instant soy-bean soups; microwavable foods; and the like. Further, the examples also include health foods and beverages prepared in the forms of powders, granules, tablets, capsules, liquids, pastes, and jellies.

Food products containing the bacterial strains described herein may be produced using methods known in the art and may contain the same amount of bacteria (e.g., by weight, amount or CFU) as the pharmaceutical compositions provided herein. Selection of an appropriate amount of bacteria in the food product may depend on various factors, including for example, the serving size of the food product, the frequency of consumption of the food product, the specific bacterial strains contained in the food product, the amount of water in the food product, and/or additional conditions for survival of the bacteria in the food product.

Examples of food products which may be formulated to contain any of the bacterial strains described herein include, without limitation, a beverage, a drink, a bar, a snack, a dairy product, a confectionery product, a cereal product, a ready-to-eat product, a nutritional formula, such as a nutritional supplementary formulation, a food or beverage additive.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Unless otherwise defined herein, scientific and technical terms used in connection with the present disclosure shall have the meanings that are commonly understood by those of ordinary skill in the art. Further, unless otherwise required by context, singular terms shall include pluralities and plural terms hall include the singular. The methods and techniques of the present disclosure are generally performed according to conventional methods well-known in the art. Generally, nomenclatures used in connection with, and techniques of biochemistry, enzymology, molecular and cellular biology, microbiology, virology, cell or tissue culture, genetics and protein and nucleic chemistry described herein are those well-known and commonly used in the art. The methods and techniques of the present disclosure are generally performed according to conventional methods well known in the art and as described in various general and more specific references that are cited and discussed throughout the present specification unless otherwise indicated.

```
Strain 1 16S ribosomal RNA Clostridium bolteae
                                                              SEQ ID NO: 1
ATGAGAGTTTGATCCTGGCTCAGGATGAACGCTGGCGGCGTGCCTAACACATGCAAGTCGAACGAAGCAA

TTAAAATGAAGTTTTCGGATGGATTTTTGATTGACTGAGTGGCGGACGGGTGAGTAACGCGTGGATAACC
```

```
TGCCTCACACTGGGGGATAACAGTTAGAAATGACTGCTAATACCGCATAAGCGCACAGTACCGCATGGTA
CGGTGTGAAAAACTCCGGTGGTGTGAGATGGATCCGCGTCTGATTAGCCAGTTGGCGGGGTAACGGCCCA
CCAAAGCGACGATCAGTAGCCGACCTGAGAGGGTGACCGGCCACATTGGGACTGAGACACGGCCCAAACT
CCTACGGGAGGCAGCAGTGGGGAATATTGCACAATGGGCGAAAGCCTGATGCAGCGACGCCGCGTGAGTG
AAGAAGTATTTCGGTATGTAAAGCTCTATCAGCAGGGAAGAAAATGACGGTACCTGACTAAGAAGCCCCG
GCTAACTACGTGCCAGCAGCCGCGGTAATACGTAGGGGGCAAGCGTTATCCGGATTTACTGGGTGTAAAG
GGAGCGTAGACGGCGAAGCAAGTCTGAAGTGAAAACCCAGGGCTCAACCCTGGGACTGCTTTGGAAACTG
TTTTGCTAGAGTGTCGGAGAGGTAAGTGGAATTCCTAGTGTAGCGGTGAAATGCGTAGATATTAGGAGGA
ACACCAGTGGCGAAGGCGGCTTACTGGACGATAACTGACGTTGAGGCTCGAAAGCGTGGGGAGCAAACAG
GATTAGATACCCTGGTAGTCCACGCCGTAAACGATGAATGCTAGGTGTTGGGGGCAAAGCCCTTCGGTG
CCGTCGCAAACGCAGTAAGCATTCCACCTGGGGAGTACGTTCGCAAGAATGAAACTCAAAGGAATTGACG
GGGACCCGCACAAGCGGTGGAGCATGTGGTTTAATTCGAAGCAACGCGAAGAACCTTACCAAGTCTTGAC
ATCCTCTTGACCGGCGTGTAACGGCGCCTTCCCTTCGGGGCAAGAGAGACAGGTGGTGCATGGTTGTCGT
CAGCTCGTGTCGTGAGATGTTGGGTTAAGTCCCGCAACGAGCGCAACCCTTATCCTTAGTAGCCAGCAGG
TAAAGCTGGGCACTCTAGGGAGACTGCCAGGGATAACCTGGAGGAAGGTGGGGATGACGTCAAATCATCA
TGCCCCTTATGATTTGGGCTACACACGTGCTACAATGGCGTAAACAAAGGGAAGCAAGACAGTGATGTGG
AGCAAATCCCAAAAATAACGTCCCAGTTCGGACTGTAGTCTGCAACCCGACTACACGAAGCTGGAATCGC
TAGTAATCGCGAATCAGAATGTCGCGGTGAATACGTTCCCGGGTCTTGTACACACCGCCCGTCACACCAT
GGGAGTCAGCAACGCCCGAAGTCAGTGACCCAACTCGCAAGAGAGGGAGCTGCCGAAGGCGGGGCAGGTA
ACTGGGGTGAAGTCGTAACAAGGTAGCCGTATCGGAAGGTGCGGCTGGATCACCTCCTTT
```

Strain 2 16S ribosomal RNA *Anaerotruncus colihominis*

SEQ ID NO: 2

```
TCAAAGAGTTTGATCCTGGCTCAGGACGAACGCTGGCGGCGCGCCTAACACATGCAAGTCGAACGGAGCT
TACGTTTTGAAGTTTTCGGATGGATGAATGTAAGCTTAGTGGCGGACGGGTGAGTAACACGTGAGCAACC
TGCCTTTCAGAGGGGGATAACAGCCGGAAACGGCTGCTAATACCGCATGATGTTGCGGGGGCACATGCCC
CTGCAACCAAAGGAGCAATCCGCTGAAAGATGGGCTCGCGTCCGATTAGCCAGTTGGCGGGGTAACGGCC
CACCAAAGCGACGATCGGTAGCCGGACTGAGAGGTTGAACGGCCACATTGGGACTGAGACACGGCCCAGA
CTCCTACGGGAGGCAGCAGTGGGGATATTGCACAATGGGCGAAAGCCTGATGCAGCGACGCCGCGTGAG
GGAAGACGGTCTTCGGATTGTAAACCTCTGTCTTTGGGGAAGAAAATGACGGTACCCAAAGAGGAAGCTC
CGGCTAACTACGTGCCAGCAGCCGCGGTAATACGTAGGGAGCAAGCGTTGTCCGGAATTACTGGGTGTAA
AGGGAGCGTAGGCGGGATGGCAAGTAGAATGTTAAATCCATCGGCTCAACCGGTGGCTGCGTTCTAAACT
GCCGTTCTTGAGTGAAGTAGAGGCAGGCGGAATTCCTAGTGTAGCGGTGAAATGCGTAGATATTAGGAGG
AACACCAGTGGCGAAGGCGGCCTGCTGGGCTTTAACTGACGCTGAGGCTCGAAAGCGTGGGGAGCAAACA
GGATTAGATACCCTGGTAGTCCACGCCGTAAACGATGATTACTAGGTGTGGGGGACTGACCCCTTCCGT
GCCGCAGTTAACACAATAAGTAATCCACCTGGGGAGTACGGCCGCAAGGTTGAAACTCAAAGGAATTGAC
GGGGGCCCGCACAAGCAGTGGAGTATGTGGTTTAATTCGAAGCAACGCGAAGAACCTTACCAGGTCTTGA
CATCGGATGCATAGCCTAGAGATAGGTGAAGCCCTTCGGGGCATCCAGACAGGTGGTGCATGGTTGTCGT
CAGCTCGTGTCGTGAGATGTTGGGTTAAGTCCCGCAACGAGCGCAACCCTTATTATTAGTTGCTACGCAA
GAGCACTCTAATGAGACTGCCGTTGACAAAACGGAGGAAGGTGGGGATGACGTCAAATCATCATGCCCCT
TATGACCTGGGCTACACACGTACTACAATGGCACTAAAACAGAGGGCGGCGACACCGCGAGGTGAAGCGA
ATCCCGAAAAGTGTCTCAGTTCAGATTGCAGGCTGCAACCCGCCTGCATGAAGTCGGAATTGCTAGTAA
TCGCGGATCAGCATGCCGCGGTGAATACGTTCCCGGGCCTTGTACACACCGCCCGTCACACCATGGGAGT
```

-continued

CGGTAACACCCGAAGCCAGTAGCCTAACCGCAAGGGGGCGCTGTCGAAGGTGGGATTGATGACTGGGGT
GAAGTCGTAACAAGGTAGCCGTATCGGAAGGTGCGGCTGGATCACCTCCTTT

Strain 3 16S ribosomal RNA *Ruminococcus torques*

SEQ ID NO: 3

TACGAGAGTTTGATCCTGGCTCAGGATGAACGCTGGCGGCGTGCCTAACACATGCAAGTCGAGCGAAGCG
CTGTTTTCAGAATCTTCGGAGGAAGAGGACAGTGACTGAGCGGCGGACGGGTGAGTAACGCGTGGGCAAC
CTGCCTCATACAGGGGGATAACAGTTAGAAATGACTGCTAATACCGCATAAGCGCACAGGACCGCATGGT
GTAGTGTGAAAAACTCCGGTGGTATGAGATGGACCCGCGTCTGATTAGGTAGTTGGTGGGGTAAAGGCCT
ACCAAGCCGACGATCAGTAGCCGACCTGAGAGGGTGACCGGCCACATTGGGACTGAGACACGGCCCAAAC
TCCTACGGGAGGCAGCAGTGGGGAATATTGCACAATGGGGGAAACCCTGATGCAGCGACGCCGCGTGAAG
GAAGAAGTATTTCGGTATGTAAACTTCTATCAGCAGGGAAGAAAATGACGGTACCTGAGTAAGAAGCACC
GGCTAAATACGTGCCAGCAGCCGCGGTAATACGTATGGTGCAAGCGTTATCCGGATTTACTGGGTGTAAA
GGGAGCGTAGACGGATAGGCAAGTCTGGAGTGAAAACCCAGGGCTCAACCCTGGGACTGCTTTGGAAACT
GCAGATCTGGAGTGCCGGAGAGGTAAGCGGAATTCCTAGTGTAGCGGTGAAATGCGTAGATATTAGGAGG
AACACCAGTGGCGAAGGCGGCTTACTGGACGGTGACTGACGTTGAGGCTCGAAAGCGTGGGGAGCAAACA
GGATTAGATACCCTGGTAGTCCACGCCGTAAACGATGACTACTAGGTGTCGGTGTGCAAAGCACATCGGT
GCCGCAGCAAACGCAATAAGTAGTCCACCTGGGGAGTACGTTCGCAAGAATGAAACTCAAAGGAATTGAC
GGGGACCCGCACAAGCGGTGGAGCATGTGGTTTAATTCGAAGCAACGCGAAGAACCTTACCTGGTCTTGA
CATCCGGATGACGGGCGAGTAATGTCGCCGTCCCTTCGGGGCGTCCGAGACAGGTGGTGCATGGTTGTCG
TCAGCTCGTGTCGTGAGATGTTGGGTTAAGTCCCGCAACGAGCGCAACCCTTATCTTCAGTAGCCAGCAT
ATAAGGTGGGCACTCTGGAGAGACTGCCAGGGAGAACCTGGAGGAAGGTGGGGATGACGTCAAATCATCA
TGCCCCTTATGGCCAGGGCTACACACGTGCTACAATGGCGTAAACAAAGGGAAGCGAGAGGGTGACCTGG
AGCGAATCCCAAAAATAACGTCTCAGTTCGGATTGTAGTCTGCAACTCGACTACATGAAGCTGGAATCGC
TAGTAATCGCGGATCAGCATGCCGCGGTGAATACGTTCCCGGGTCTTGTACACACCGCCCGTCACACCAT
GGGAGTCAGTAACGCCCGAAGCCAGTGACCCAACCTTAGAGGAGGGAGCTGTCGAAGGCGGGACGGATAA
CTGGGGTGAAGTCGTAACAAGGTAGCCGTATCGGAAGGTGCGGCTGGATCACCTCCTTT

Strain 4 16S ribosomal RNA *Clostridium symbiosum*

SEQ ID NO: 4

ATGAGAGTTTGATCCTGGCTCAGGATGAACGCTGGCGGCGTGCCTAACACATGCAAGTCGAACGAAGCGA
TTTAACGGAAGTTTTCGGATGGAAGTTGAATTGACTGAGTGGCGGACGGGTGAGTAACGCGTGGGTAACC
TGCCTTGTACTGGGGGACAACAGTTAGAAATGACTGCTAATACCGCATAAGCGCACAGTATCGCATGATA
CAGTGTGAAAAACTCCGGTGGTACAAGATGGACCCGCGTCTGATTAGCTAGTTGGTAAGGTAACGGCTTA
CCAAGGCGACGATCAGTAGCCGACCTGAGAGGGTGACCGGCCACATTGGGACTGAGACACGGCCCAAACT
CCTACGGGAGGCAGCAGTGGGGAATATTGCACAATGGGCGAAAGCCTGATGCAGCGACGCCGCGTGAGTG
AAGAAGTATTTCGGTATGTAAAGCTCTATCAGCAGGGAAGAAAATGACGGTACCTGACTAAGAAGCCCCG
GCTAACTACGTGCCAGCAGCCGCGGTAATACGTAGGGGGCAAGCGTTATCCGGATTTACTGGGTGTAAAG
GGAGCGTAGACGGTAAAGCAAGTCTGAAGTGAAAGCCCGCGGCTCAACTGCGGGACTGCTTTGGAAACTG
TTTAACTGGAGTGTCGGAGAGGTAAGTGGAATTCCTAGTGTAGCGGTGAAATGCGTAGATATTAGGAGGA
ACACCAGTGGCGAAGGCGACTTACTGGACGATAACTGACGTTGAGGCTCGAAAGCGTGGGGAGCAAACAG
GATTAGATACCCTGGTAGTCCACGCCGTAAACGATGAATACTAGGTGTTGGGGAGCAAAGCTCTTCGGTG
CCGTCGCAAACGCAGTAAGTATTCCACCTGGGGAGTACGTTCGCAAGAATGAAACTCAAAGGAATTGACG
GGGACCCGCACAAGCGGTGGAGCATGTGGTTTAATTCGAAGCAACGCGAAGAACCTTACCAGGTCTTGAC

```
ATCGATCCGACGGGGGAGTAACGTCCCCTTCCCTTCGGGGCGGAGAAGACAGGTGGTGCATGGTTGTCGT

CAGCTCGTGTCGTGAGATGTTGGGTTAAGTCCCGCAACGAGCGCAACCCTTATTCTAAGTAGCCAGCGGT

TCGGCCGGGAACTCTTGGGAGACTGCCAGGGATAACCTGGAGGAAGGTGGGGATGACGTCAAATCATCAT

GCCCCTTATGATCTGGGCTACACACGTGCTACAATGGCGTAAACAAAGAGAAGCAAGACCGCGAGGTGGA

GCAAATCTCAAAAATAACGTCTCAGTTCGGACTGCAGGCTGCAACTCGCCTGCACGAAGCTGGAATCGCT

AGTAATCGCGAATCAGAATGTCGCGGTGAATACGTTCCCGGGTCTTGTACACACCGCCCGTCACACCATG

GGAGTCAGTAACGCCCGAAGTCAGTGACCCAACCGCAAGGAGGGAGCTGCCGAAGGCGGGACCGATAACT

GGGGTGAAGTCGTAACAAGGTAGCCGTATCGGAAGGTGCGGCTGGATCACCTCCTTT
```

Strain 5 16S ribosomal RNA *Blautia producta*

SEQ ID NO: 5

```
ATCAGAGAGTTTGATCCTGGCTCAGGATGAACGCTGGCGGCGTGCTTAACACATGCAAGTCGAGCGAAGC

ACTTAAGTGGATCTCTTCGGATTGAAGCTTATTTGACTGAGCGGCGGACGGGTGAGTAACGCGTGGGTAA

CCTGCCTCATACAGGGGGATAACAGTTAGAAATGGCTGCTAATACCGCATAAGCGCACAGGACCGCATGG

TCTGGTGTGAAAAACTCCGGTGGTATGAGATGGACCCGCGTCTGATTAGCTAGTTGGAGGGGTAACGGCC

CACCAAGGCGACGATCAGTAGCCGGCCTGAGAGGGTGAACGGCCACATTGGGACTGAGACACGGCCCAGA

CTCCTACGGGAGGCAGCAGTGGGGAATATTGCACAATGGGGGAAACCCTGATGCAGCGACGCCGCGTGAA

GGAAGAAGTATCTCGGTATGTAAACTTCTATCAGCAGGGAAGAAAATGACGGTACCTGACTAAGAAGCCC

CGGCTAACTACGTGCCAGCAGCCGCGGTAATACGTAGGGGGCAAGCGTTATCCGGATTTACTGGGTGTAA

AGGGAGCGTAGACGGAAGAGCAAGTCTGATGTGAAAGGCTGGGGCTTAACCCCAGGACTGCATTGGAAAC

TGTTTTTCTAGAGTGCCGGAGAGGTAAGCGGAATTCCTAGTGTAGCGGTGAAATGCGTAGATATTAGGAG

GAACACCAGTGGCGAAGGCGGCTTACTGGACGGTAACTGACGTTGAGGCTCGAAAGCGTGGGGAGCAAAC

AGGATTAGATACCCTGGTAGTCCACGCCGTAAACGATGAATACTAGGTGTCGGGTGGCAAAGCCATTCGG

TGCCGCAGCAAACGCAATAAGTATTCCACCTGGGGAGTACGTTCGCAAGAATGAAACTCAAAGGAATTGA

CGGGGACCCGCACAAGCGGTGGAGCATGTGGTTTAATTCGAAGCAACGCGAAGAACCTTACCAAGTCTTG

ACATCCCTCTGACCGGCCCGTAACGGGCCTTCCCTTCGGGGCAGAGGAGACAGGTGGTGCATGGTTGTC

GTCAGCTCGTGTCGTGAGATGTTGGGTTAAGTCCCGCAACGAGCGCAACCCCTATCCTTAGTAGCCAGCA

GGTGAAGCTGGGCACTCTAGGGAGACTGCCGGGGATAACCCGGAGGAAGGCGGGGACGACGTCAAATCAT

CATGCCCCTTATGATTTGGGCTACACACGTGCTACAATGGCGTAAACAAAGGGAAGCGAGACAGCGATGT

TGAGCAAATCCCAAAAATAACGTCCCAGTTCGGACTGCAGTCTGCAACTCGACTGCACGAAGCTGGAATC

GCTAGTAATCGCGAATCAGAATGTCGCGGTGAATACGTTCCCGGGTCTTGTACACACCGCCCGTCACACC

ATGGGAGTCAGTAACGCCCGAAGTCAGTGACCCAACCTTACAGGAGGGAGCTGCCGAAGGCGGGACCGAT

AACTGGGGTGAAGTCGTAACAAGGTAGCCGTATCGGAAGGTGCGGCTGGATCACCTCCTTT
```

Strain 6 16S ribosomal RNA *Dorea Longicatena*

SEQ ID NO: 6

```
AACGAGAGTTTGATCCTGGCTCAGGATGAACGCTGGCGGCGTGCTTAACACATGCAAGTCGAGCGAAGCA

CTTAAGTTTGATTCTTCGGATGAAGACTTTTGTGACTGAGCGGCGGACGGGTGAGTAACGCGTGGGTAAC

CTGCCTCATACAGGGGGATAACAGTTAGAAATGACTGCTAATACCGCATAAGACCACGGTACCGCATGGT

ACAGTGGTAAAAACTCCGGTGGTATGAGATGGACCCGCGTCTGATTAGGTAGTTGGTGGGGTAACGGCCT

ACCAAGCCGACGATCAGTAGCCGACCTGAGAGGGTGACCGGCCACATTGGGACTGAGACACGGCCCAGAC

TCCTACGGGAGGCAGCAGTGGGGAATATTGCACAATGGAGGAAACTCTGATGCAGCGACGCCGCGTGAAG

GATGAAGTATTTCGGTATGTAAACTTCTATCAGCAGGGAAGAAAATGACGGTACCTGACTAAGAAGCCCC

GGCTAACTACGTGCCAGCAGCCGCGGTAATACGTAGGGGGCAAGCGTTATCCGGATTTACTGGGTGTAAA

GGGAGCGTAGACGGCACGGCAAGCCAGATGTGAAAGCCCGGGGCTCAACCCCGGGACTGCATTTGGAACT
```

```
GCTGAGCTAGAGTGTCGGAGAGGCAAGTGGAATTCCTAGTGTAGCGGTGAAATGCGTAGATATTAGGAGG

AACACCAGTGGCGAAGGCGGCTTGCTGGACGATGACTGACGTTGAGGCTCGAAAGCGTGGGGAGCAAACA

GGATTAGATACCCTGGTAGTCCACGCCGTAAACGATGACTGCTAGGTGTCGGGTGGCAAAGCCATTCGGT

GCCGCAGCTAACGCAATAAGCAGTCCACCTGGGGAGTACGTTCGCAAGAATGAAACTCAAAGGAATTGAC

GGGGACCCGCACAAGCGGTGGAGCATGTGGTTTAATTCGAAGCAACGCGAAGAACCTTACCTGATCTTGA

CATCCCGATGACCGCTTCGTAATGGAAGCTTTTCTTCGGAACATCGGTGACAGGTGGTGCATGGTTGTCG

TCAGCTCGTGTCGTGAGATGTTGGGTTAAGTCCCGCAACGAGCGCAACCCCTATCTTCAGTAGCCAGCAG

GTTAAGCTGGGCACTCTGGAGAGACTGCCAGGGATAACCTGGAGGAAGGTGGGGATGACGTCAAATCATC

ATGCCCCTTATGACCAGGGCTACACACGTGCTACAATGGCGTAAACAAAGAGAAGCGAACTCGCGAGGGT

AAGCAAATCTCAAAAATAACGTCTCAGTTCGGATTGTAGTCTGCAACTCGACTACATGAAGCTGGAATCG

CTAGTAATCGCAGATCAGAATGCTGCGGTGAATACGTTCCCGGGTCTTGTACACACCGCCCGTCACACCA

TGGGAGTCAGTAACGCCCGAAGTCAGTGACCCAACCGTAAGGAGGGAGCTGCCGAAGGTGGGACCGATAA

CTGGGGTGAAGTCGTAACAAGGTAGCCGTATCGGAAGGTGCGGCTGGATCACCTCCTTT
```
Strain 7 16S ribosomal RNA *Erysipelotrichaceae bacterium*
SEQ ID NO: 7
```
ATGGAGAGTTTGATCCTGGCTCAGGATGAACGCTGGCGGCATGCCTAATACATGCAAGTCGAACGAAGTT

TCGAGGAAGCTTGCTTCCAAAGAGACTTAGTGGCGAACGGGTGAGTAACACGTAGGTAACCTGCCCATGT

GTCCGGGATAACTGCTGGAAACGGTAGCTAAAACCGGATAGGTATACAGAGCGCATGCTCAGTATATTAA

AGCGCCCATCAAGGCGTGAACATGGATGGACCTGCGCGCATTAGCTAGTTGGTGAGGTAACGGCCCACC

AAGGCGATGATGCGTAGCCGGCCTGAGAGGGTAAACGGCCACATTGGGACTGAGACACGGCCCAAACTCC

TACGGGAGGCAGCAGTAGGGAATTTTCGTCAATGGGGGAAACCCTGAACGAGCAATGCCGCGTGAGTGAA

GAAGGTCTTCGGATCGTAAAGCTCTGTTGTAAGTGAAGAACGGCTCATAGAGGAAATGCTATGGGAGTGA

CGGTAGCTTACCAGAAAGCCACGGCTAACTACGTGCCAGCAGCCGCGGTAATACGTAGGTGGCAAGCGTT

ATCCGGAATCATTGGGCGTAAAGGGTGCGTAGGTGGCGTACTAAGTCTGTAGTAAAAGGCAATGGCTCAA

CCATTGTAAGCTATGGAAACTGGTATGCTGGAGTGCAGAAGAGGGCGATGGAATTCCATGTGTAGCGGTA

AAATGCGTAGATATATGGAGGAACACCAGTGGCGAAGGCGGTCGCCTGGTCTGTAACTGACACTGAGGCA

CGAAAGCGTGGGGAGCAAATAGGATTAGATACCCTAGTAGTCCACGCCGTAAACGATGAGAACTAAGTGT

TGGAGGAATTCAGTGCTGCAGTTAACGCAATAAGTTCTCCGCCTGGGGAGTATGCACGCAAGTGTGAAAC

TCAAAGGAATTGACGGGGGCCCGCACAAGCGGTGGAGTATGTGGTTTAATTCGAAGCAACGCGAAGAACC

TTACCAGGCCTTGACATGGAAACAAATACCCTAGAGATAGGGGGATAATTATGGATCACACAGGTGGTGC

ATGGTTGTCGTCAGCTCGTGTCGTGAGATGTTGGGTTAAGTCCCGCAACGAGCGCAACCCTTGTCGCATG

TTACCAGCATCAAGTTGGGACTCATGCGAGACTGCCGGTGACAAACCGGAGGAAGGTGGGGATGACGTC

AAATCATCATGCCCCTTATGGCCTGGGCTACACACGTACTACAATGGCGGCCACAAAGAGCAGCGACACA

GTGATGTGAAGCGAATCTCATAAAGGTCGTCTCAGTTCGGATTGAAGTCTGCAACTCGACTTCATGAAGT

CGGAATCGCTAGTAATCGCAGATCAGCATGCTGCGGTGAATACGTTCTCGGGCCTTGTACACACCGCCCG

TCAAACCATGGGAGTCAGTAATACCCGAAGCCGGTGGCATAACCGTAAGGAGTGAGCCGTCGAAGGTAGG

ACCGATGACTGGGGTTAAGTCGTAACAAGGTATCCCTACGGGAACGTGGGGATGGATCACCTCCTTT
```
Strain 8 16S ribosomal RNA *Subdoligranulum* spp
SEQ ID NO: 8
```
TATTGAGAGTTTGATCCTGGCTCAGGATGAACGCTGGCGGCGTGCTTAACACATGCAAGTCGAACGGGGT

GCTCATGACGGAGGATTCGTCCAACGGATTGAGTTACCTAGTGGCGGACGGGTGAGTAACGCGTGAGGAA

CCTGCCTTGGAGAGGGGAATAACACTCCGAAAGGAGTGCTAATACCGCATGATGCAGTTGGGTCGCATGG
```

-continued

```
CTCTGACTGCCAAAGATTTATCGCTCTGAGATGGCCTCGCGTCTGATTAGCTAGTAGGCGGGGTAACGGC

CCACCTAGGCGACGATCAGTAGCCGGACTGAGAGGTTGACCGGCCACATTGGGACTGAGACACGGCCCAG

ACTCCTACGGGAGGCAGCAGTGGGGAATATTGGGCAATGGGCGCAAGCCTGACCCAGCAACGCCGCGTGA

AGGAAGAAGGCTTTCGGGTTGTAAACTTCTTTTGTCGGGGACGAAACAAATGACGGTACCCGACGAATAA

GCCACGGCTAACTACGTGCCAGCAGCCGCGGTAATACGTAGGTGGCAAGCGTTATCCGGATTTACTGGGT

GTAAAGGGCGTGTAGGCGGGATTGCAAGTCAGATGTGAAAACTGGGGGCTCAACCTCCAGCCTGCATTTG

AAACTGTAGTTCTTGAGTGCTGGAGAGGCAATCGGAATTCCGTGTGTAGCGGTGAAATGCGTAGATATAC

GGAGGAACACCAGTGGCGAAGGCGGATTGCTGGACAGTAACTGACGCTGAGGCGCGAAAGCGTGGGGAGC

AAACAGGATTAGATACCCTGGTAGTCCACGCCGTAAACGATGGATACTAGGTGTGGGGGGTCTGACCCCC

TCCGTGCCGCAGTTAACACAATAAGTATCCCACCTGGGGAGTACGATCGCAAGGTTGAAACTCAAAGGAA

TTGACGGGGGCCCGCACAAGCGGTGGAGTATGTGGTTTAATTCGAAGCAACGCGAAGAACCTTACCAGGG

CTTGACATCCCACTAACGAAGCAGAGATGCATTAGGTGCCCTTCGGGGAAAGTGGAGACAGGTGGTGCAT

GGTTGTCGTCAGCTCGTGTCGTGAGATGTTGGGTTAAGTCCCGCAACGAGCGCAACCCTTATTGTTAGTT

GCTACGCAAGAGCACTCTAGCGAGACTGCCGTTGACAAAACGGAGGAAGGTGGGGACGACGTCAAATCAT

CATGCCCCTTATGTCCTGGGCCACACACGTACTACAATGGTGGTTAACAGAGGGAGGCAATACCGCGAGG

TGGAGCAAATCCCTAAAAGCCATCCCAGTTCGGATTGCAGGCTGAAACCCGCCTGTATGAAGTTGGAATC

GCTAGTAATCGCGGATCAGCATGCCGCGGTGAATACGTTCCCGGGCCTTGTACACACCGCCCGTCACACC

ATGAGAGTCGGGAACACCCGAAGTCCGTAGCCTAACCGCAAGGAGGGCGCGGCCGAAGGTGGGTTCGATA

ATTGGGGTGAAGTCGTAACAAGGTAGCCGTATCGGAAGGTGCGGCTGGATCACCTCCTTT
```

Strain 9 VE202-4; *Clostridium hathewayi*
SEQ ID NO: 9
```
GATGAACGCTGGCGGCGGTGCTTAACACATGCAAGTCGAGCGAAGCGGTTTCGAGTGAAGTTTTGGATGG

AATTGAAATTGACTTAGCGGCGGACGGGTGAGTAACGCGTGGGTAACCTGCCTTACACTGGGGGATAACA

GTTAGAAATGACTGCTAATACCGCATAAGCGCACAGGGCCGCATGGTCTGGTGCGAAAAACTCCGGTGGT

GTAAGATGGACCCGCGTCTGATTAGGTAGTTGGTGGGGTAACGGCCCACCAAGCCGACGATCAGTAGCCG

ACCTGAGAGGGTGACCGGCCACATTGGGACTGAGACACGGCCCAA
```

Strain 10 VE202-9 *Clostridium indolis/Anaerostipes caccae*
SEQ ID NO: 10
```
GATGAACGCTGGCGGCGTGCTTAACACATGCAAGTCGAACGAAGCATTTTGGAAGGAAGTTTTCGGATGG

AATTCCTTAATGACTGAGTGGCGGACGGGTGAGTAACGCGTGGGGAACCTGCCCTATACAGGGGGATAAC

AGCTGGAAACGGCTGCTAATACCGCATAAGCGCACAGAATCGCATGATTCGGTGTGAAAAGCTCCGGCAG

TATAGGATGGTCCCGCGTCTGATTAGCTGGTTGGCGGGGTAACGGCCCACCAAGGCGACGATCAGTAGCC

GGCTTGAGAGAGTGGACGGCCACATTGGGACTGAGACACGGCCCA
```

Strain 11 VE202-27 *Lachnospiraceae bacterium*
SEQ ID NO: 11
```
GATGAACGCTGGCGGCGTGCCTAACACATGCAAGTCGAACGGAGTTATGCAGAGGAAGTTTTCGGATGGA

ATCGGCGTAACTTAGTGGCGGACGGGTGAGTAACGCGTGGGAAACCTGCCCTGTACCGGGGGATAACACT

TAGAAATAGGTGCTAATACCGCATAAGCGCACAGCTTCACATGAAGCAGTGTGAAAAACTCCGGTGGTAC

AGGATGGTCCCGCGTCTGATTAGCCAGTTGGCAGGGTAACGGCCTACCAAAGCGACGATCAGTAGCCGGC

CTGAGAGGGTGAACGGCCACATTGGGACTGAGACACGGCCCA
```

Strain 12 VE202-28 *Clostridium species*
SEQ ID NO: 12
```
GATGAACGCTGGCGGCGTGCCTAACACATGCAAGTCGAACGAAGCATCCCATAGGAAGTTTTCGGATGGA

ATATGGGATGACTGAGTGGCGGACGGGTGAGTAACGCGTGGATAACCTGCCTCACACTGGGGGATAACAG

TTAGAAATGGCTGCTAATACCGCATAAGCGCACAGTACCGCATGGTACGGTGTGAAAAACCCAGGTGGTG
```

```
Strain 13 VE202-29 Lachnospiraceae bacterium
                                                             SEQ ID NO: 13
GATGAACGCTGGCGGCGTGCCTAACACATGCAAGTCGAACGAAGTTAGACAGAGGAAGTTTTCGGATGGA

ATCGGTATAACTTAGTGGCGGACGGGTGAGTAACGCGTGGGAAACCTGCCCTGTACCGGGGATAACACT

TAGAAATAGGTGCTAATACCGCATAAGCGCACGGAACCGCATGGGTTCTGTGTGAAAACTCCGGTGGTAC

AGGATGGTCCCGCGTCTGATTAGCCAGTTGGCAGGGTAACGGCCTACCAAAGCGACGATCAGTAGCCGGC

CTGAGAGGGTGAACGGCCACATTGGGACTGAGACACGGCCCAA
```

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference, in particular for the teaching that is referenced hereinabove. However, the citation of any reference is not intended to be an admission that the reference is prior art.

EXAMPLES

Example 1: Composition B Induces Regulatory T Cells (Tregs)

Each of the bacterial strains of Composition B were grown to log phase, combined to a total dose of ~$10^8$ cfu per mouse. Germ-free mice were inoculated with Composition B or a negative control by oral gavage and sacrificed following four weeks of colonization. Lamina propria leukocytes were isolated from colonic tissue of individual mice by standard procedures and assessed by flow cytometry. The regulatory T cell content was evaluated as the percentage of Foxp3-positive cells among CD4+ T cells.

As shown in FIG. 1, mice that were inoculated with Composition B were found to have significantly more regulatory T cells as compared to mice that were inoculated with the control.

Example 2: Composition B Suppresses IgE Antibody Production

Germ-free mice were inoculated with test consortia as in described in Example 1. Whole blood was collected into serum tubes at the time the mice were sacrificed and frozen until further analysis was performed. The serum was subsequently thawed, diluted 1:25, and total IgE in serum was measured using standard ELISA methods.

As shown in FIG. 2, the control germ-free (GF) mice had elevated serum IgE levels compared to specific pathogen-free (SPF) mice, which have a normal commensal microbiota. Colonization with composition B reduced serum IgE levels, indicating that the composition suppressed Th2-type inflammatory responses in the inoculated germ-free mice.

Example 3: Compositions B, C, and D Induce Regulatory T Cells and Suppress IgE Antibody Production Selected bacterial strains from Composition B were selected to form Compositions C and D, as shown in Tables 2 and 3. Each of the bacterial strains were grown, combined in the indicated combinations, and used to inoculate germ-free mice by oral gavage. The mice were sacrificed and lamina propria leukocytes were isolated and assessed as in Example 1. Whole blood was collected into serum tubes at the time of sacrifice and frozen until further analysis was performed.

TABLE 2

| | Composition C |
|---|---|
| Strain number | Bacterial strain |
| 1 | *Clostridium bolteae* |
| 2 | *Anaerotruncus colihominis* |
| 3 | *Sellimonas intestinales* |
| 4 | *Clostridium symbiosum* |
| 5 | *Blautia producta* |
| 7 | *Erysipelotrichaceae bacterium* |
| 8 | *Subdoligranulum* spp |

TABLE 3

| | Composition D |
|---|---|
| Strain number | Bacterial strain |
| 1 | *Clostridium bolteae* |
| 2 | *Anaerotruncus colihominis* |
| 3 | *Sellimonas intestinales* |
| 4 | *Clostridium symbiosum* |
| 5 | *Blautia producta* |
| 6 | *Dorea longicatena* |
| 8 | *Subdoligranulum* spp |

Figure 3:
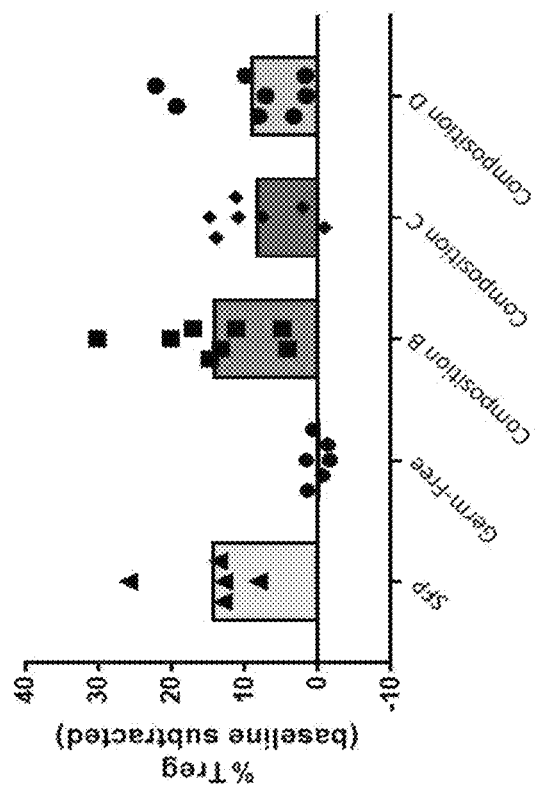
FIG. 3 shows the percentage of Foxp3+ CD4+ regulatory T cells (% Treg) induced in the intestine of germ-free mice inoculated with Composition B, Composition C, or Composition D, as compared to control mice ("Germ-Free") and specific-pathogen free mice ("SPF"). The data presented is cumulated from several independent experiments. To normalize between experiments, the average percentage of Foxp3-positive cells in the germ-free control mice was subtracted from each of the other mice in each experiment.

The regulatory T cell content was evaluated as the percentage of Foxp3-positive cells among CD4+ T cells. As shown in FIG. 3, Compositions B, C, and D were found to have more regulatory T cells as compared to mice that were inoculated with the control.

Figure 4:
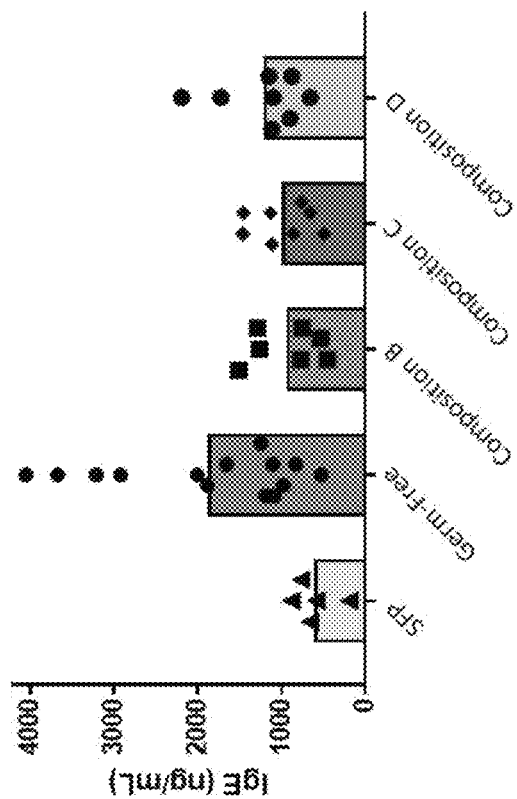
FIG. 4 shows the level of IgE antibodies in serum samples obtained from germ-free mice inoculated with Composition B, Composition C, or Composition D, as compared to control mice germ-free ("Germ-Free") and specific-pathogen free ("SPF") mice.

The serum samples were subsequently thawed, diluted, and total IgE in serum was measured using standard ELISA methods. As shown in FIG. 4, the control germ-free (GF) mice had elevated serum IgE levels compared to specific pathogen-free (SPF) mice, which have a normal commensal microbiota. Colonization with each of Compositions B, C, and D reduced serum IgE levels, indicating that the compositions suppressed Th2-type inflammatory responses in the inoculated germ-free mice.

Example 3: Decoupling Regulatory T Cell Induction and Butyrate Production

Both induction of regulatory T cells and production of butyrate have been proposed mechanisms by which immunoregulatory Clostridia may suppress inflammation (see, e.g., Atarashi et al., Treg induction by a rationally selected mixture of Clostridia strains from the human microbiota, *Nature*, 500 (7461): 232-236 (2013); Stefka et al., Commensal bacteria protect against food allergen sensitization, *Proceedings of the National Academy of Sciences of the United States*, 111 (36): 13145-13150 (2014)). To decouple these potential mechanisms, bacterial consortia were identified that were (1) predominantly butyrate producers with little Treg induction activity, or (2) high Treg inducers with no butyrate production. These consortia were then evaluated for their efficacy in protection from experimental food allergy.

Induction of Regulatory T Cells (Tregs)

The amount of Treg induction (TrIS) for bacterial strains was given a score as predicted by mathematical modeling. Bacterial consortia predicted to induce high, intermediate, and low level of Tregs were selected for experimental validation.

Briefly, germ-free C57BL/6 mice (age 5-6 weeks) were orally gavaged once with a bacterial composition at a dose $>=10^8$ CFU per mouse. Colonization was monitored over 4 weeks. At week 4, mice were sacrificed, and lamina propria leukocytes were isolated from the colon. The bacterial strains in the example bacterial compositions referred to as LBP1 and LBP2 are presented in Tables 4 and 5, respectively.

TABLE 4

LBP1

| Strain Number | Bacterial strain |
| --- | --- |
| 10 | VE202-9; *Clostridium indolis/Anaerostipes caccae* |
| 4 | VE202-16; *Clostridium symbiosum* |
| 11 | VE202-27; *Lachnospiraceae bacterium* |
| 13 | VE202-29; *Lachnospiraceae bacterium* |

TABLE 5

LBP2

| Strain Number | Bacterial strain |
| --- | --- |
| 9 | VE202-4; *Clostridium hathewayi* |
| 1 | VE202-7; *Clostridium bolteae* |
| 3 | VE202-14; *Sellimonas intestinalis* |
| 12 | VE202-28; *Clostridium* species |

Figure 5:
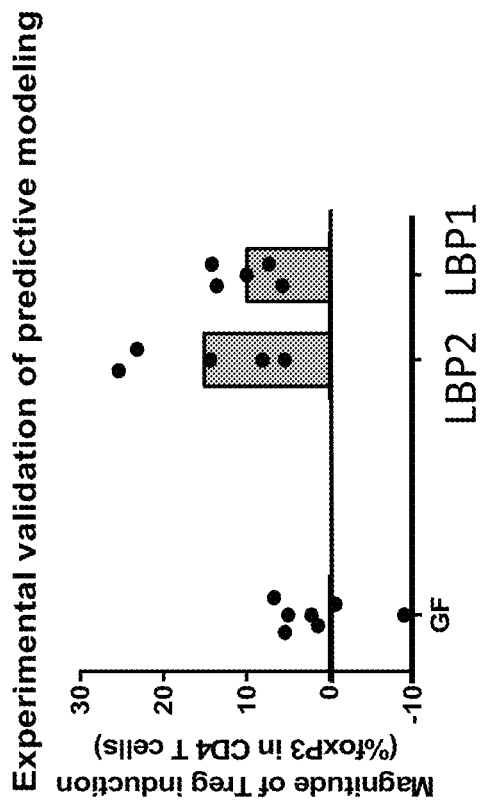
FIG. 5 shows the magnitude of regulatory T cell induction, measured as the percent of Foxp3+ CD4+ T cells (% foxP3 in CD4 T cells), in germ-free mice inoculated with LBP1 or LBP2, as compared to control mice ("GF").

As shown in FIG. 5, Tregs were quantified as Foxp3-positive CD4+ T cells. As predicted, administration of LBP2 resulted in higher levels of Treg induction and administration of LBP1 resulted in lower levels of Treg induction.

Short Chain Fatty Acid Production

Figure 6B:
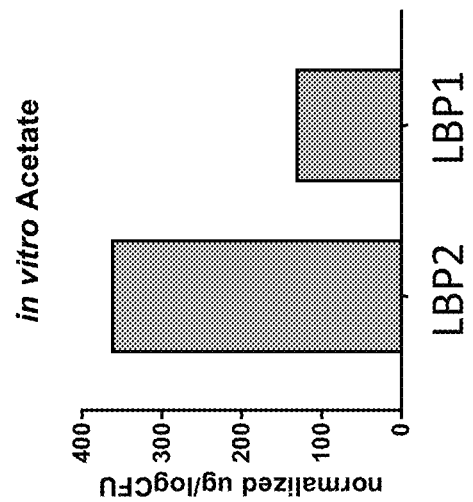
FIG. 6B shows the amount of acetate predicted to be produced in vitro by LBP1 or LBP2.
Figure 6A:
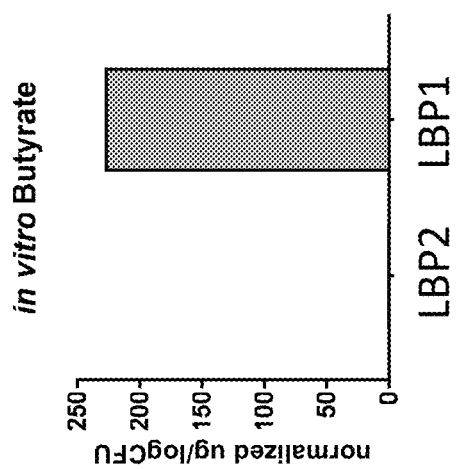
FIG. 6A shows the amount of butyrate predicted to be produced in vitro by LBP 2 or LBP 1.

Short chain fatty acid (SCFA) production by the bacterial compositions was assessed as described in Narushima et al. *Gut Microbes* (2014) 5(3): 333-339. Briefly, individual strains were grown to O.D.>0.3, supernatants were harvested, and colony forming unit (CFU) counts determined for each strain. The supernatants were sent for targeted metabolomic profiling of 7 short chain fatty acids and the results were normalized to CFU. FIGS. 6A and 6B show the predicted levels of butyrate and acetate produced by LBP1 and LBP2 based on the butyrate production by the individual strains of the composition. LBP1 was predicted to produce high levels of butyrate and low levels of acetate, whereas LBP2 was predicted to produce low levels of butyrate and high levels of acetate.

Figure 6C:
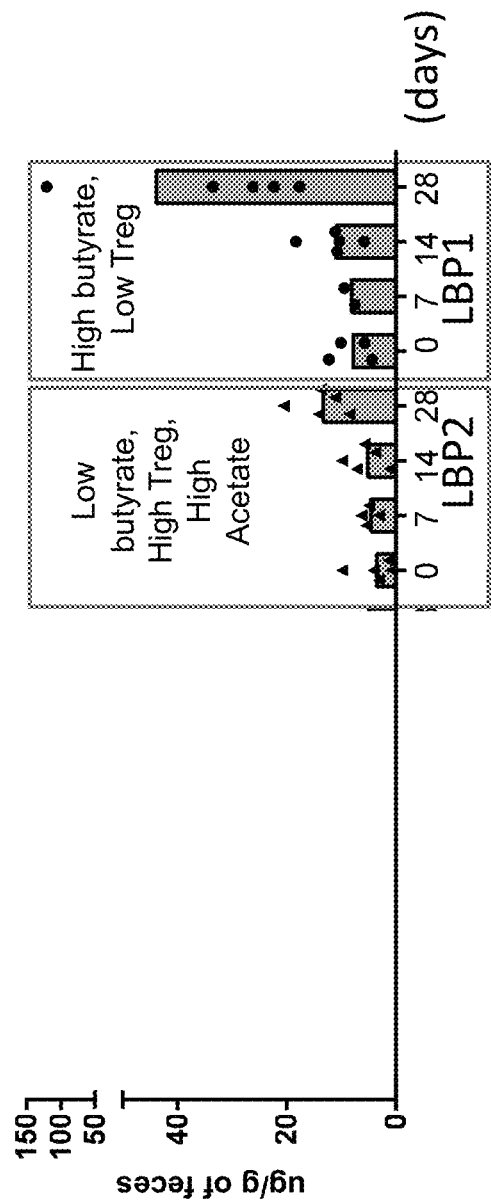
FIG. 6C shows the amount of butyrate produced in vivo, as measured in ex vivo stool samples from germ-free mice inoculated with LBP1 or LBP2.
Figure 6D:
FIG. 6D shows the amount of acetate produced in vivo, as measured in ex vivo stool samples from germ-free mice inoculated with LBP1 or LBP2.

The production of SCFA was also assessed in vivo in stool samples from mice inoculated with LBP1 or LBP2. Stool samples were collected at days 3, 7, 14, and 28 post colonization. As predicted, inoculation with LBP1 resulted in higher levels of butyrate and lower levels of acetate in the stool samples; and inoculation with LBP2 resulted in lower levels of butyrate and higher levels of acetate (FIGS. 6C and 6D).

Food Allergy Model

Figure 7:
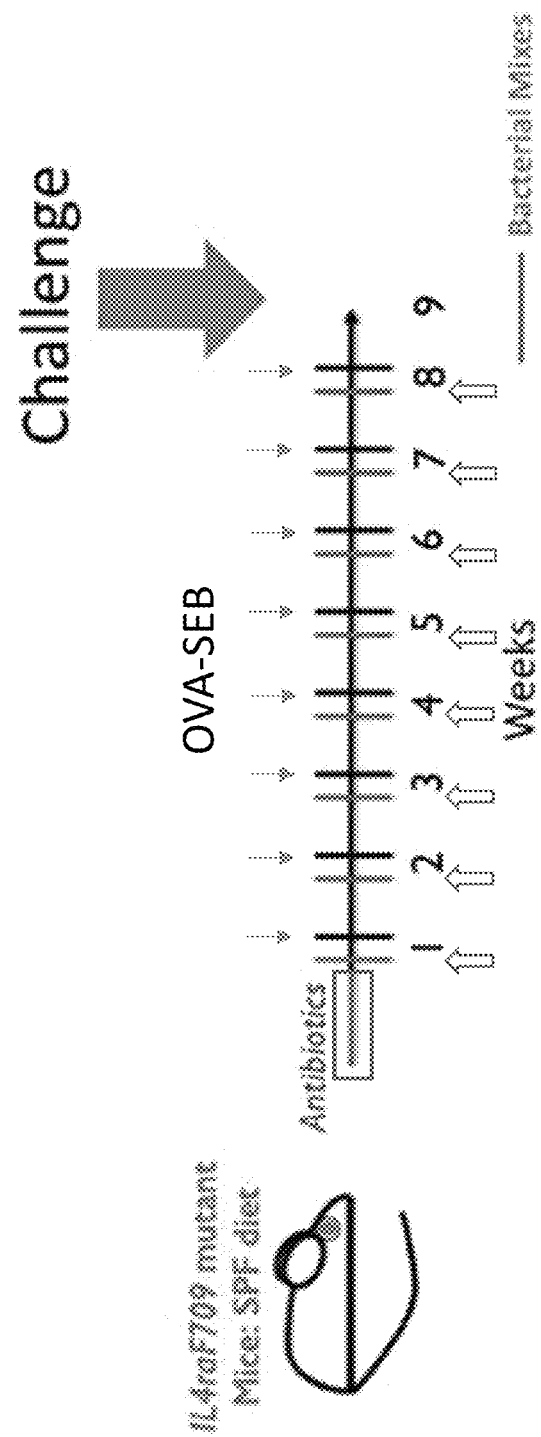
FIG. 7 is a schematic showing an experimental food allergy model as described in Example 3. The IL4raF709 mutant mice are pretreated with antibiotics during the time shown in a box. OVA+Staphylococcal enterotoxin B (SEB) are administered to the mice at the time points indicated by the arrows above the timeline. The bacterial mixtures are administered to the mice at the time points indicated by the open arrows below the timeline. The mice are challenged with OVA at the indicated time.

The bacterial compositions were evaluated in a mouse model of food allergy, as described, for example, in Mathias et al. *JACI* (2011) 127(3): 795-805. Briefly, IL4raF709 mice on Balb/c background have hyperresponsive IL4R signaling and may be used as a model for food allergy. These mice are genetically susceptible to anaphylaxis in response to food allergen sensitization. As shown in FIG. 7, the mice were pre-treated with antibiotics to create a niche for engraftment, followed by an 8 week sensitization with OVA (ovalbumin)+ SEB (staphylococcal enterotoxin B) and inoculation with the bacterial compositions. The mice were then challenged with OVA and evaluated.

To assess the immune response in the food allergy model, mice were bled at the 4 week intermediate time point, and the total serum IgE was measured. The challenge with OVA induces anaphylaxis and acute allergy in the IL4raF709 mice, which is measured by elevated serum total IgE, elevated serum OVA-specific IgE, elevated serum mMCP-1 (signal for mast cell degranulation), increased Th2 cells in the MLN and small intestine (staining for IL4 and other cytokines/transcription factors), increased Th2-like regulatory T cells (staining for IL4 and other cytokines/transcription factors (see Noval Rivas et al., Regulatory T cell reprogramming toward a Th2-cell-like lineage impairs oral tolerance and promotes food allergy, *Immunity*, 42 (3): 512-523 (2015)), and mast cell infiltration into the intestine (as measured by histology and cell isolation).

Figure 8D:
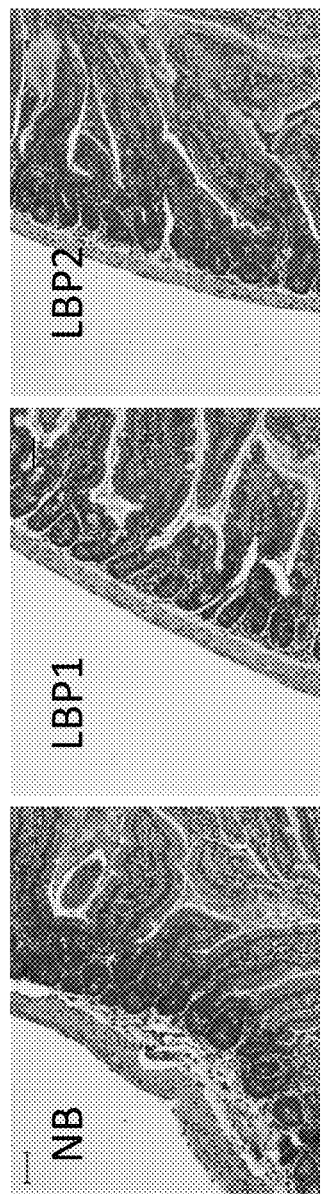
FIG. 8D shows micrographs of tissue samples from mice inoculated with LBP1, LBP2, or no bacteria ("NB").

LBP1 and LBP2 were found to have protective effects in the mouse model of food allergy that did not specifically depend on butyrate production. Inoculation with either LBP1 or LBP2 resulted in reduced levels of total IgE and OVA-specific IgE (FIGS. 8A and 8B). Additionally, mice that were administered LBP1 or LBP2 did not experience the temperature reduction that is observed in mice that did not receive the bacterial compositions (FIG. 8C). FIG. 8D shows representative micrographs of tissue samples from the mice.

Figure 9A:
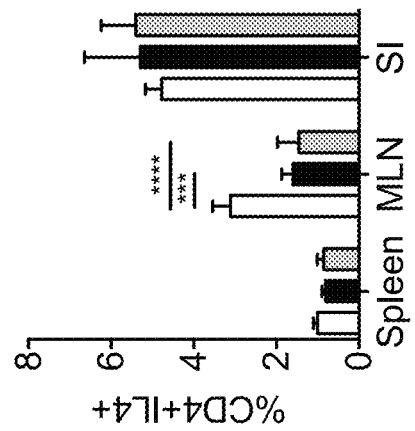
FIG. 9A shows the percentage of CD3+ CD4+ cells in the spleen, mesenteric lymph nodes (MLN), and small intestine (SI) of mice inoculated with LBP1 or LBP2, as compared to control mice (no bacteria).
Figure 9B:
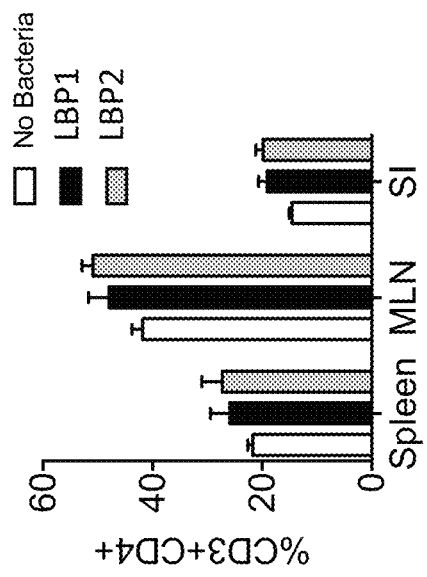
FIG. 9B shows the percentage of CD4+ IL4+ cells in the spleen, mesenteric lymph nodes (MLN), and small intestine (SI) of mice inoculated with LBP1 or LBP2, as compared to control mice (no bacteria).
Figure 9C:
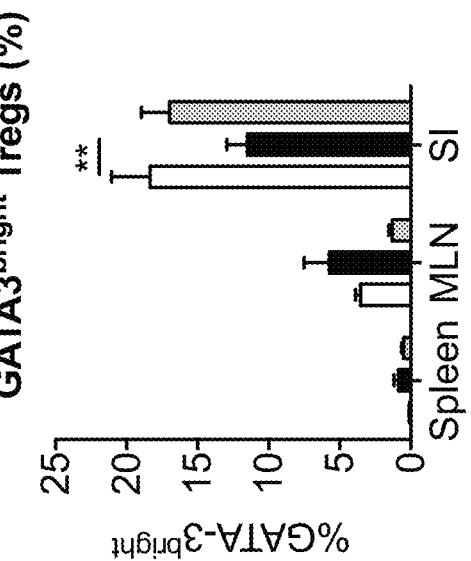
FIG. 9C shows the percentage of Foxp3+IL4+ in the spleen, mesenteric lymph nodes (MLN), and small intestine (SI) of mice inoculated with LBP1 or LBP2, as compared to control mice (no bacteria).
Figure 9D:
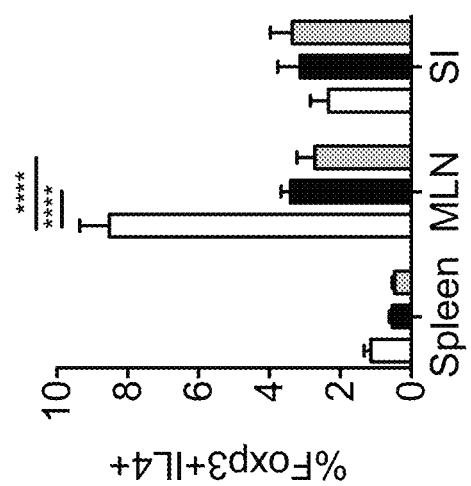
FIG. 9D shows the percentage of GATA3-bright regulatory T cells in the spleen, mesenteric lymph nodes (MLN), and small intestine (SI) of mice inoculated with LBP1 or LBP2, as compared to control mice (no bacteria). For each of FIGS. 9A-9D, white bars are control mice (no bacteria), black bars are mice inoculated with LBP1, and gray bars are mice inoculated with LBP2. , *, and **** represent statistical significance.

Mice that were inoculated with LBP1 or LBP2 were also found to have reduced allergy-associated T cell responses. In particular, IL-4 producing Th2 cells were reduced in the small intestine of mice that were administered LBP1 or LBP2, but the total CD4+ T cell population was not substantially changed (FIGS. 9A and 9B). Th2-phenotype regulatory T cells, including Foxp3+IL4+cells and GATA3+ (GATA3-bright) cells were also reduced in mice that were inoculated with LBP1 or LBP2 (FIGS. 9C and 9D).

Mast cells and IgE response were also evaluated as measures of protection from food allergy. As shown in FIGS. 10A-10D, mice that were inoculated with LBP1 or LBP2 were found to have reduced levels of mMCP-1, reduced numbers of mast cells, and reduced mast cell and B cell IgE. In sum, LBP1 and LBP2 were found to induce protection against food allergy, with reductions in allergy-associated T cells and granulocyte responses.

Figure 32:
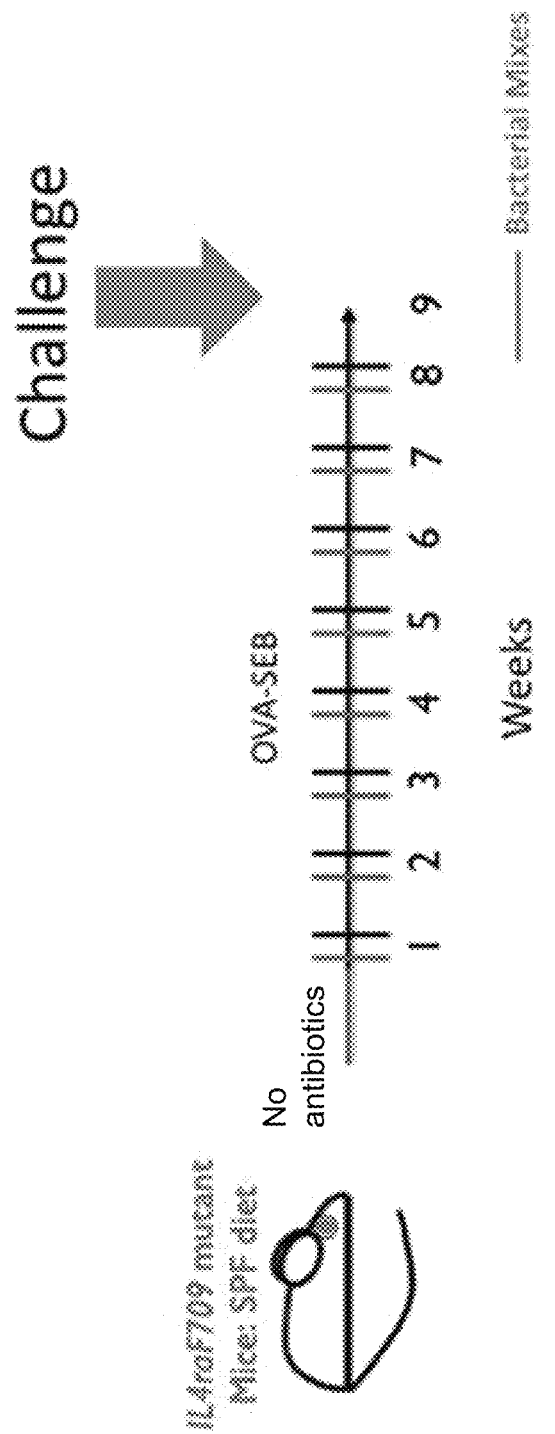
FIG. 32 shows a schematic of a preventative food allergy experimental model, similar to the experimental model shown in FIG. 7, however as indicated, the mice are not pre-treated with antibiotics prior to initiation of inoculation with the bacterial compositions.
Figure 33B:
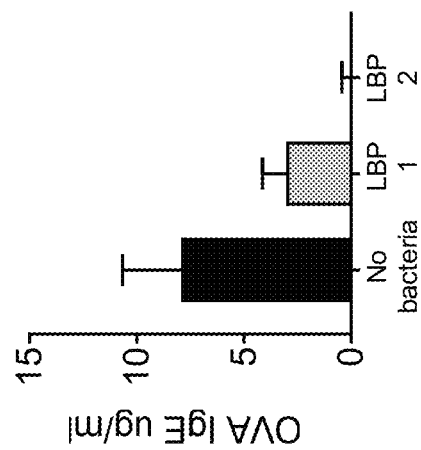
FIG. 33B shows an intermediate analysis of the level of OVA-specific IgE antibodies in serum samples obtained 5 weeks after initiation of inoculation of the bacterial compositions, at which time the mice have not yet been sensitized for the full 8 weeks and have not yet undergone the anaphylactic challenge. The results shown in FIGS. 33A and 33B were obtained using the preventative food allergy model shown in FIG. 32.
Figure 33A:
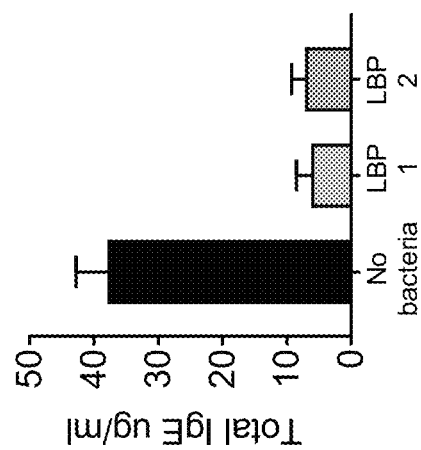
FIG. 33A shows an intermediate analysis of the level of IgE antibodies in serum samples obtained 5 weeks after initiation of inoculation of the bacterial compositions. Mice were inoculated with LBP 1, LBP 2, or no bacteria (control mice, "NB").
Figure 34B:
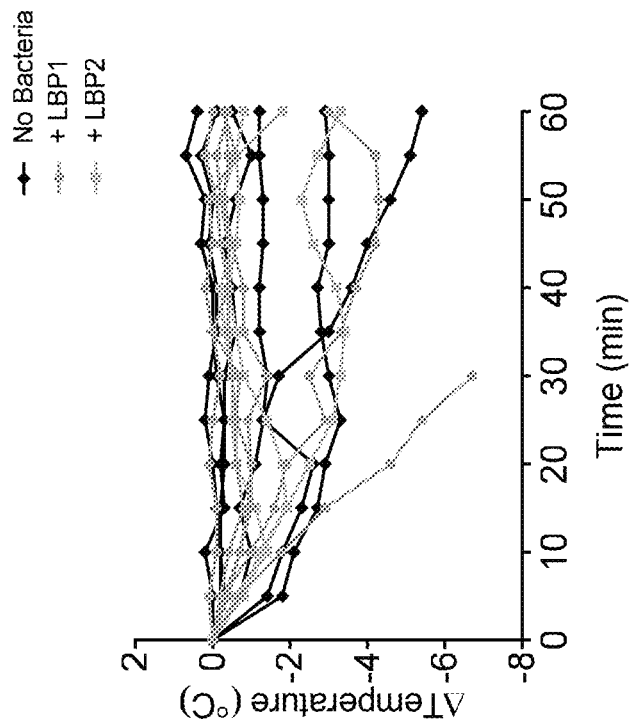
FIG. 34B shows the change in body temperature of individual mice inoculated with LBP1, LBP2, or control mice ("NB", no bacteria). SEM=standard error of the mean. The results shown in FIGS. 34A and 34B were obtained using the experimental model shown in FIG. 32.
Figure 34A:
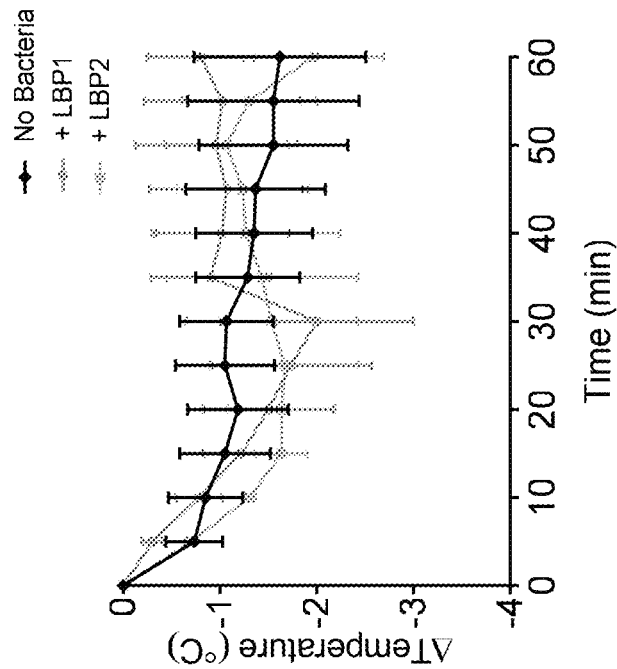
FIG. 34A shows the average change in body temperature (+/−SEM) of mice inoculated with LBP1, LBP2, or control mice ("NB", no bacteria).
Figure 35B:
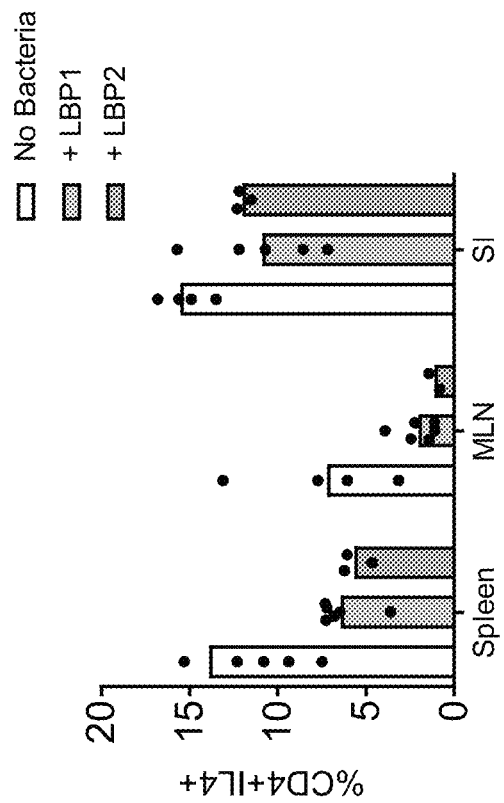
FIG. 35B shows the percentage of CD4+IL4+ (CD4+ Foxp3− IL4+) Th2 effector T cells in the spleen (Spleen), mesenteric lymph nodes (MLN), and small intestine (SI) of mice inoculated with LBP1, LBP2, or control mice ("No Bacteria"). The results shown in FIGS. 35A and 35B are from the same experiment as FIGS. 33A-34B.
Figure 35A:
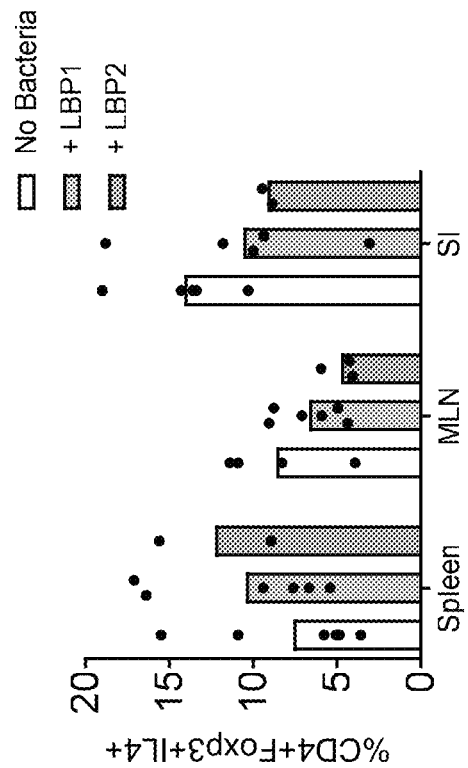
FIG. 35A shows for the percentage of CD4+ Foxp3+ IL4+ "Th2-type" regulatory T cells in the spleen (Spleen), mesenteric lymph nodes (MLN), and small intestine (SI) of mice inoculated with LBP1, LBP2, or control mice ("No Bacteria").

In a second experiment, it was evaluated whether pre-treatment with antibiotics was necessary to create a niche to facilitate engraftment of species from LBP1 and LBP2 and allow them to modulate the allergic response. This experiment was performed as described above, with the exception that no antibiotic pretreatment was performed (see, FIG. 32). Mice were bled at 5 weeks after the start of bacterial dosing, and as shown in FIGS. 33A and 33B, both LBP1 and LBP2 reduced the rate of allergic sensitization as measured by reduced total and OVA-specific IgE in the serum. When anaphylactic responses were measured following 8 weeks of sensitization and bacterial treatment, LBP1 and LBP2 treatment were insufficient to protect against experimental anaphylaxis as measured by temperature drop (FIGS. 34A and 34B). However, measures of allergy-associated T cell responses suggested that treatment with LBP1 and LBP2 had some immunomodulatory effect, with reductions in Th2-phenotype regulatory T cells (FIG. 35A, Foxp3+IL4+ cells) in MLN and small intestine, and reductions in Th2 cells (FIG. 35B, Foxp3−IL4+cells) in spleen, MLN, and small intestine.

Evaluation of Additional Bacterial Compositions

Based on the results observed using LBP1 and LBP2, Compositions B, C, and D were also evaluated for production of SCFA, Treg induction, and protection from food allergy.

As described above, bacterial strains from Compositions B, C, and D were assessed for production of butyrate and acetate in vitro. The levels of production of butyrate and acetate for each composition were predicted based on the production of the individual strains. Compositions B, C, and D were predicted to have similar levels of butyrate production as LBP1 (FIGS. 11A and 11B). This was confirmed in vivo for Composition B and Composition C (FIGS. 11C and 11D). Compositions B, C, and D were predicted to have higher levels of butyrate production than LBP2 (FIGS. 12A and 12B). This was confirmed in vivo for Composition B and Composition C (FIGS. 12C and 12D).

Figure 13:
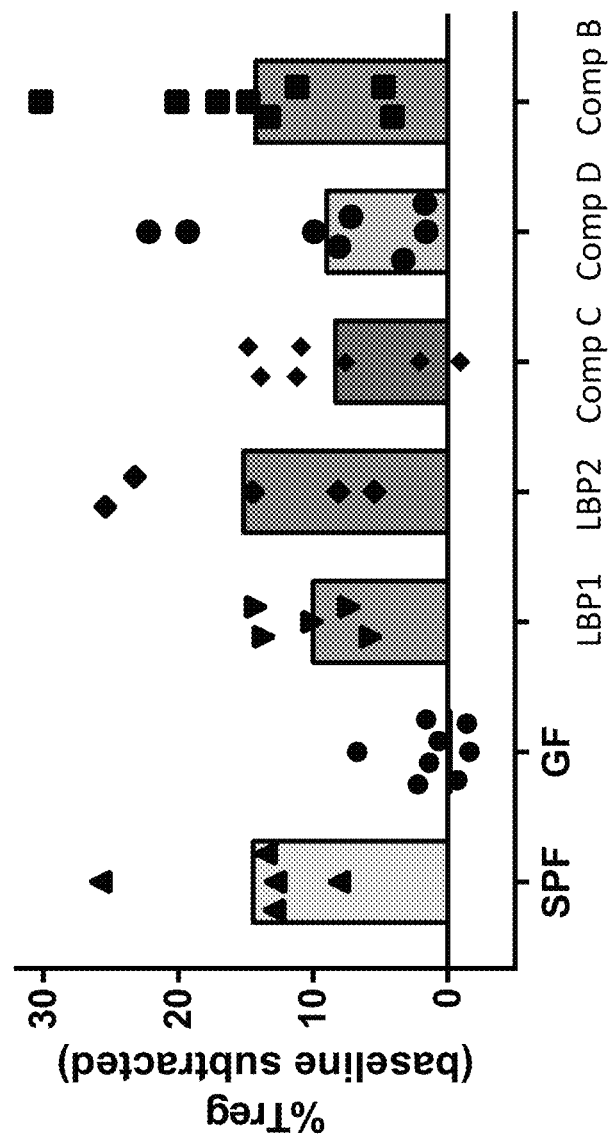
FIG. 13 shows the percentage of Foxp3+ CD4+ regulatory T cells (% Treg) induced in the intestine of germ-free mice inoculated with LBP1, LBP2, Composition C, Composition D, or Composition B, as compared to control mice ("GF") and specific-pathogen free mice ("SPF"). The data presented is cumulated from several independent experiments. To normalize between experiments, the average percentage of Foxp3-positive cells in the germ-free control mice was subtracted from each of the other mice in each experiment.
Figure 14:
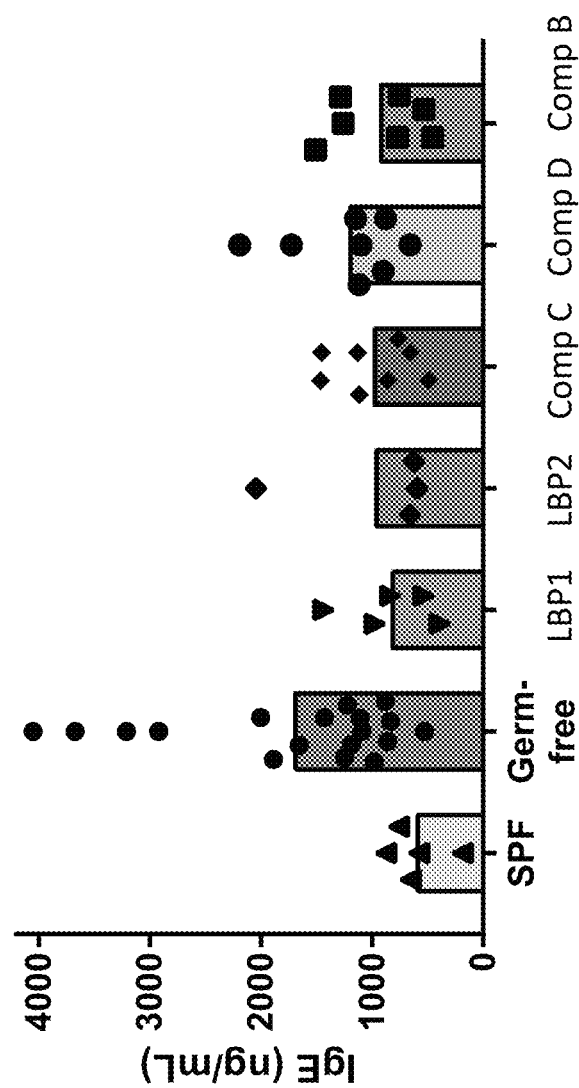
FIG. 14 shows the level of IgE antibodies in serum samples obtained from germ-free mice inoculated with LBP1, LBP2, Composition C, Composition D, or Composition B, as compared to control mice germ-free ("Germ-free") and specific-pathogen free ("SPF") mice.

Inoculation of germ-free mice with the bacterial compositions resulted in similar levels of Treg induction (FIG. 13). IgE levels were found to be reduced to a similar extent in germ-free mice inoculated with the compositions (FIG. 14).

Figure 15B:
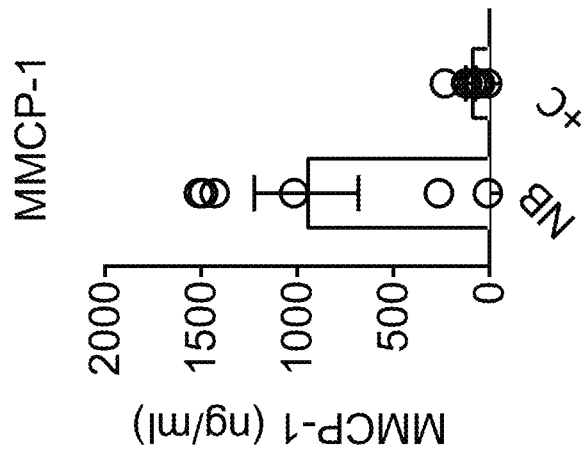
FIG. 15B shows the level of mMCP-1 (MMCP-1) in serum samples from mice inoculated with Composition C, as compared to control mice (no bacteria, "NB"). The results shown in FIGS. 15A and 15B were obtained from the experimental food allergy model shown in FIG. 7.
Figure 15A:
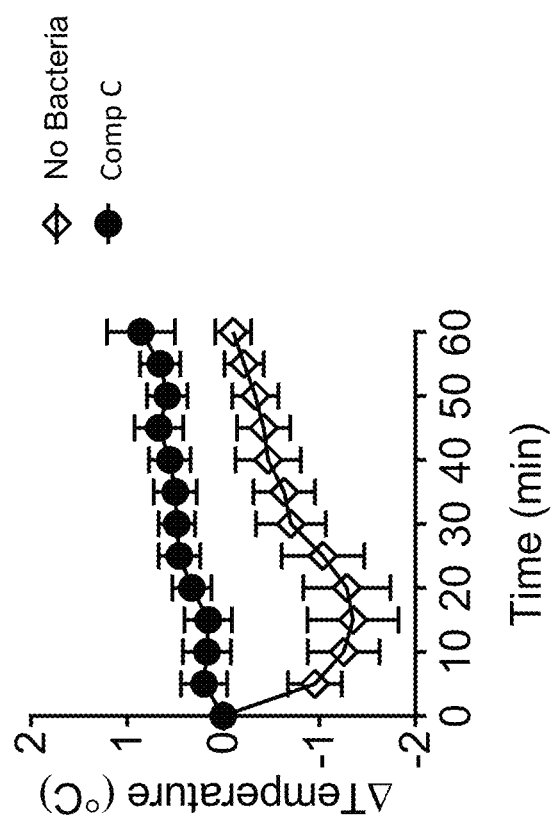
FIG. 15A shows the change in body temperature of mice inoculated with Composition C or control mice (no bacteria).
Figure 16E:
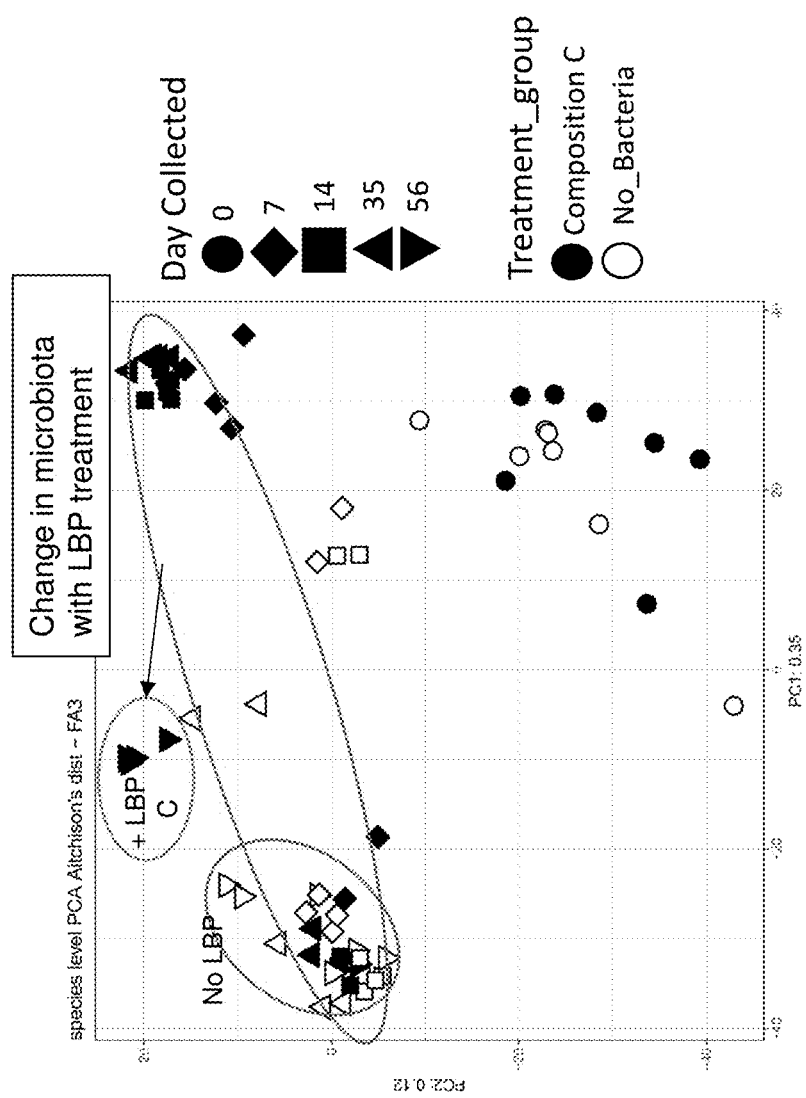
FIG. 16E presents a plot of the microbial communities by Principal Component Analysis (PCA) of species showing fecal microbiome profiles and changes to the microbiome resulting from inoculation with Composition C during allergic sensitization. The microbial species are shown for mice on Day 0 (prior to antibiotic treatment), Day 7 (following antibiotic treatment and prior to inoculation with Composition C), and at Days 14, 35, and 56 during the course of weekly allergen sensitization and inoculation with Composition C ("+Composition C"). The results shown in FIGS. 16A-16E are for the same experiment shown in FIGS. 15A and 15B.
Figure 18E:
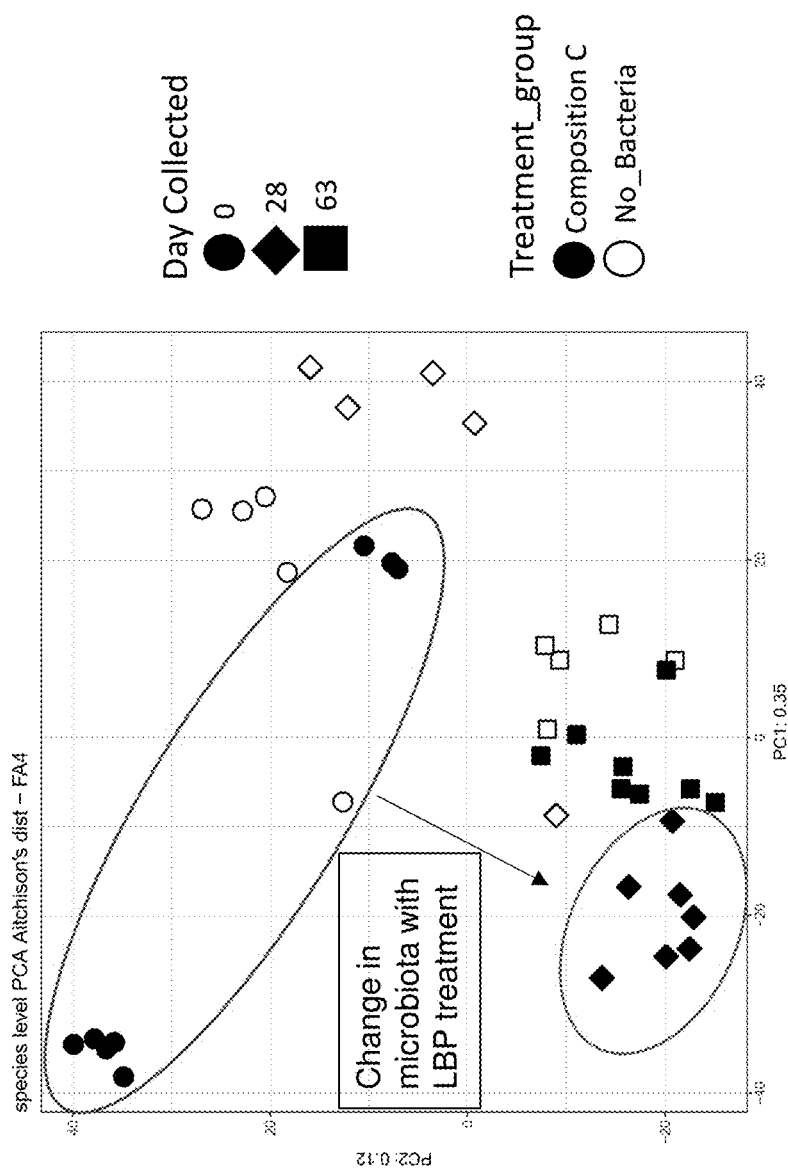
FIG. 18E presents a plot of the microbial communities by Principal Component Analysis (PCA) of species showing fecal microbiome profiles and changes to the microbiome resulting from inoculation with Composition C during allergic sensitization. The microbial species are shown for mice on Day 0 (prior to antibiotic treatment and prior to inoculation with Composition C), and at Days 28 and 63 during the course of weekly allergen sensitization and inoculation with Composition C ("+C"). The results shown in FIGS. 18A-18E are for the same experiment shown in FIGS. 17A-17C.
Figure 27C:
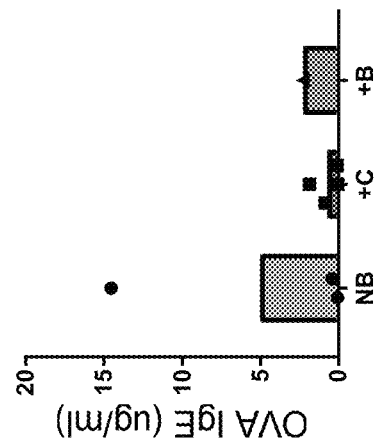
FIG. 27C shows the level of OVA-specific IgE antibodies in serum samples obtained from mice in a curative food allergy model that were inoculated with Composition C (+C) or Composition B (+B) as compared to control mice (no bacteria, "NB"). The results of FIGS. 27A-27C were obtained using the food allergy experimental model shown in FIG. 19.
Figure 27B:
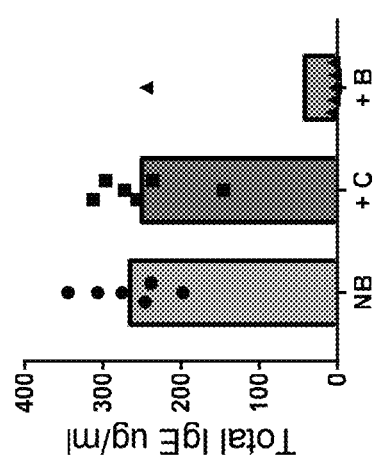
FIG. 27B shows the level of total IgE antibodies in serum samples obtained from mice in a curative food allergy model that were inoculated with Composition C (+C), Composition B (+B), or control mice (no bacteria, "NB").
Figure 27A:
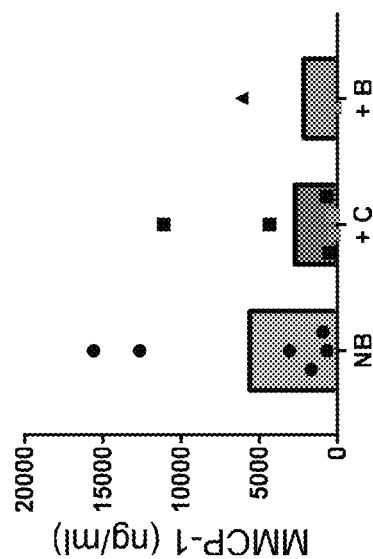
FIG. 27A shows the level of mMCP-1 (MMCP-1) in serum samples from mice in a curative food allergy model that were inoculated with Composition C (+C), Composition B (+B), or control mice (no bacteria, "NB").
Figures 28A, 28B:
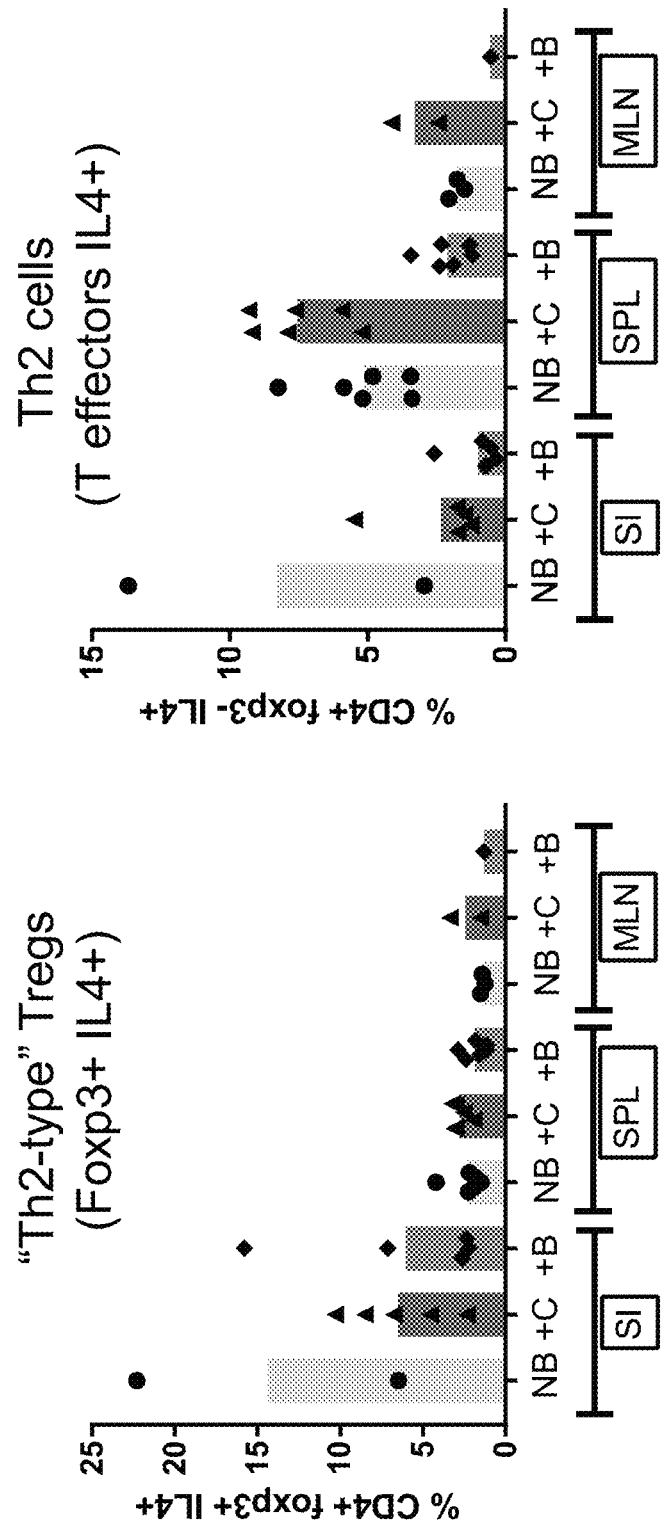
FIG. 28A shows the percentage of CD4+ Foxp3+ IL4+ "Th2-type" regulatory T cells (% CD4+foxp3+IL4+) in the small intestine (SI), spleen (SPL), and mesenteric lymph nodes (MLN) of mice inoculated with Composition C ("+C"), Composition B ("+B"), or control mice (no bacteria, "NB").
FIG. 28B shows the percentage of CD4+ Foxp3− IL4+ Th2 effector T cells (% CD4+foxp3-IL4+) in the small intestine (SI), spleen (SPL), and mesenteric lymph nodes (MLN) of mice inoculated with Composition C ("+C"), Composition B ("+B"), or control mice (no bacteria, "NB"). The results for FIGS. 28A and 28B are from the same experiment as FIGS. 26A-27C.

Compositions B and C were further evaluated in the mouse model of food allergy. Mice that were inoculated with Composition C did not experience the temperature reduction observed in mice that did not receive the bacterial compositions, suggesting that the mice that received Composition C were protected from anaphylaxis upon allergen challenge (FIGS. 15A, 17A, and 17B). Confirming this point, as shown in FIGS. 15B 17C, and 27A, mice that were inoculated with Composition C were also found to have reduced levels of mMCP-1 as compared to mice that did not receive bacteria. In one experiment, as shown in FIGS. 16A-D, treatment with Composition C led to increased numbers of total Tregs (CD4+Foxp3+) in mesenteric lymph nodes, spleen and small intestine, and reduced numbers of allergy-associated IL4-positive Th2 effectors (Foxp3−IL4+), Th2-like GATA3+ Tregs (Foxp3+GATA3+), and Th2 GATA3+ T effectors (Foxp3−GATA3+) in the small intestine. In another experiment, mice treated with Composition C exhibited reductions in Th2-like Tregs (Foxp3+GATA3+) and Th2 effector cells (Foxp3−GATA3+ in the spleen (FIGS. 18A, 18B). In another experiment, mice treated with Compositions B and C exhibited reductions in Th2-like Tregs (Foxp3+IL4+) in the small intestine, and reductions in Th2 effector cells (Foxp3-IL4+) in mLN and small intestine. Levels of total IgE and OVA-specific IgE were also assessed, and compositions B and C reduced OVA-specific IgE antibodies (FIGS. 27B and 27C and FIGS. 26A-28B).

In the experiments shown in FIGS. 16A-16D, 18A, and 18B, DNA was isolated from fecal pellets at various time points and whole genome shotgun sequencing was performed on the Illumina platform, followed by quality control and taxon assignment. Inoculation with Composition C was associated with global shifts in the intestinal microbiome (FIGS. 16E and 18E).

Additional Characterization

Samples obtained from mice inoculated with any of the compositions described herein may also be evaluated for levels of IL-33, IL25, TSLP (e.g., transcript in the intestinal tract), TGFβ, IL-10. Alternatively, or in addition, the mice may be assessed for relative colonization (e.g., engraftment) of the compositions, including one or more strains of the composition. Samples obtained from mice may also be subjected to RNAseq, or other expression analysis.

The effects of engrafted strains on host immune and biochemical responses and on gut barrier integrity may also be assessed. Stool fractions from mice that were inoculated with any of the compositions described herein may be subjected to deconvolution to identify beneficial strains, which may undergo further characterization including whole genome sequencing, metabolite production profiling, Treg induction potential, gut barrier integrity enhancement potential. In addition, in silico analysis may be conducted to determine the abundance and prevalence of one or more strains in healthy subjects, co-occurrence networks, and whether one or more bacterial strains are associated with favorable clinical responses in subjects undergoing oral immunotherapy.

Figure 19:
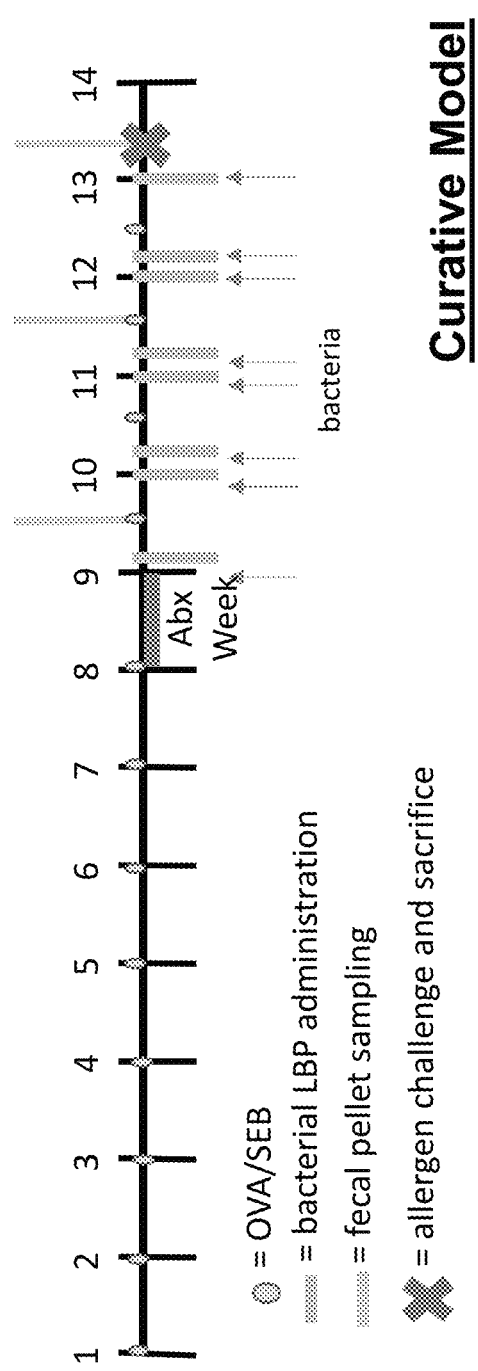
FIG. 19 is a schematic showing a curative experimental food allergy model as described in Example 4. The IL4raF709 mutant mice are sensitized for 8 weeks with OVA+Staphylococcal enterotoxin B (SEB), followed by pretreatment with antibiotics ("Abx") for one week as indicated. The bacterial mixtures are administered to the mice at the time points indicated by the arrows below the timeline.
Figure 21A:
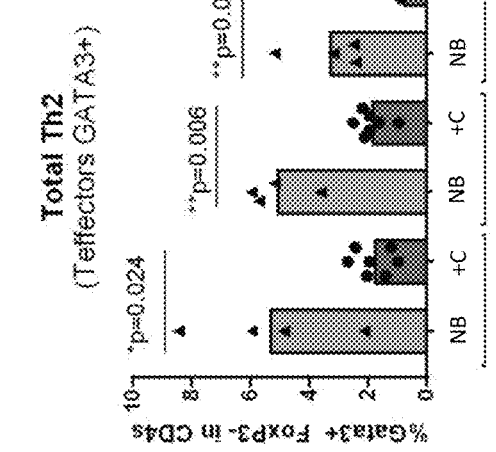
FIG. 21A shows the percentage of FoxpP3+ GATA3+ "Th2-type" regulatory T cells (% Foxp3+GATA3+) in the mesenteric lymph nodes (MLN), spleen (SPL), and small intestine (Sm Int) of mice inoculated with Composition C (+C), as compared to control mice (no bacteria, "NB").
Figure 21C:
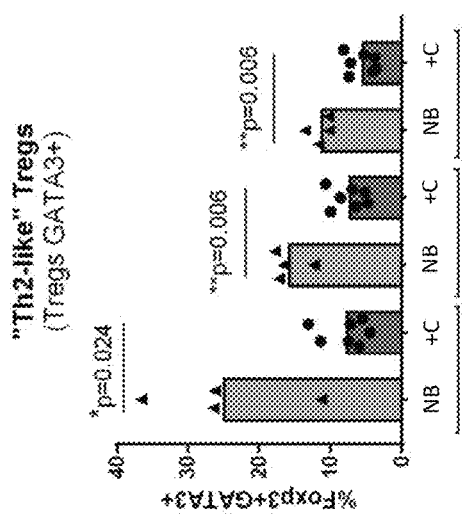
FIG. 21C shows the percentage of total Foxp3+ regulatory T cells (% FoxP3+ Tcells) in the mesenteric lymph nodes (MLN), spleen (SPL), and small intestine (Sm Int) of mice inoculated with Composition C (+C), as compared to control mice (no bacteria, "NB").
Figure 21B:
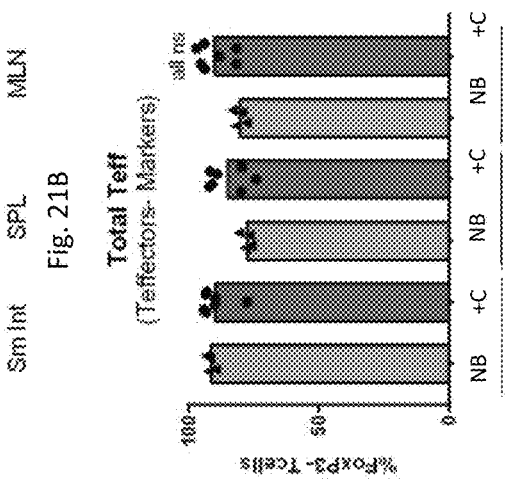
FIG. 21B shows the percentage of Foxp3−GATA3− Th2 effector T cells (% Gata3+ FoxP3-in CD4s) in the mesenteric lymph nodes (MLN), spleen (SPL), and small intestine (Sm Int) of mice inoculated with Composition C (+C), as compared to control mice (no bacteria, "NB").
Figure 21D:
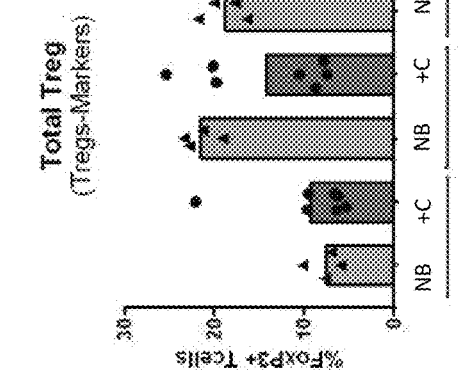
FIG. 21D shows the percentage of total Foxp3− effector T cells (% FoxP3-Tcells) in the mesenteric lymph nodes (MLN), spleen (SPL), and small intestine (Sm Int) of mice inoculated with Composition C (+C), as compared to control mice (no bacteria, "NB"). The results shown in FIGS. 21A-21D are for the same experiment shown in FIGS. 20A-20C.
Figures 22A, 22B:
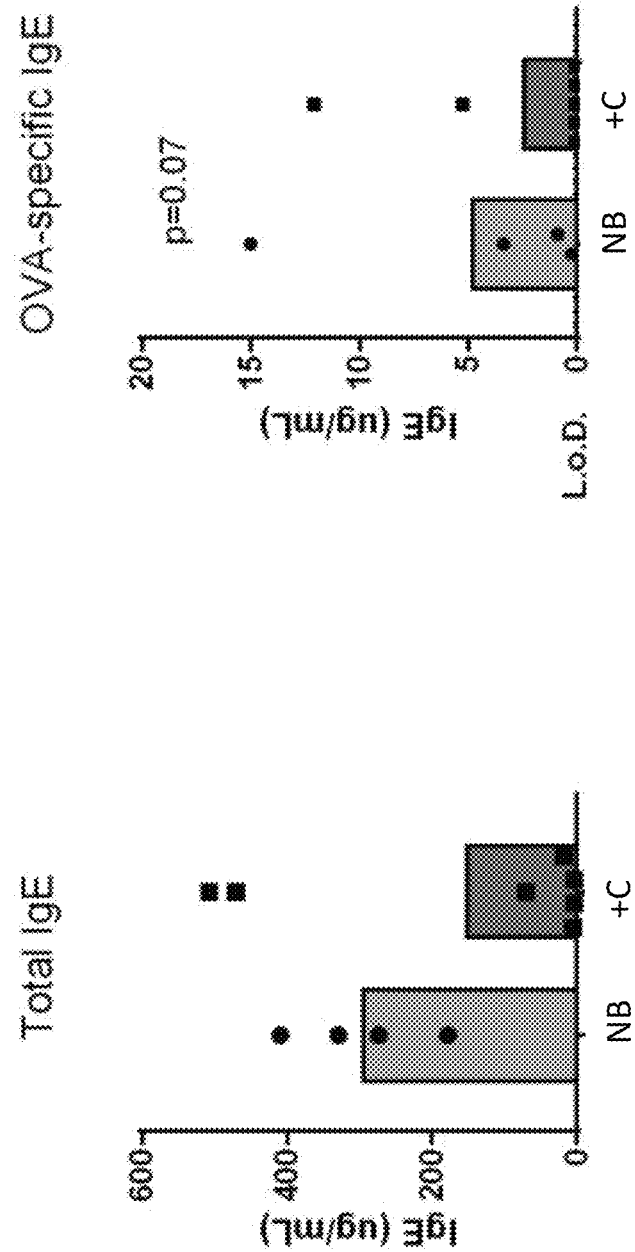
FIG. 22A shows the level of total IgE antibodies in serum samples obtained from mice inoculated with Composition C (+C), as compared to control mice (no bacteria, "NB").
FIG. 22B shows the level of OVA-specific IgE antibodies in serum samples obtained from mice inoculated with Composition C (+C), as compared to control mice (no bacteria, "NB"). The results shown in FIGS. 22A-22B are for the same experiment shown in FIGS. 20A-20C.

Example 4: Evaluating Composition C and Composition B as a Treatment for Food Allergy The efficacy of Compositions C and B as a treatment for food allergy was evaluated. Bacterial Compositions C and B were evaluated in a "curative" mouse model for treating food allergy, as described, for example, in PCT Publication No. WO 2017/079450. Briefly, IL4raF709 mice on Balb/c background have hyperresponsive IL4R signaling and may be used as a model for food allergy. These mice are genetically susceptible to anaphylaxis in response to food allergen sensitization. As shown in FIG. 19, the mice were sensitized with OVA (ovalbumin)+SEB (Staphylococcal enterotoxin B) for 8 weeks. The mice were then pre-treated with antibiotics to create a niche for engraftment, followed by bi-weekly inoculation with the bacterial compositions for 4 weeks (8 total inoculations). During this period, the mice continue to be sensitized with OVA+SEB administration. The mice were then challenged with OVA and evaluated.

The immune response was assessed in the curative food allergy model following the full 12 week model. The challenge with OVA induces anaphylaxis and acute allergy in the IL4raF709 mice, which is measured by elevated serum total IgE, elevated serum OVA-specific IgE, elevated serum mMCP-1 (signal for mast cell degranulation), increased Th2 cells and Th2-like Treg cells in the mesenteric lymph nodes, small intestine, and spleen.

Figure 23B:
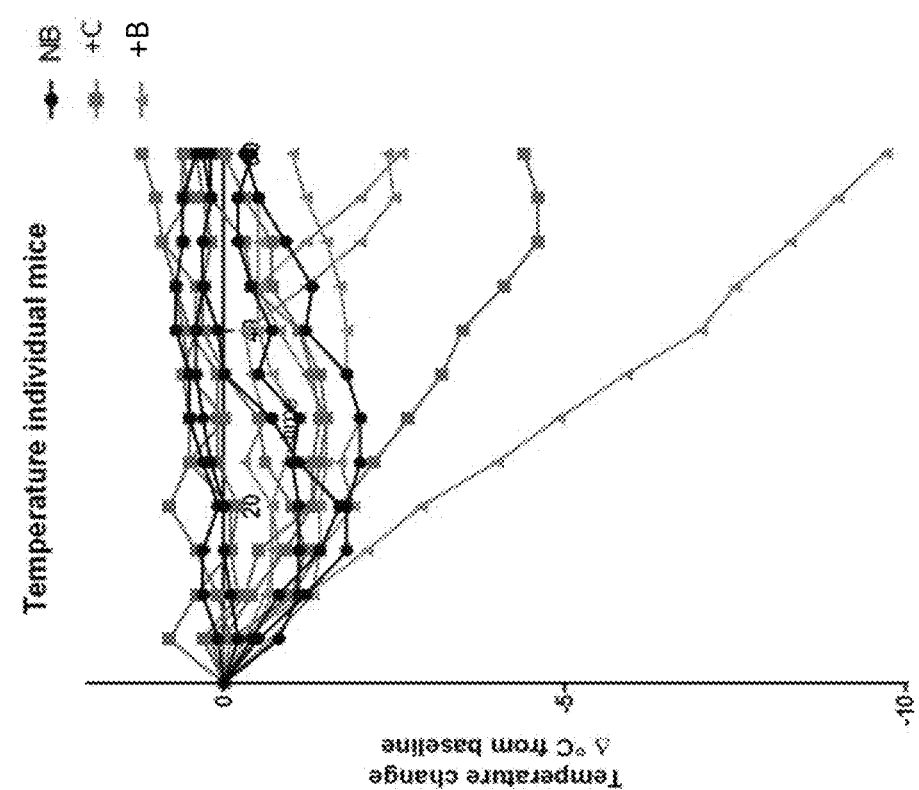
FIG. 23B shows the change in body temperature of individual mice inoculated with Composition C (+C), Composition B (+B), or control mice ("NB", no bacteria). SEM=standard error of the mean. The results shown in FIGS. 23A-23B were obtained from the experimental food allergy model shown in FIG. 19.
Figure 23A:
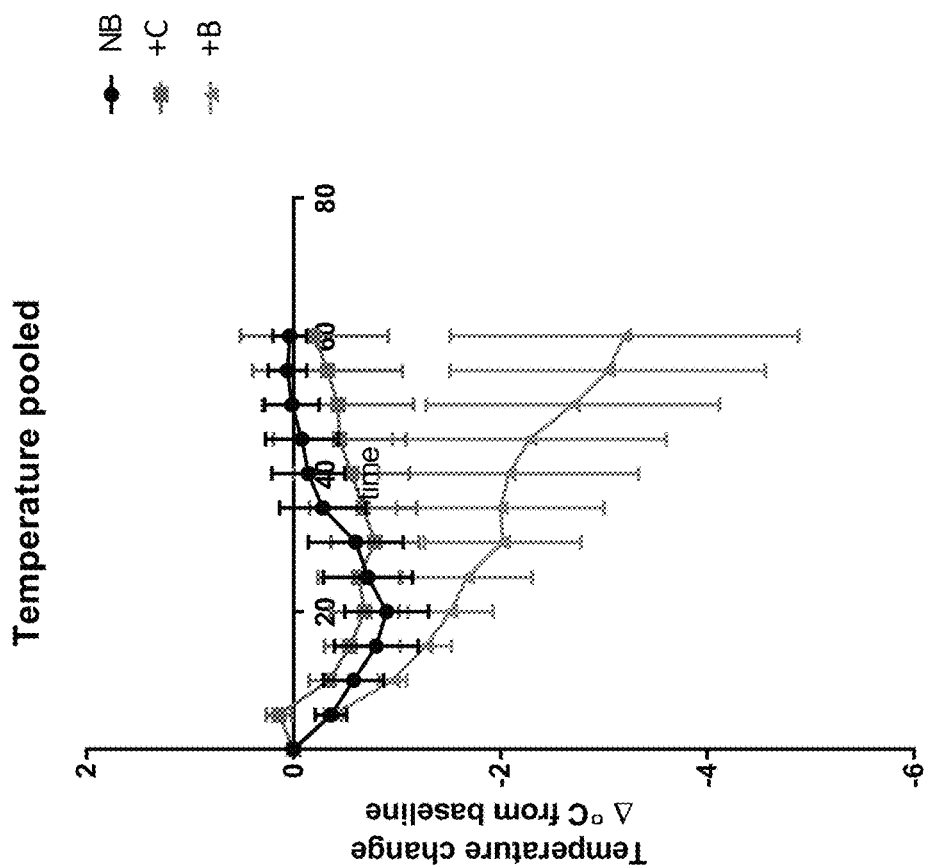
FIG. 23A shows the average change in body temperature (+/−SEM) of mice inoculated with Composition C (+C), Composition B (+B), or control mice ("NB", no bacteria).
Figure 24A:
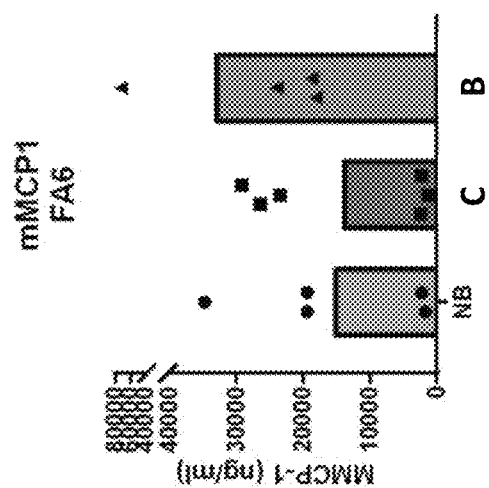
FIG. 24A shows the level of mMCP-1 (MMCP-1) in serum samples from curative food allergy model mice inoculated with Composition C (C) or Composition B (B) compared to control mice (no bacteria, "NB").
Figure 24B:
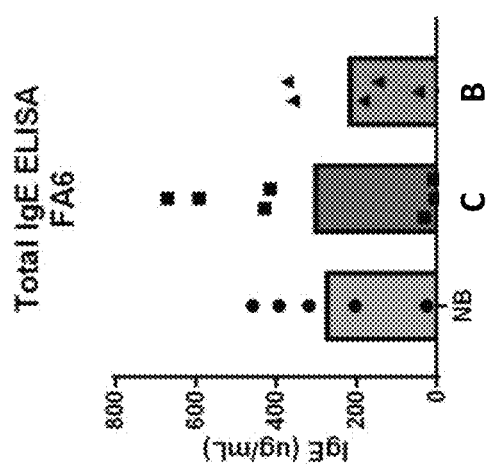
FIG. 24B shows the level of IgE antibodies in serum samples obtained from curative food allergy model mice inoculated with Composition C (C) or Composition B (B) as compared to control mice (no bacteria, "NB").
Figure 24C:
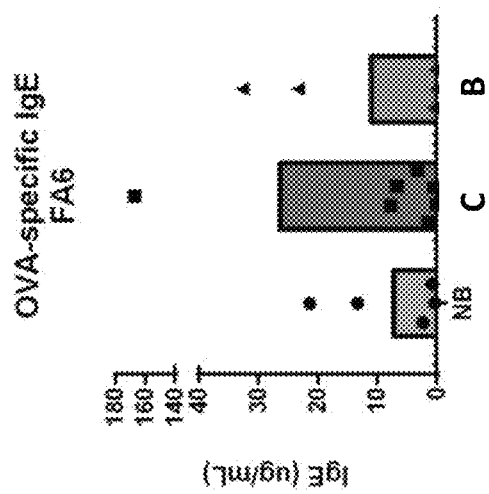
FIG. 24C shows the level of OVA-specific IgE antibodies in serum samples obtained from model mice inoculated with Composition C (C) or Composition B (B) as compared to control mice (no bacteria, "NB").
Figure 26B:
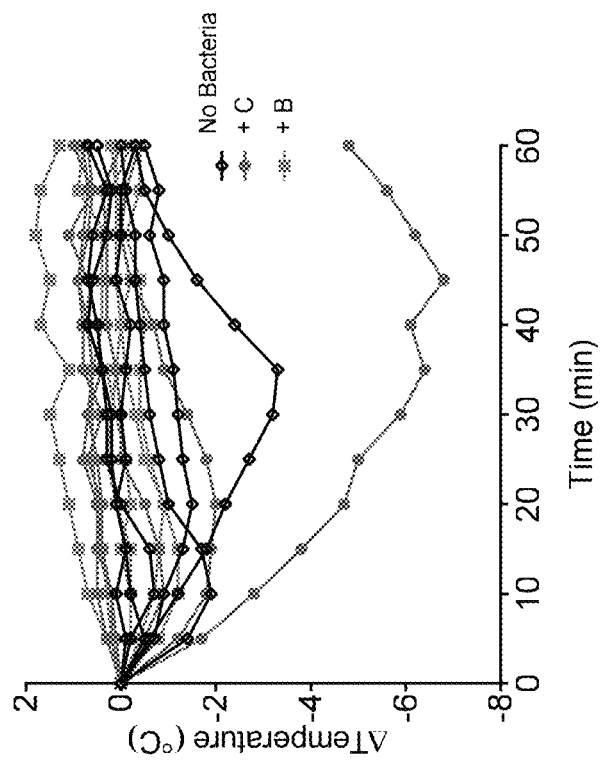
FIG. 26B shows the change in body temperature of individual mice inoculated with Composition C (+C), Composition B (+B), or control mice ("No Bacteria"). SEM=standard error of the mean. The results for FIGS. 26A and 26B are from the same experimental food allergy model shown in FIG. 7.
Figure 26A:
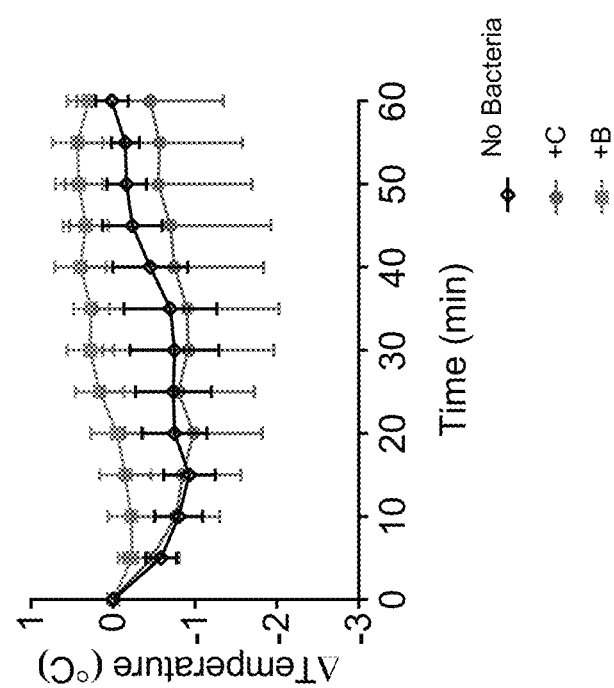
FIG. 26A shows the average change in body temperature (+/−SEM) of mice inoculated with Composition C (+C), Composition B (+B), or control mice ("No Bacteria").

Compositions C and B were evaluated in the curative mouse model of treating food allergy. Mice that were inoculated with Composition C did not experience the temperature reduction that was observed in mice that were inoculated with Composition B or mice that did not receive the bacterial compositions, suggesting that the mice that received Composition C were protected from developing an allergic response to OVA challenge (FIGS. 20A, 20B, 23A, 23B). In particular, 7 of the 14 mice administered Composition C showed no effect of exposure to the allergen, whereas all of the control mice experienced anaphylaxis (FIGS. 20B and 23B). As shown in FIGS. 20C and 24A, mice that were inoculated with Composition C and protected from anaphylaxis were also found to have reduced levels of mMCP-1 compared with mice that did not receive the bacterial compositions and underwent anaphylaxis. Furthermore, reduced numbers of allergy-associated Th2 effectors (CD4+FoxP3−GATA3+) and Th2-like Tregs (CD4+Foxp3+GATA3+), were observed in mice administered Composition C as compared to mice administered Composition B or mice that were not administered the bacterial compositions (FIGS. 21A-21D and FIGS. 25A-25D). Finally, mice that were inoculated with Composition C and were protected from anaphylaxis had reduced levels of total IgE antibodies and antigen-specific OVA-IgE antibodies as compared to mice that were not administered the bacterial compositions and underwent anaphylaxis (FIGS. 22A, 22B, 24B, and 24C).

Example 5: Modulation of Pre-Existing Host Microbiome and Intestinal Immunity by Compositions B and C Germ-free mice, such as those used in Examples 1-3 herein, lack a resident microbiota and have an altered immune system compared to conventional mice, including a relative lack of intestinal regulatory T cells and elevated Th2-type immune responses. Having demonstrated that Compositions B and C preferentially induce regulatory T cell responses in germ-free mice, it was then investigated whether these bacterial compositions were capable of inducing immunoregulatory effects in mice possessing a resident microbiota and a normal immune system. It was further explored whether pre-treatment with antibiotics was necessary to create a niche to facilitate engraftment of species of Compositions B and C and allow them to modulate intestinal immunity, or whether the bacterial compositions could have effects in the absence of antibiotics.

Figure 29:
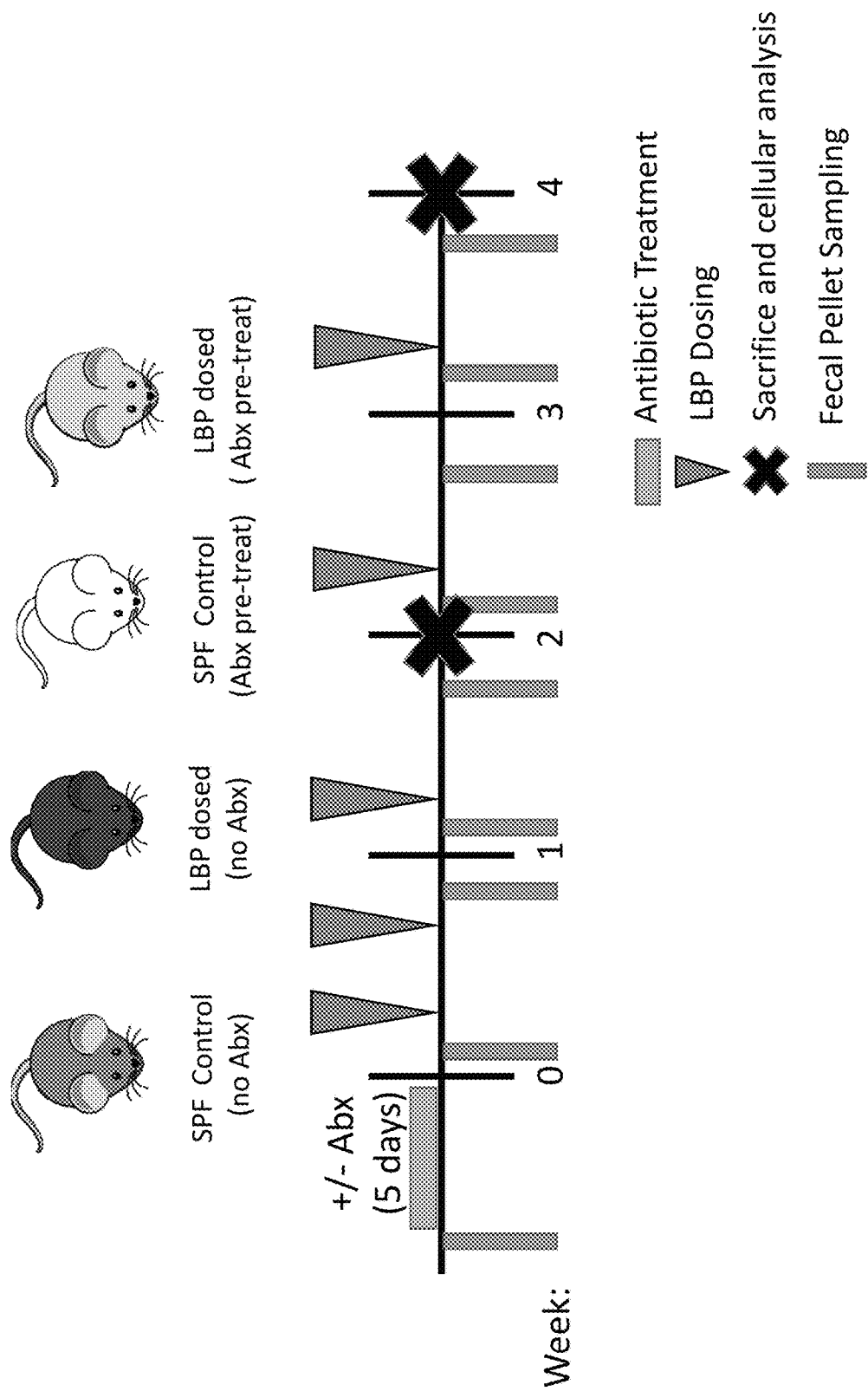
FIG. 29 is a schematic showing an experimental allergy model with which to assay the ability of a bacterial composition to influence the host microbiome and intestinal immune response. Specific pathogen free ("SPF") mice are either treated or not with antibiotics for 5 consecutive days, as indicated by the horizontal bar. Following a 2-3 day "washout" period, mice are either inoculated with bacterial compositions (either fresh or frozen preparations of bacterial compositions, as indicated by arrows) or not inoculated (control mice). Dosing with the bacterial compositions occurs twice in the first week and continues weekly, with intermittent fecal pellet collection to monitor bacterial colonization and fecal microbiome (as indicated by vertical bars). Groups of mice are sacrificed at 2 and 4 weeks to monitor intestinal immune responses (indicated by black "X").

Specific pathogen free (SPF) mice having reached immunological maturity (6-8 weeks old) were used to evaluate such effects of Compositions B and C. Mice were treated with cefoperazone (5 mg/mouse) or untreated by daily oral gavage for five days, followed by a three-day wash-out period. FIG. 29. This is an adaptation of a standard method of treatment to reduce the resident intestinal microbiota and facilitate bacterial engraftment (see, for example, Schubert et al (2015) mBio). Mice were then inoculated with Composition B, Composition C, or untreated. The mice that received the bacterial compositions were continued weekly inoculations.

Figure 30B:
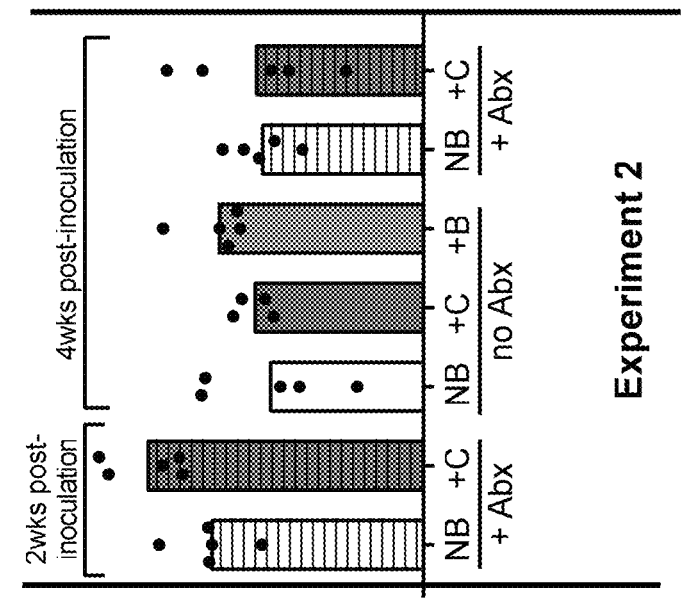
FIG. 30A shows the percentage of total CD4+ T cells that were FoxP3+ and Helios-among live CD45+ lamina propria leukocytes isolated from the colon of mice that were treated with antibiotics ("+Abx") or no antibiotics ("no Abx"), inoculated with Composition B ("+B"), or no bacteria ("NB"), and sacrificed at either two or four weeks post initiation of bacterial inoculation.
FIG. 30 B shows the percentage of total CD4+ T cells that were FoxP3+ and Helios− among live CD45+ lamina propria leukocytes isolated from the colon of mice that were treated with antibiotics ("+Abx") and inoculated with Composition C ("+C"), or no bacteria ("NB"); received no antibiotics ("no Abx") and were inoculated with Composition C ("+C"), Composition B ("+B"), or no bacteria ("NB"). Mice were at either two or four weeks post initiation of bacterial inoculation. The results of FIGS. 30A and 30B were obtained from the experimental model shown in FIG. 29.
Figure 30A:
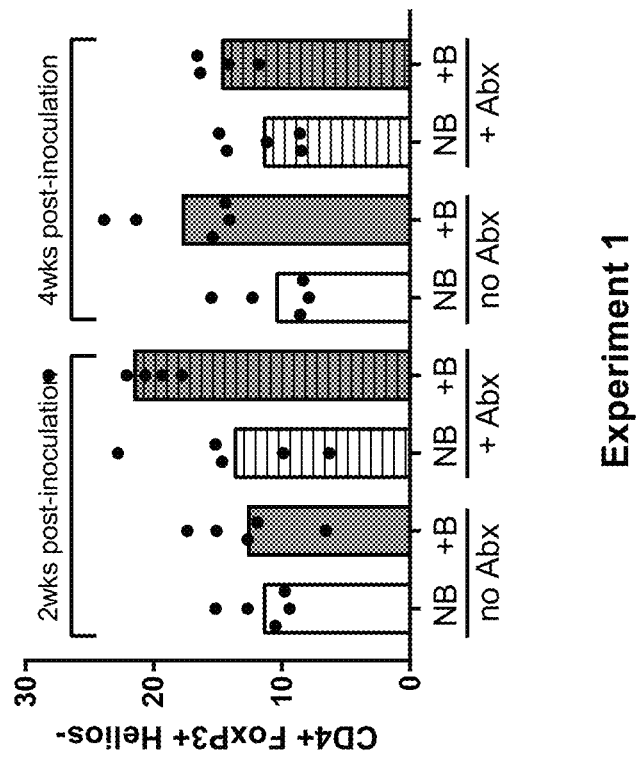

Subsets of mice from each experimental group were sacrificed at 2 and 4 weeks, and leukocytes were isolated from colonic tissue to evaluate induction of immunoregulatory responses. As shown in FIG. 30A, in mice that were pre-treated with antibiotics, Composition B induced Tregs in the colon, defined as CD4+ FoxP3+ Helios− T cells, above the "no bacteria" baseline at 2 and 4 weeks. When mice were not treated with antibiotics, Composition B induced Tregs in the colon, but the increase above baseline was only observed after four weeks of bacterial treatment. Similarly, as shown in FIG. 30A, in mice that were pre-treated with antibiotics, Composition C induced Tregs in the colon above the "no bacteria" control baseline. In the absence of antibiotic treatment, both Composition B and C showed a trend toward induction of colonic Tregs after 4 weeks of bacterial dosing. These experiments suggest that Compositions B and C are capable of inducing regulatory immune responses in the intestine even in the context of a microbiota-sufficient host with normal immune development.

Because these results suggested that Composition B and C had an effect in the intestine even in mice with an existing resident microbiota, the microbial community in the intestine of experimental mice was examined from Experiment 1 (from FIG. 30A). Fecal pellets were sampled from mice that were not treated with antibiotics before bacterial dosing (Day 0), after 2 bacterial doses (Day 13), after 3 bacterial doses (Day 20), and after 5 doses, prior to sacrifice (Day 34) (FIG. 31A). Principal component analysis (PCA) was conducted on the microbiome community composition of each sample to examine the microbiome dynamics during LBP treatment and allergic sensitization (see, e.g., Zinkernagel, et al., Association of the intestinal microbiome with the development of neovascular age-related macular degeneration, *Scientific Reports,* 7: 40826 (2017)). PCA analysis revealed that for untreated mice (no bacteria), the microbial community had a similar profile over the course of the experiment. However, for mice that were inoculated with Composition B ("LBP"), there was a shift in the microbiota over time as compared to baseline, suggesting that, even without antibiotic treatment, inoculation with Composition B led to changes in the resident microbiota. Similar results were observed in mice that received antibiotic pretreatment (FIG. 31B). For the mice that received antibiotic pretreatment, fecal pellets were collected before antibiotic treatment (Day 0), after antibiotics and prior to inoculation with LBP (Day 6), after 2 inoculations with the bacterial compositions (Day 13), after 3 inoculations with the bacterial compositions (Day 20), and after 5 inoculations with the bacterial compositions and prior to sacrifice (Day 34). In all mice, treatment with antibiotics induced a notable change in the microbiota from baseline (day 0) to day 6. For mice that were not inoculated with Composition B, dysbiosis was maintained, and the microbial profile was permanently altered and never returned to baseline. For mice that were inoculated with Composition B, the microbial profile began to return over time to pre-antibiotic baseline, suggesting that Composition B led to changes in the resident microbiota, and that these changes may promote return to healthy homeostasis.

What is claimed is:

1. A method of treating a food allergy, comprising orally administering to a subject in need thereof a therapeutically effective amount of a composition comprising a purified bacterial mixture consisting of 7 bacterial strains each comprising one of 16S rDNA sequences having at least 99.5% sequence identity to SEQ ID NOs: 1-5, 7, and 8, wherein there is 1 strain comprising each of the 16S rDNA sequences having at least 99.5% sequence identity to SEQ ID NOs: 1-5, 7, and 8.

2. The method of claim 1, wherein the subject is administered an antibiotic prior to administration of the composition.

3. The method of claim 2, wherein the antibiotic is vancomycin.

4. The method of claim 1, wherein the food allergy is selected from the group consisting of a nut allergy, a fish allergy, a wheat allergy, a milk allergy, a peanut allergy, a tree nut allergy, a shellfish allergy, a soy allergy, a seed allergy, a sesame seed allergy, and an egg allergy.

5. The method of claim 1, wherein the food allergy is a peanut allergy.

6. The method of claim 1, wherein one or more of the bacterial strains are in spore form.

7. The method of claim 1, wherein one or more of the bacterial strains are lyophilized.

8. The method of claim 1, wherein all of the bacterial strains are lyophilized.

9. The method of claim 1, wherein one or more of the bacterial strains are spray-dried.

10. The method of claim 1, wherein all of the bacterial strains are spray-dried.

11. The method of claim 1, wherein the bacterial strains originate from more than one human donor.

12. The method of claim 1, wherein the composition is in the form of a capsule.

13. The method of claim 1, wherein the composition further comprises one or more enteric polymers.

14. The method of claim 1, wherein the composition further comprises one or more adjuvants.

15. The method of claim 3, wherein vancomycin is administered in 4 doses of 125 mg vancomycin per day for 5 days.

* * * * *

SEQUENCE LISTING

```
<160> NUMBER OF SEQ ID NOS: 13

<210> SEQ ID NO 1
<211> LENGTH: 1530
<212> TYPE: DNA
<213> ORGANISM: Clostridium bolteae

<400> SEQUENCE: 1
atgagagttt gatcctggct caggatgaac gctggcggcg tgcctaacac atgcaagtcg    60
```

```
aacgaagcaa ttaaaatgaa gttttcggat ggattttttga ttgactgagt ggcggacggg      120
tgagtaacgc gtggataacc tgcctcacac tgggggataa cagttagaaa tgactgctaa      180
taccgcataa gcgcacagta ccgcatggta cggtgtgaaa aactccggtg gtgtgagatg      240
gatccgcgtc tgattagcca gttggcgggg taacggccca ccaaagcgac gatcagtagc      300
cgacctgaga gggtgaccgg ccacattggg actgagacac ggcccaaact cctacgggag      360
gcagcagtgg ggaatattgc acaatgggcg aaagcctgat gcagcgacgc cgcgtgagtg      420
aagaagtatt tcggtatgta aagctctatc agcaggaag aaaatgacgg tacctgacta      480
agaagccccg gctaactacg tgccagcagc cgcggtaata cgtaggggc aagcgttatc      540 cggatttact gggtgtaaag ggagcgtaga cggcgaagca gtctgaagt gaaaacccag      600 ggctcaaccc tgggactgct ttggaaactg ttttgctaga gtgtcggaga ggtaagtgga      660
attcctagtg tagcggtgaa atgcgtagat attaggagga acaccagtgg cgaaggcggc      720
ttactggacg ataactgacg ttgaggctcg aaagcgtggg gagcaaacag gattagatac      780
cctggtagtc cacgccgtaa acgatgaatg ctaggtgttg gggggcaaag cccttcggtg      840
ccgtcgcaaa cgcagtaagc attccacctg gggagtacgt tcgcaagaat gaaactcaaa      900
ggaattgacg gggacccgca caagcggtgg agcatgtggt ttaattcgaa gcaacgcgaa      960
gaaccttacc aagtcttgac atcctcttga ccggcgtgta acggcgcctt cccttcgggg     1020
caagagagac aggtggtgca tggttgtcgt cagctcgtgt cgtgagatgt tgggttaagt     1080
cccgcaacga gcgcaaccct tatccttagt agccagcagg taaagctggg cactctaggg     1140
agactgccag ggataacctg gaggaaggtg gggatgacgt caaatcatca tgccccttat     1200
gatttgggct acacacgtgc tacaatggcg taaacaaagg gaagcaagac agtgatgtgg     1260
agcaaatccc aaaaataacg tcccagttcg gactgtagtc tgcaacccga ctacacgaag     1320
ctggaatcgc tagtaatcgc gaatcagaat gtcgcggtga atacgttccc gggtcttgta     1380
cacaccgccc gtcacaccat gggagtcagc aacgcccgaa gtcagtgacc caactcgcaa     1440
gagagggagc tgccgaaggc ggggcaggta actggggtga agtcgtaaca aggtagccgt     1500
atcggaaggt gcggctggat cacctccttt                                       1530

<210> SEQ ID NO 2
<211> LENGTH: 1522
<212> TYPE: DNA
<213> ORGANISM: Anaerotruncus colihominis

<400> SEQUENCE: 2
tcaaagagtt tgatcctggc tcaggacgaa cgctggcggc gcgcctaaca catgcaagtc       60
gaacggagct acgttttga agttttcgga tggatgaatg taagcttagt ggcggacggg      120
tgagtaacac gtgagcaacc tgcctttcag aggggataa cagccggaaa cggctgctaa      180
taccgcatga tgttgcgggg gcacatgccc ctgcaaccaa aggagcaatc cgctgaaaga      240
tgggctcgcg tccgattagc cagttggcgg ggtaacggcc caccaaagcg acgatcggta      300
gccggactga gaggttgaac ggccacattg ggactgagac acggcccaga ctcctacggg      360
aggcagcagt gggggatatt gcacaatggg cgaaagcctg atgcagcgac gccgcgtgag      420
ggaagacggt cttcggattg taaacctctg tctttgggga agaaaatgac ggtacccaaa      480
gaggaagctc cggctaacta cgtgccagca gccgcggtaa tacgtaggga gcaagcgttg      540
tccggaatta ctgggtgtaa agggagcgta ggcgggatgg caagtagaat gttaaatcca      600
```

| | |
|---|---:|
| tcggctcaac cggtggctgc gttctaaact gccgttcttg agtgaagtag aggcaggcgg | 660 |
| aattcctagt gtagcggtga aatgcgtaga tattaggagg aacaccagtg gcgaaggcgg | 720 |
| cctgctgggc tttaactgac gctgaggctc gaaagcgtgg ggagcaaaca ggattagata | 780 |
| ccctggtagt ccacgccgta aacgatgatt actaggtgtg gggggactga ccccttccgt | 840 |
| gccgcagtta acacaataag taatccacct ggggagtacg gccgcaaggt tgaaactcaa | 900 |
| aggaattgac gggggcccgc acaagcagtg gagtatgtgg tttaattcga agcaacgcga | 960 |
| agaaccttac caggtcttga catcggatgc atagcctaga gataggtgaa gcccttcggg | 1020 |
| gcatccagac aggtggtgca tggttgtcgt cagctcgtgt cgtgagatgt tgggttaagt | 1080 |
| cccgcaacga gcgcaaccct tattattagt tgctacgcaa gagcactcta atgagactgc | 1140 |
| cgttgacaaa acgaggaag gtggggatga cgtcaaatca tcatgcccct tatgacctgg | 1200 |
| gctacacacg tactacaatg gcactaaaac agagggcggc gacaccgcga ggtgaagcga | 1260 |
| atcccgaaaa agtgtctcag ttcagattgc aggctgcaac ccgcctgcat gaagtcggaa | 1320 |
| ttgctagtaa tcgcggatca gcatgccgcg gtgaatacgt tcccgggcct tgtacacacc | 1380 |
| gcccgtcaca ccatgggagt cggtaacacc cgaagccagt agcctaaccg caagggggc | 1440 |
| gctgtcgaag gtgggattga tgactggggt gaagtcgtaa caaggtagcc gtatcggaag | 1500 |
| gtgcggctgg atcacctcct tt | 1522 |

<210> SEQ ID NO 3
<211> LENGTH: 1529
<212> TYPE: DNA
<213> ORGANISM: Ruminococcus torques

<400> SEQUENCE: 3

| | |
|---|---:|
| tacgagagtt tgatcctggc tcaggatgaa cgctggcggc gtgcctaaca catgcaagtc | 60 |
| gagcgaagcg ctgttttcag aatcttcgga ggaagaggac agtgactgag cggcggacgg | 120 |
| gtgagtaacg cgtgggcaac ctgcctcata caggggata acagttagaa atgactgcta | 180 |
| ataccgcata agcgcacagg accgcatggt gtagtgtgaa aaactccggt ggtatgagat | 240 |
| ggacccgcgt ctgattaggt agttggtggg gtaaaggcct accaagccga cgatcagtag | 300 |
| ccgacctgag agggtgaccg gccacattgg gactgagaca cggcccaaac tcctacggga | 360 |
| ggcagcagtg gggaatattg cacaatgggg gaaaccctga tgcagcgacg ccgcgtgaag | 420 |
| gaagaagtat ttcggtatgt aaacttctat cagcagggaa gaaaatgacg gtacctgagt | 480 |
| aagaagcacc ggctaaatac gtgccagcag ccgcggtaat acgtatggtg caagcgttat | 540 |
| ccggatttac tgggtgtaaa gggagcgtag acggataggc aagtctggag tgaaaaccca | 600 |
| gggctcaacc ctgggactgc tttggaaact gcagatctgg agtgccgag aggtaagcgg | 660 |
| aattcctagt gtagcggtga aatgcgtaga tattaggagg aacaccagtg gcgaaggcgg | 720 |
| cttactggac ggtgactgac gttgaggctc gaaagcgtgg ggagcaaaca ggattagata | 780 |
| ccctggtagt ccacgccgta aacgatgact actaggtgtc ggtgtgcaaa gcacatcggt | 840 |
| gccgcagcaa acgcaataag tagtccacct ggggagtacg ttcgcaagaa tgaaactcaa | 900 |
| aggaattgac ggggacccgc acaagcggtg gagcatgtgg tttaattcga agcaacgcga | 960 |
| agaaccttac ctggtcttga catccggatg acgggcgagt aatgtcgccg tcccttcggg | 1020 |
| gcgtccgaga caggtggtgc atggttgtcg tcagctcgtg tcgtgagatg ttgggttaag | 1080 |
| tcccgcaacg agcgcaaccc ttatcttcag tagccagcat ataaggtggg cactctggag | 1140 |
| agactgccag ggagaacctg gaggaaggtg gggatgacgt caaatcatca tgccccttat | 1200 |

```
ggccagggct acacacgtgc tacaatggcg taaacaaagg gaagcgagag ggtgacctgg   1260
agcgaatccc aaaaataacg tctcagttcg gattgtagtc tgcaactcga ctacatgaag   1320
ctggaatcgc tagtaatcgc ggatcagcat gccgcggtga atacgttccc gggtcttgta   1380
cacaccgccc gtcacaccat gggagtcagt aacgcccgaa gccagtgacc caaccttaga   1440
ggagggagct gtcgaaggcg ggacggataa ctggggtgaa gtcgtaacaa ggtagccgta   1500
tcggaaggtg cggctggatc acctcctttt                                    1529

<210> SEQ ID NO 4
<211> LENGTH: 1527
<212> TYPE: DNA
<213> ORGANISM: Clostridium symbiosum

<400> SEQUENCE: 4
atgagagttt gatcctggct caggatgaac gctggcggcg tgcctaacac atgcaagtcg     60
aacgaagcga tttaacggaa gttttcggat ggaagttgaa ttgactgagt ggcggacggg    120
tgagtaacgc gtgggtaacc tgccttgtac tgggggacaa cagttagaaa tgactgctaa    180
taccgcataa gcgcacagta tcgcatgata cagtgtgaaa aactccggtg gtacaagatg    240
gacccgcgtc tgattagcta gttggtaagg taacggctta ccaaggcgac gatcagtagc    300
cgacctgaga gggtgaccgg ccacattggg actgagacac ggcccaaact cctacgggag    360
gcagcagtgg ggaatattgc acaatgggcg aaagcctgat gcagcgacgc cgcgtgagtg    420
aagaagtatt tcggtatgta aagctctatc agcagggaag aaaatgacgg tacctgacta    480
agaagccccg gctaactacg tgccagcagc cgcggtaata cgtaggggc aagcgttatc     540 cggatttact gggtgtaaag ggagcgtaga cggtaaagca agtctgaagt gaaagcccgc    600
ggctcaactg cgggactgct ttggaaactg tttaactgga gtgtcggaga ggtaagtgga    660
attcctagtg tagcggtgaa atgcgtagat attaggagga acaccagtgg cgaaggcgac    720
ttactggacg ataactgacg ttgaggctcg aaagcgtggg gagcaaacag gattagatac    780
cctggtagtc cacgccgtaa acgatgaata ctaggtgttg gggagcaaag ctcttcggtg    840
ccgtcgcaaa cgcagtaagt attccacctg gggagtacgt tcgcaagaat gaaactcaaa    900
ggaattgacg gggacccgca caagcggtgg agcatgtggt ttaattcgaa gcaacgcgaa    960
gaaccttacc aggtcttgac atcgatccga cggggagta acgtcccctt ccttcgggg     1020 cggagaagac aggtggtgca tggttgtcgt cagctcgtgt cgtgagatgt tgggttaagt   1080
cccgcaacga gcgcaaccct tattctaagt agccagcggt tcggccggga actcttggga   1140
gactgccagg gataacctgg aggaaggtgg ggatgacgtc aaatcatcat gccccttatg   1200
atctgggcta cacacgtgct acaatggcgt aaacaaagag aagcaagacc gcgaggtgga   1260
gcaaatctca aaaataacgt ctcagttcgg actgcaggct gcaactcgcc tgcacgaagc   1320
tggaatcgct agtaatcgcg aatcagaatg tcgcggtgaa tacgttcccg ggtcttgtac   1380
acaccgcccg tcacaccatg ggagtcagta acgcccgaag tcagtgaccc aaccgcaagg   1440
agggagctgc cgaaggcggg accgataact ggggtgaagt cgtaacaagg tagccgtatc   1500
ggaaggtgcg gctggatcac ctcctttt                                     1527

<210> SEQ ID NO 5
<211> LENGTH: 1531
<212> TYPE: DNA
<213> ORGANISM: Blautia producta
```

<400> SEQUENCE: 5

```
atcagagagt tgatcctgg ctcaggatga acgctggcgg cgtgcttaac acatgcaagt      60
cgagcgaagc acttaagtgg atctcttcgg attgaagctt atttgactga gcggcggacg    120
ggtgagtaac gcgtgggtaa cctgcctcat acagggggat aacagttaga atggctgct     180
aataccgcat aagcgcacag gaccgcatgg tctggtgtga aaaactccgg tggtatgaga    240
tggacccgcg tctgattagc tagttggagg ggtaacggcc caccaaggcg acgatcagta    300
gccggcctga gagggtgaac ggccacattg gactgagac acggcccaga ctcctacggg    360
aggcagcagt ggggaatatt gcacaatggg gaaaccctg atgcagcgac gccgcgtgaa    420
ggaagaagta tctcggtatg taaacttcta tcagcaggga agaaaatgac ggtacctgac    480
taagaagccc cggctaacta cgtgccagca gccgcggtaa tacgtagggg gcaagcgtta    540
tccggattta ctgggtgtaa agggagcgta gacggaagag caagtctgat gtgaaaggct    600
ggggcttaac cccaggactg cattggaaac tgttttttcta gagtgccgga gaggtaagcg    660
gaattcctag tgtagcggtg aaatgcgtag atattaggag gaacaccagt ggcgaaggcg    720
gcttactgga cggtaactga cgttgaggct cgaaagcgtg gggagcaaac aggattagat    780
accctggtag tccacgccgt aaacgatgaa tactaggtgt cgggtggcaa agccattcgg    840
tgccgcagca acgcaataa gtattccacc tggggagtac gttcgcaaga atgaaactca    900
aaggaattga cggggacccg cacaagcggt ggagcatgtg gtttaattcg aagcaacgcg    960
aagaacctta ccaagtcttg acatccctct gaccggcccg taacggggcc ttccccttcgg   1020
ggcagaggag acaggtggtg catggttgtc gtcagctcgt gtcgtgagat gttgggttaa    1080
gtcccgcaac gagcgcaacc cctatcctta gtagccagca ggtgaagctg gcactctag    1140
ggagactgcc ggggataacc cggaggaagg cggggacgac gtcaaatcat catgcccctt    1200
atgatttggg ctacacacgt gctacaatgg cgtaaacaaa gggaagcgag acagcgatgt    1260
tgagcaaatc ccaaaaataa cgtcccagtt cggactgcag tctgcaactc gactgcacga    1320
agctggaatc gctagtaatc gcgaatcaga atgtcgcggt gaatacgttc ccgggtcttg    1380
tacacaccgc ccgtcacacc atgggagtca gtaacgcccg aagtcagtga cccaaccttta    1440
caggagggag ctgccgaagg cgggaccgat aactggggtg aagtcgtaac aaggtagccg    1500
tatcggaagg tgcggctgga tcacctcctt t                                   1531
```

<210> SEQ ID NO 6
<211> LENGTH: 1529
<212> TYPE: DNA
<213> ORGANISM: Dorea Longicatena

<400> SEQUENCE: 6

```
aacgagagtt tgatcctggc tcaggatgaa cgctggcggc gtgcttaaca catgcaagtc     60
gagcgaagca cttaagtttg attcttcgga tgaagacttt tgtgactgag cggcggacgg    120
gtgagtaacg cgtgggtaac ctgcctcata caggggata acagttagaa atgactgcta    180
ataccgcata agaccacggt accgcatggt acagtggtaa aaactccggt ggtatgagat    240
ggacccgcgt ctgattaggt agttggtggg gtaacggcct accaagccga cgatcagtag    300
ccgacctgag agggtgaccg gccacattgg gactgagaca cggcccagac tcctacggga    360
ggcagcagtg ggaatattg cacaatggag gaaactctga tgcagcgacg ccgcgtgaag    420
gatgaagtat tcggtatgt aaacttctat cagcagggaa gaaaatgacg gtacctgact    480
aagaagcccc ggctaactac gtgccagcag ccgcggtaat acgtaggggg caagcgttat    540
```

-continued

```
ccggatttac tgggtgtaaa gggagcgtag acggcacggc aagccagatg tgaaagcccg      600
gggctcaacc ccgggactgc atttggaact gctgagctag agtgtcggag aggcaagtgg      660
aattcctagt gtagcggtga aatgcgtaga tattaggagg aacaccagtg gcgaaggcgg      720
cttgctggac gatgactgac gttgaggctc gaaagcgtgg ggagcaaaca ggattagata      780
ccctggtagt ccacgccgta aacgatgact gctaggtgtc gggtggcaaa gccattcggt      840
gccgcagcta acgcaataag cagtccacct ggggagtacg ttcgcaagaa tgaaactcaa      900
aggaattgac ggggacccgc acaagcggtg gagcatgtgg tttaattcga agcaacgcga      960
agaaccttac ctgatcttga catcccgatg accgcttcgt aatggaagct tttcttcgga     1020
acatcggtga caggtggtgc atggttgtcg tcagctcgtg tcgtgagatg ttgggttaag     1080
tcccgcaacg agcgcaaccc ctatcttcag tagccagcag gttaagctgg gcactctgga     1140
gagactgcca gggataacct ggaggaaggt ggggatgacg tcaaatcatc atgcccctta     1200
tgaccagggc tacacacgtg ctacaatggc gtaaacaaag agaagcgaac tcgcgagggt     1260
aagcaaatct caaaaataac gtctcagttc ggattgtagt ctgcaactcg actacatgaa     1320
gctggaatcg ctagtaatcg cagatcagaa tgctgcggtg aatacgttcc cgggtcttgt     1380
acacaccgcc cgtcacacca tgggagtcag taacgcccga agtcagtgac ccaaccgtaa     1440
ggagggagct gccgaaggtg ggaccgataa ctggggtgaa gtcgtaacaa ggtagccgta     1500
tcggaaggtg cggctggatc acctcctttt                                      1529

<210> SEQ ID NO 7
<211> LENGTH: 1537
<212> TYPE: DNA
<213> ORGANISM: Erysipelotrichaceae bacterium

<400> SEQUENCE: 7
atggagagtt tgatcctggc tcaggatgaa cgctggcggc atgcctaata catgcaagtc       60
gaacgaagtt tcgaggaagc ttgcttccaa agagacttag tggcgaacgg gtgagtaaca      120
cgtaggtaac ctgcccatgt gtccgggata actgctggaa acggtagcta aaaccggata      180
ggtatacaga gcgcatgctc agtatattaa agcgcccatc aaggcgtgaa catggatgga      240
cctgcggcgc attagctagt tggtgaggta acggcccacc aaggcgatga tgcgtagccg      300
gcctgagagg gtaaacggcc acattgggac tgagacacgg cccaaactcc tacgggaggc      360
agcagtaggg aattttcgtc aatggggaa acctgaacg agcaatgccg cgtgagtgaa        420
gaaggtcttc ggatcgtaaa gctctgttgt aagtgaagaa cggctcatag aggaaatgct      480
atgggagtga cggtagctta ccagaaagcc acggctaact acgtgccagc agccgcggta      540
atacgtaggt ggcaagcgtt atccggaatc attgggcgta aagggtgcgt aggtggcgta      600
ctaagtctgt agtaaaaggc aatggctcaa ccattgtaag ctatggaaac tggtatgctg      660
gagtgcagaa gagggcgatg gaattccatg tgtagcggta aaatgcgtag atatatggag      720
gaacaccagt ggcgaaggcg gtcgcctggt ctgtaactga cactgaggca cgaaagcgtg      780
gggagcaaat aggattagat accctagtag tccacgccgt aaacgatgag aactaagtgt      840
tggaggaatt cagtgctgca gttaacgcaa taagttctcc gcctgggag tatgcacgca      900 agtgtgaaac tcaaaggaat tgacgggggc cgcacaagc ggtggagtat gtggtttaat      960
tcgaagcaac gcgaagaacc ttaccaggcc ttgacatgga aacaaatacc ctagagatag     1020
ggggataatt atggatcaca caggtggtgc atggttgtcg tcagctcgtg tcgtgagatg     1080
```

| | |
|---|---|
| ttgggttaag tcccgcaacg agcgcaaccc ttgtcgcatg ttaccagcat caagttgggg | 1140 |
| actcatgcga gactgccggt gacaaaccgg aggaaggtgg ggatgacgtc aaatcatcat | 1200 |
| gccccttatg gcctgggcta cacacgtact acaatggcgg ccacaaagag cagcgacaca | 1260 |
| gtgatgtgaa gcgaatctca taaaggtcgt ctcagttcgg attgaagtct gcaactcgac | 1320 |
| ttcatgaagt cggaatcgct agtaatcgca gatcagcatg ctgcggtgaa tacgttctcg | 1380 |
| ggccttgtac acaccgcccg tcaaaccatg ggagtcagta atacccgaag ccggtggcat | 1440 |
| aaccgtaagg agtgagccgt cgaaggtagg accgatgact ggggttaagt cgtaacaagg | 1500 |
| tatccctacg ggaacgtggg gatggatcac ctcctttt | 1537 |

<210> SEQ ID NO 8
<211> LENGTH: 1530
<212> TYPE: DNA
<213> ORGANISM: Subdoligranulum spp

<400> SEQUENCE: 8

| | |
|---|---|
| tattgagagt ttgatcctgg ctcaggatga acgctggcgg cgtgcttaac acatgcaagt | 60 |
| cgaacggggt gctcatgacg gaggattcgt ccaacggatt gagttaccta gtggcggacg | 120 |
| ggtgagtaac gcgtgaggaa cctgccttgg agaggggaat aacactccga aaggagtgct | 180 |
| aataccgcat gatgcagttg ggtcgcatgg ctctgactgc caaagattta cgctctgag | 240 |
| atggcctcgc gtctgattag ctagtaggcg gggtaacggc ccacctaggc gacgatcagt | 300 |
| agccggactg agaggttgac cggccacatt gggactgaga cacggcccag actcctacgg | 360 |
| gaggcagcag tggggaatat tgggcaatgg gcgcaagcct gacccagcaa cgccgcgtga | 420 |
| aggaagaagg ctttcgggtt gtaaacttct tttgtcgggg acgaaacaaa tgacggtacc | 480 |
| cgacgaataa gccacggcta actacgtgcc agcagccgcg gtaatacgta ggtggcaagc | 540 |
| gttatccgga tttactgggt gtaaagggcg tgtaggcggg attgcaagtc agatgtgaaa | 600 |
| actgggggct caacctccag cctgcatttg aaactgtagt tcttgagtgc tggagaggca | 660 |
| atcggaattc cgtgtgtagc ggtgaaatgc gtagatatac ggaggaacac cagtggcgaa | 720 |
| ggcggattgc tggacagtaa ctgacgctga ggcgcgaaag cgtggggagc aaacaggatt | 780 |
| agataccctg gtagtccacg ccgtaaacga tggatactag gtgtgggggg tctgaccccc | 840 |
| tccgtgccgc agttaacaca ataagtatcc cacctgggga gtacgatcgc aaggttgaaa | 900 |
| ctcaaaggaa ttgacggggg cccgcacaag cggtggagta tgtggtttaa ttcgaagcaa | 960 |
| cgcgaagaac cttaccaggg cttgacatcc cactaacgaa gcagagatgc attaggtgcc | 1020 |
| cttcggggaa agtggagaca ggtggtgcat ggttgtcgtc agctcgtgtc gtgagatgtt | 1080 |
| gggttaagtc ccgcaacgag cgcaacccct tattgttagtt gctacgcaag agcactctag | 1140 |
| cgagactgcc gttgacaaaa cggaggaagg tggggacgac gtcaaatcat catgcccctt | 1200 |
| atgtcctggg ccacacacgt actacaatgg tggttaacag agggaggcaa taccgcgagg | 1260 |
| tggagcaaat ccctaaaagc catcccagtt cggattgcag gctgaaaccc gcctgtatga | 1320 |
| agttggaatc gctagtaatc gcggatcagc atgccgcggt gaatacgttc ccgggccttg | 1380 |
| tacacaccgc ccgtcacacc atgagagtcg gaacacccg aagtccgtag cctaaccgca | 1440 |
| aggagggcgc ggccgaaggt gggttcgata attggggtga agtcgtaaca aggtagccgt | 1500 |
| atcggaaggt gcggctggat cacctccttt | 1530 |

<210> SEQ ID NO 9
<211> LENGTH: 325

```
<212> TYPE: DNA
<213> ORGANISM: Clostridium hathewayi

<400> SEQUENCE: 9
gatgaacgct ggcggcggtg cttaacacat gcaagtcgag cgaagcggtt tcgagtgaag      60
ttttggatgg aattgaaatt gacttagcgg cggacgggtg agtaacgcgt gggtaacctg     120
ccttacactg ggggataaca gttagaaatg actgctaata ccgcataagc gcacagggcc     180
gcatggtctg gtgcgaaaaa ctccggtggt gtaagatgga cccgcgtctg attaggtagt     240
tggtggggta acggcccacc aagccgacga tcagtagccg acctgagagg gtgaccggcc     300
acattgggac tgagacacgg cccaa                                           325

<210> SEQ ID NO 10
<211> LENGTH: 325
<212> TYPE: DNA
<213> ORGANISM: Clostridium indolis / Anaerostipes caccae

<400> SEQUENCE: 10
gatgaacgct ggcggcgtgc ttaacacatg caagtcgaac gaagcatttt ggaaggaagt      60
tttcggatgg aattccttaa tgactgagtg gcggacgggt gagtaacgcg tggggaacct     120
gccctataca gggggataac agctggaaac ggctgctaat accgcataag cgcacagaat     180
cgcatgattc ggtgtgaaaa gctccggcag tataggatgg tcccgcgtct gattagctgg     240
ttggcgggt aacggcccac caaggcgacg atcagtagcc ggcttgagag agtggacggc      300
cacattggga ctgagacacg gccca                                           325

<210> SEQ ID NO 11
<211> LENGTH: 322
<212> TYPE: DNA
<213> ORGANISM: Lachnospiraceae bacterium

<400> SEQUENCE: 11
gatgaacgct ggcggcgtgc ctaacacatg caagtcgaac ggagttatgc agaggaagtt      60
tcggatgga atcggcgtaa cttagtggcg gacgggtgag taacgcgtgg gaaacctgcc      120
ctgtaccggg ggataacact tagaaatagg tgctaatacc gcataagcgc acagcttcac     180
atgaagcagt gtgaaaaact ccggtggtac aggatggtcc cgcgtctgat tagccagttg     240
gcagggtaac ggcctaccaa agcgacgatc agtagccggc tgagagggt gaacggccac      300
attgggactg agacacggcc ca                                              322

<210> SEQ ID NO 12
<211> LENGTH: 324
<212> TYPE: DNA
<213> ORGANISM: Clostridium species

<400> SEQUENCE: 12
gatgaacgct ggcggcgtgc ctaacacatg caagtcgaac gaagcatccc ataggaagtt      60
tcggatgga atatgggatg actgagtggc ggacgggtga gtaacgcgtg gataacctgc      120
ctcacactgg gggataacag ttagaaatgc tgctaatac cgcataagcg cacagtaccg      180
catggtacgg tgtgaaaaac ccaggtggtg tgagatggat ccgcgtctga ttagccagtt     240
ggcggggtaa cggcccacca aagcgacgat cagtagccga cctgagaggg tgaccggcca     300
cattggggac tgagacacgg ccca                                            324

<210> SEQ ID NO 13
```

```
<211> LENGTH: 323
<212> TYPE: DNA
<213> ORGANISM: Lachnospiraceae bacterium

<400> SEQUENCE: 13
gatgaacgct ggcggcgtgc ctaacacatg caagtcgaac gaagttagac agaggaagtt      60
ttcggatgga atcggtataa cttagtggcg gacgggtgag taacgcgtgg gaaacctgcc     120
ctgtaccggg ggataacact tagaaatagg tgctaatacc gcataagcgc acggaaccgc     180
atgggttctg tgtgaaaact ccggtggtac aggatggtcc cgcgtctgat tagccagttg     240
gcagggtaac ggcctaccaa agcgacgatc agtagccggc ctgagagggt gaacggccac     300
attgggactg agacacggcc caa                                             323
```